US012751668B2

(12) United States Patent
Yang et al.

(10) Patent No.: US 12,751,668 B2
(45) Date of Patent: Oct. 6, 2026

(54) WEARABLE DEVICE AND AIRBAG PREPARATION METHOD

(71) Applicant: Huawei Technologies Co., Ltd., Shenzhen (CN)

(72) Inventors: Rongguang Yang, Dongguan (CN); Changming Li, Dongguan (CN); Wenjian Yang, Dongguan (CN); Junye Jin, Dongguan (CN); Lei Zhang, Xi'an (CN); Qian He, Xi'an (CN); Gang Wang, Shanghai (CN)

(73) Assignee: Huawei Technologies Co., Ltd., Shenzhen (CN)

( * ) Notice: Subject to any disclaimer, the term of this patent is extended or adjusted under 35 U.S.C. 154(b) by 508 days.

(21) Appl. No.: 18/270,318

(22) PCT Filed: Dec. 21, 2021

(86) PCT No.: PCT/CN2021/140222
§ 371 (c)(1),
(2) Date: Jun. 29, 2023

(87) PCT Pub. No.: WO2022/143312
PCT Pub. Date: Jul. 7, 2022

(65) Prior Publication Data

US 2024/0050037 A1 Feb. 15, 2024

(30) Foreign Application Priority Data

Dec. 31, 2020 (CN) ......................... 202011633586.7
Dec. 17, 2021 (CN) ......................... 202111549923.9

(51) Int. Cl.
*A61B 5/00* (2006.01)
*A44C 5/00* (2006.01)
(Continued)

(52) U.S. Cl.
CPC .......... *A61B 5/681* (2013.01); *A61B 5/02141* (2013.01); *A61B 5/02233* (2013.01); *A61B 5/683* (2013.01); *A61B 2560/0443* (2013.01)

(58) Field of Classification Search
CPC . A61B 5/681; A61B 5/02141; A61B 5/02233; A61B 5/683; A61B 2560/0443;
(Continued)

(56) References Cited

U.S. PATENT DOCUMENTS 5,660,182 A * 8/1997 Kuroshaki ......... A61B 5/02233 600/499
2010/0010357 A1* 1/2010 Ostrowiecki ...... A61B 5/02233 600/499
(Continued)

FOREIGN PATENT DOCUMENTS

CN 2769209 Y 4/2006
CN 1792320 A 6/2006
(Continued)

*Primary Examiner* — Justin Xu
(74) *Attorney, Agent, or Firm* — Slater Matsil, LLP

(57) ABSTRACT

A wearable device and an airbag preparation method. The wearable device includes a watch body, an airbag, and an airbag cover. The airbag is detachably connected to an end of the watch body, so that a coverage area of the airbag for the watch body is small, thereby reserving space for installing another module on the watch body. The airbag includes a first layer structure and a second layer structure that are
(Continued)

superposed. The first layer structure has a first cavity, the second layer structure has a second cavity, and the first cavity communicates with the second cavity.

12 Claims, 36 Drawing Sheets

(51) Int. Cl.

| | |
|---|---|
| ***A61B 5/021*** | (2006.01) |
| ***A61B 5/022*** | (2006.01) |
| ***A61B 5/024*** | (2006.01) |
| *A61B 5/0225* | (2006.01) |

(58) Field of Classification Search

CPC ............ A61B 5/02255; A61B 5/02416; A61B 5/02438; A61B 5/0225; A44C 5/00

See application file for complete search history.

(56) References Cited

U.S. PATENT DOCUMENTS

| | | | | |
|---|---|---|---|---|
| 2014/0221854 | A1* | 8/2014 | Wai | A61B 5/0059 600/508 |
| 2018/0192900 | A1 | 7/2018 | Wei | |
| 2019/0298181 | A1 | 10/2019 | Iwata et al. | |
| 2020/0129122 | A1 | 4/2020 | Mou et al. | |
| 2023/0019122 | A1* | 1/2023 | Xia | A61B 5/681 |

FOREIGN PATENT DOCUMENTS

| | | | |
|---|---|---|---|
| CN | 204632328 | U | 9/2015 |
| CN | 105054919 | A | 11/2015 |
| CN | 105078431 | A | 11/2015 |
| CN | 205903250 | U | 1/2017 |
| CN | 206710801 | U | 12/2017 |
| CN | 207817932 | U | 9/2018 |
| CN | 109497664 | A | 3/2019 |
| CN | 109864400 | A | 6/2019 |
| CN | 209826699 | U | 12/2019 |
| CN | 210019307 | U | 2/2020 |
| CN | 111050241 | A | 4/2020 |
| CN | 210726885 | U | 6/2020 |
| CN | 111557526 | A | 8/2020 |
| CN | 211243345 | U | 8/2020 |
| CN | 211299953 | U | 8/2020 |
| CN | 211749571 | U | 10/2020 |
| CN | 111920401 | A | 11/2020 |
| CN | 114680852 | A | 7/2022 |
| JP | 3051839 | U | 9/1998 |
| JP | 3202421 | B2 | 8/2001 |
| JP | 2019118409 | A | 7/2019 |
| KR | 20090029556 | A | 3/2009 |
| WO | 2017136383 | A1 | 8/2017 |

* cited by examiner

WEARABLE DEVICE AND AIRBAG PREPARATION METHOD

CROSS-REFERENCE TO RELATED APPLICATIONS

This application is a National Stage of International Application No. PCT/CN202040222, filed on Dec. 21, 2021, which claims priority to Chinese Patent Application No. 202111549923.9, filed on Dec. 17, 2021, and Chinese Patent Application No. 202011633586.7, filed on Dec. 31, 2020. All of the aforementioned applications are hereby incorporated by reference in their entireties.

TECHNICAL FIELD

This application relates to the field of electronic device technologies, and in particular, to a wearable device and an airbag preparation method.

BACKGROUND

Nowadays, people pay more and more attention to health statuses of themselves and their families, and therefore, blood pressure measurement becomes particularly important. However, an arm-type blood pressure monitor or a wrist-type blood pressure monitor is large in size, and is inconvenient to carry and use.

Currently, a wearable device with a function of monitoring human blood pressure, such as a smartwatch or a band, is one of important products for mobile and online health detection, and is widely praised by users. However, due to existence of an airbag and a relatively large volume of the airbag, some blood pressure watches on the market do not have sufficient space for disposing another function module. Consequently, function integration of the blood pressure watches is affected, and user experience is poor.

SUMMARY

This application provides a wearable device and an airbag preparation method, to improve a function integration degree of the wearable device and improve blood pressure measurement precision.

According to a first aspect, this application provides a wearable device. The wearable electronic device may include a watch body, an airbag, and an airbag cover. The airbag includes a first layer structure and a second layer structure that are superposed. The first layer structure has a first cavity, the second layer structure has a second cavity, and the first cavity and the second cavity are connected to form an air cavity of the airbag. In this way, the air cavity of the airbag is large, thereby helping improve accuracy of blood pressure detection. In addition, the airbag cover is detachably connected to the watch body, and the airbag may be detachably connected to an end of the watch body by using the airbag cover. In this way, a coverage area of the airbag for the watch body is small, so that the watch body may reserve space for disposing another function module, thereby improving a function integration degree of the wearable device.

In a possible implementation of this application, in order to implement a blood pressure detection function that can be set in a wearable manner, the watch body may include an air chamber, an air pump, and a pressure sensor. The air chamber has an air nozzle installation hole and an air inlet/air outlet, an air supply opening of the air pump communicates with the air inlet/air outlet, and the pressure sensor is configured to detect atmospheric pressure in the air chamber. In addition, an air nozzle is disposed on the second layer structure of the airbag, an air hole of the air nozzle communicates with the second cavity, and the air nozzle may be inserted into the air nozzle installation hole. In this way, air enters a pump body from an air inlet of the air pump, and then enters the air chamber through the air supply opening of the air pump and the air inlet/air outlet of the air chamber. With the increase of air in the air chamber, the air enters the airbag through the air nozzle to inflate the airbag. After the air cavity of the airbag is fully filled with air, the barometric pressure in the air chamber gradually increases. In this case, a real-time barometric pressure value may be read by using a pressure sensor. After the barometric pressure value reaches a specified value, the air pump stops working. After blood pressure measurement ends, because barometric pressure in the airbag and the air chamber is greater than external atmospheric pressure, the air flows out from the inlet/air outlet of the air chamber, enters the air pump through the air supply opening of the air pump, and is discharged through an air vent of the air pump. In this way, one blood pressure measurement is completed.

In this application, flow paths of the air in a process of charging and exhausting the airbag may be same. Therefore, in this application, an air nozzle installation hole may be disposed on the air chamber, and the airbag has an air nozzle. In this way, a part that is of the airbag and that connects to the watch body may be small, so that the coverage area of the airbag for the watch body may be small.

When the wearable device is in use, in order to enable the airbag to fit a wearing part of a user, the airbag is usually bent, to enable the air to flow smoothly in the air cavity of the airbag when the airbag is bent. In a possible implementation of this application, a first flexible inner object may be disposed in the first layer structure. At least a part of the first flexible inner object is fastened to an inner wall of the first layer structure, and an extension direction of the first flexible inner object and an extension direction of the first layer structure may be same.

Similarly, a second flexible inner object may be disposed in the second layer structure, and one end of the second flexible inner object may be connected to the air nozzle. The first flexible inner object and the second flexible inner object are disposed, so that there is a specific clearance between side walls when the airbag is bent, the air cavity in the airbag can be unblocked, thereby reducing impact on measurement precision and ensuring implementation of a product function.

In addition, a support protrusion may be further disposed on an end face that is of the nozzle and that is inside the second layer structure, and there may be one or more support protrusions. The support protrusion may be disposed on a peripheral side of the air hole of the air nozzle. In this way, even when the airbag is bent, a side wall that is of the airbag and that is located near the air nozzle is prevented from blocking the air hole of the air nozzle under support of the support protrusion, so that external air can smoothly enter the airbag through the air nozzle, thereby ensuring an air filling amount of the airbag, reducing impact on measurement precision, and ensuring implementation of a product function.

In a possible implementation of this application, in order to connect the airbag to the watch body, an installation slot may be disposed at an end of a bottom surface of the watch body, so that the airbag and the airbag cover may be installed in the installation slot, to improve appearance flatness of the watch body and improve wearing experience of the user.

In addition, the airbag and the airbag cover are installed in the installation slot, so that a bottom surface of the watch body may reserve space for disposing another function module. For example, a PPG module may be disposed on the bottom surface of the watch body. The PPG module may be configured to continuously detect a heart rate value. By disposing both the airbag and the PPG module on the wearable device, a function of performing a single blood pressure measurement by using the airbag may be integrated with a continuous heart rate measurement function of the PPG module, and a problem of continuous blood pressure measurement is resolved by performing an accurate algorithm operation. In addition, an ECG detection module may be further disposed on the bottom surface of the watch body, to implement an electrocardiogram detection function of the wearable device.

There are many manners of detachable connections between the airbag cover and the watch body. In a possible implementation of this application, each of two oppositely disposed side walls of the installation slot is provided with one bayonet. In addition, the airbag cover includes a cover body, a first snap fit, and a second snap fit, the first snap fit and the second snap fit are respectively disposed at two opposite ends of the cover body. When the airbag cover is installed in the installation slot, the first snap fit may be snap-fitted to one bayonet of the installation slot, and the second snap fit may be snap-fitted to the other bayonet of the installation slot.

The first snap fit may be a mobile snap fit, and may move in a direction toward or away from the second snap fit. The cover body is provided with a first accommodating cavity and a first installation hole, the first snap fit is accommodated in the first accommodating cavity, and a part of the first snap fit may extend out of the first accommodating cavity through the first installation hole. In addition, the airbag cover further includes a first elastic component, and the first elastic component is accommodated in the first accommodating cavity. In a direction from the first snap fit to the second snap fit, the first elastic component is located between the first snap fit and a side wall of the first accommodating cavity, and elastically abuts against the first snap fit and the side wall of the first accommodating cavity separately. In this way, when the airbag cover is connected to the watch body, the first snap fit may be first completely accommodated in the first accommodating cavity, and the first elastic component is squeezed to accumulate elastic force. When the first snap fit is opposite to a bayonet of the installation slot of the watch body, the first snap fit may extend out of the first accommodating cavity through the first installation hole under the elastic force of the first elastic component, and be snap-fitted to the bayonet, to implement a fastening connection between the airbag cover and the watch body.

In order to remove the airbag cover from the watch body, the airbag cover may further include a snap fastener, and the snap fastener may be configured to drive the first snap fit to move in a direction toward or away from the second snap fit. A side that is of the cover body and that is away from the watch body is further provided with a second installation hole, and the second installation hole communicates with the first accommodating cavity. In addition, the first snap fit is provided with a jack. When the snap fit is specifically disposed, a plug is disposed on a side that is of the snap fit and that faces the watch body, the snap fastener may be installed in the second installation hole, and the plug is inserted into the jack. When the snap fastener is pushed and the snap fastener moves in the direction toward or away from the second snap fastener, the snap fastener may drive the first snap fit to move in the direction toward or away from the second snap fastener.

In a possible implementation of this application, the second snap fit may be a fastening snap fit, that is, the second snap fit is fastened to the cover body. When the airbag cover is connected to the watch body, the second snap fit may be first snap-fitted into one bayonet of the installation slot of the watch body, and then the first snap fit is snap-fitted into the other bayonet, to implement a detachable connection between the airbag cover and the watch body. In addition, when the airbag cover is disassembled from the watch body, the first snap fit may be first disassembled from the first bayonet to the first accommodating cavity of the cover body, and then the second snap fit is disassembled from the corresponding bayonet, so that the airbag cover can be removed.

It should be noted that, because a part of the airbag may be installed in the installation slot, when the airbag cover is snap-fitted to the watch body, the part that is of the airbag and that is accommodated in the installation slot is crimped on the watch body by the airbag cover, to implement a connection between the airbag and the watch body. In addition, after the airbag cover is disassembled from the watch body, the airbag may be easily disassembled from the watch body, to implement the detachable connection between the airbag and the watch body. In this way, the airbag may be replaced based on a requirement, to meet a wearing requirement of the user, and improve user experience.

In another possible implementation of this application, the second snap fit may alternatively be a mobile snap fit, and may move in a direction toward or away from the first snap fit. The cover body is further provided with a second accommodating cavity and a third installation hole, the second snap fit may be accommodated in the second accommodating cavity, and a part of the second snap fit may extend out of the second accommodating cavity through the third installation hole. In addition, the airbag cover further includes a second elastic component, and the second elastic component is accommodated in the second accommodating cavity. In a direction from the second snap fit to the first snap fit, the second elastic component is located between the second snap fit and a side wall of the second accommodating cavity, and elastically abuts against the second snap fit and the side wall of the second accommodating cavity separately. In this way, when the airbag cover is connected to the watch body, the second snap fit may be first completely accommodated in the second accommodating cavity, and the second elastic component is squeezed to accumulate elastic force. When the second snap fit is opposite to a bayonet of the installation slot of the watch body, the second snap fit may extend out of the second accommodating cavity through the third installation hole under the elastic force of the second elastic component, and be snap-fitted to the bayonet, to implement the fastening connection between the airbag cover and the watch body.

In this implementation, when the airbag cover is connected to the watch body, the airbag cover may be pressed into the installation slot of the watch body in a pressing manner, and the first snap fit and the second snap fit may be snap-fitted to snap fits on corresponding sides under elastic force of elastic components corresponding to the first snap fit and the second snap fit, so that the connection between the airbag cover and the watch body is implemented, and such an installation manner is more convenient for the airbag cover. In addition, when the airbag cover is disassembled from the watch body, the first snap fit may be first disassembled from the first bayonet to the first accommodating cavity of the cover body, and then the second snap fit is disassembled from the corresponding bayonet, so that the airbag cover can be removed.

In addition, the airbag cover may further include a fastening block, and the fastening block is fastened to the second accommodating cavity. The fastening block has a limiting hole, and the second elastic component may penetrate through the limiting hole. In this way, movement stability of the second elastic component can be effectively improved.

In order to facilitate installation of the first snap fit, the first elastic component, and the first accommodating cavity, and the second snap fit, the second elastic component, and the second accommodating cavity, an opening may be disposed on a side that is of each of the first accommodating cavity and the second accommodating cavity and that faces the watch body. In addition, the cover body further includes a snap fit cover, the snap fit cover is an integrally formed structure, and the snap fit cover covers the two openings, to improve appearance integrity of the airbag cover.

It should be noted that, because a part of the airbag may be installed in the installation slot, in this implementation, the airbag may be fastened to the airbag cover, and the part that is of the airbag and that connects to the watch body is located between the cover body and the snap fit cover. In this way, a detachable connection between the airbag and the watch body may be implemented through the detachable connection between the airbag cover and the watch body.

In addition, in order to improve reliability of the connection between the airbag and the airbag cover, a limiting block may be disposed on the cover body, and the part that is of the airbag and that connects to the watch body is provided with a limiting opening, and the limiting block is inserted into the limiting opening.

When the airbag cover and the watch body are connected through snap-fitting, in addition to the foregoing manner of disposing the snap fit on the airbag cover and disposing the bayonet on the watch body, the snap fit may alternatively be disposed on the watch body, and the bayonet is disposed on the airbag cover. During specific implementation, the airbag cover may include the cover body, the cover body has a third bayonet and a fourth bayonet, and the third snap fit and the fourth snap fit are located at two ends that are disposed opposite to each other and that are of the cover body. In addition, a third snap fit and a fourth snap fit are disposed on the watch body. The third snap fit and the fourth snap fit may move toward or away from each other, the third snap fit may be snap-fitted to the third bayonet, and the fourth snap fit may be snap-fitted to the fourth bayonet. In this way, the airbag cover and the watch body may be installed through snap-fitting of the third snap fit and the third bayonet, and snap-fitting of the fourth snap fit and the fourth bayonet. When the third snap fit is detached from the third bayonet, and/or the fourth snap fit is detached from the fourth bayonet, the airbag cover may be disassembled from the watch body, so that the airbag cover and the watch body can be installed and disassembled conveniently.

In order to install the airbag on the airbag cover, the airbag cover may further include a pressing plate, and the pressing plate may be fastened to the cover body. In this way, a part that is of the airbag and on which an air nozzle is disposed is located between the pressing plate and the cover body, so that the airbag and the cover body may be installed through fastening of the pressing plate and the cover body. In addition, the pressing plate is provided with an air nozzle hole, and the air nozzle may extend out of the air nozzle hole, to facilitate a connection between the air nozzle and the watch body.

In addition to the foregoing structure, the airbag cover may further include an elastic protrusion. The cover body has an accommodating cavity, the elastic protrusion may be disposed at the accommodating cavity, and the elastic protrusion may move in a direction toward or away from the accommodating cavity. When the elastic protrusion is specifically disposed, the elastic protrusion may include a protrusion cover and a third elastic component, and the third elastic component elastically abuts against the protrusion cover and a bottom wall of the accommodating cavity. In addition, a protrusion cover hole is further disposed on the pressing plate, and the protrusion cover extends from the protrusion cover hole to a side that is of the pressing plate and that is away from the cover body. Therefore, when moving in a direction toward the accommodating cavity, the protrusion cover may compress the third elastic component, so that the third elastic component accumulates elastic force. When releasing the elastic force, the third elastic component may drive the protrusion cover to move in a direction away from the accommodating cavity.

In this application, before the pressing plate is fastened to the cover body, a location at which the pressing plate is disposed on the cover body may be determined. In a possible implementation, the pressing plate may include a first end and a second end, and the first end and the second end are disposed opposite to each other. The first end may be disposed facing the fourth bayonet, and a snap-fitting part may be disposed at the first end. In addition, the cover body has an accommodating cavity, and a side wall of the accommodating cavity is provided with a snap-fitting slot, so that the snap-fitting part may be inserted into the snap-fitting slot, to implement limiting of the pressing plate on the cover body.

The pressing plate and the cover body may be fastened by using, but is not limited to, a manner in which a screw is tightly screwed. During specific implementation, a screw hole may be disposed on the pressing plate, so that a fastening connection between the pressing plate and the cover body may be implemented by screwing a screw that penetrates through the screw hole tightly into the cover body.

When the watch body is specifically disposed, the watch body may be provided with a first accommodating slot and a second accommodating slot. The first accommodating slot communicates with the installation slot through a first through hole, and the second accommodating slot communicates with the installation slot through a second through hole. In this way, the third snap fit may be accommodated in the first accommodating slot, a fourth elastic component may be disposed between the third snap fit and a side wall of the first accommodating slot, the fourth elastic component elastically abuts against the third snap fit and the side wall of the first accommodating slot separately, and a part of the third snap fit may extend from the first through hole to the installation slot. In addition, the fourth snap fit is accommodated in the second accommodating slot, a fifth elastic component is disposed between the fourth snap fit and a side wall of the second accommodating slot, the fifth elastic component elastically abuts against the fourth snap fit and the side wall of the second accommodating slot separately, and a part of the fourth snap fit may extend from the second through hole to the installation slot. In this case, when the third snap fit and the fourth snap fit move away from each other, corresponding elastic components are compressed, to accumulate elastic force. When the elastic components release the elastic force, the third snap fit and the fourth snap fit may move toward each other.

In a possible implementation of this application, the bottom surface of the watch body may be further provided with a third through hole, and the third through hole may communicate with the first accommodating slot. In addition, a snap fit button is further disposed on the watch body, and the third snap fit has an opening. The snap fit button passes through the opening and may be installed in the third through hole. In addition, the snap fit button may move in an axis direction of the third through hole, and in a process in which the snap fit button moves along the axis direction of the third through hole, the third snap fit may be driven to move toward or away from the first accommodating slot, so that a movement of the third snap fit may be controlled by using the snap fit button.

In addition, the watch body may be further provided with a fourth through hole, the fourth through hole communicates with the second accommodating slot, and an opening direction of the fourth through hole is opposite to an opening direction of the installation slot. In addition, the watch body is further provided with a snap fit support, and the snap fit support is installed in the fourth through hole. The snap fit support is provided with a protrusion, the fourth snap fit is provided with a recess. The protrusion is inserted into the recess, and the protrusion and the recess are in clearance fit. In this way, a movement of the fourth snap fit toward the third snap fit may be limited by using the protrusion. In addition, the snap fit support may further support the fourth snap fit.

In order to prevent the snap fit support from falling off from the watch body, a snap fit cover may be further disposed on the watch body. The snap fit support may be located between the fourth snap fit and the snap fit cover, and the snap fit cover may abut against the snap fit support. In this way, the snap fit cover is fastened to the watch body, so that the snap fit cover supports the snap fit support.

In a possible implementation of this application, a magnet may be disposed in the airbag cover, and a Hall element matching the magnet is disposed in the watch body, to determine, by detecting whether the magnet is connected to the Hall element, whether the airbag cover is installed in the watch body. When it is detected that the magnet is connected to the Hall element, it is determined that the airbag cover is installed, and the wearable device can be used normally. However, when it is detected that the magnet is not connected to the Hall element, it is determined that the airbag cover is not installed. In this case, the wearable device may send an alarm to remind the user that an internal structure of the watch body is in an exposed state at the air nozzle installation hole, so that the user can take a corresponding measure in time, to avoid a risk of water intrusion or a foreign matter caused by long-term exposure of the internal structure of the watch body.

In addition to the foregoing snap-fitting manner, the airbag cover and the watch body may be detachably connected in a magnetic attraction manner. During specific implementation, the airbag cover may include a cover body and a first magnetic element. The first magnetic element is disposed on the cover body. A second magnetic element may be disposed in the installation slot, and when the airbag cover is installed in the installation slot, the first magnetic element and the second magnetic element attract each other.

In this implementation, because a part of the airbag may be installed in the installation slot, when the airbag cover and the watch body are installed, the part of the airbag that is accommodated in the installation slot is crimped on the watch body by the airbag cover, to implement a connection between the airbag and the watch body. In addition, after the airbag cover is disassembled from the watch body, the airbag may be easily disassembled from the watch body, to implement the detachable connection between the airbag and the watch body. In this way, the airbag may be replaced based on a requirement, to meet a wearing requirement of the user, and improve user experience.

In a possible implementation of this application, the wearable device may further include a protective sleeve, and the protective sleeve is sleeved on the first layer structure of the airbag, and is detachably connected to the first layer structure. Sleeving the first layer structure on the first layer structure can protect the first layer structure, thereby reducing a risk of damage to the first layer structure. In addition, a material of the protective sleeve may be further selected, to improve wearing comfort of the user.

When the protective sleeve is specifically disposed, the protective sleeve may include a sleeve body and an edge wrap. The sleeve body covers at least a surface that is of the first layer structure and that is away from the second layer structure, and the edge wrap is disposed around an edge of the sleeve body. When the protective sleeve is sleeved on the first layer structure, arrangement of the edge wrap can improve reliability of a connection between the protective sleeve and the first layer structure, and prevent the protective sleeve from falling off from the first layer structure in a process in which the user wears the wearable arrangement.

According to a second aspect, this application further provides an airbag preparation method. The method may include: first, sleeving together a first layer structure and a second layer structure that have openings at two ends, where the first layer structure has a first cavity, the second layer structure has a second cavity, and the first layer structure is located in the second cavity; then, connecting partial areas of the first layer structure and the second layer structure to form a connection area; then, opening a through hole in the connection area, so that the first cavity communicates with the second cavity; and finally, flipping the second layer structure, so that the first layer structure and the second layer structure form a superposed structure.

In a possible implementation of this application, the connecting partial areas of the first layer structure and the second layer structure to form a connection area is specifically: connecting the partial areas of the first layer structure and the second layer structure by jointing through a hot melt process to form the connection area.

In a possible implementation of this application, after the flipping the second layer structure, so that the first layer structure and the second layer structure are superposed, the method further includes: performing leveling on the first layer structure and the second layer structure; then, installing an air nozzle on the second layer structure or the first layer structure; and Finally, sealing the two ends of the first layer structure and the second layer structure, to form a sealed airbag.

For the airbag obtained by using the airbag preparation method in this application, a connection area that is of the first layer structure and the second layer structure and that is formed by jointing through a hot melt process does not occupy inflatable space of the airbag. In this way, inflatable space of cavities of the two layer structures can be maximized in a limited size, and this helps improve measurement precision of a wearable device to which the airbag is applied.

BRIEF DESCRIPTION OF THE DRAWINGS

FIG. 20*a* and FIG. 10*b* are schematic diagrams of a structure of a watch body according to an embodiment of this application;

REFERENCE NUMERALS

Figure 1:
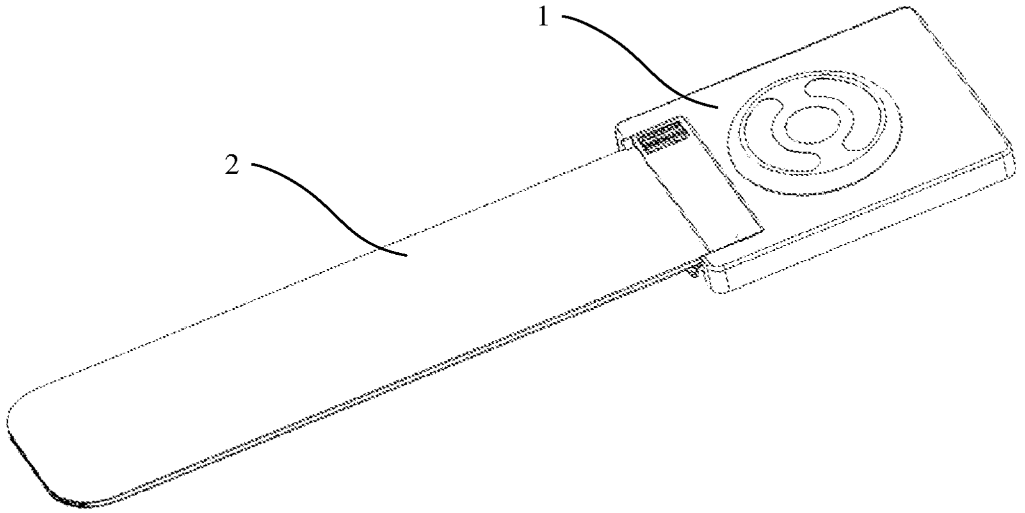
FIG. 1 is a schematic diagram of a structure of a wearable device according to an embodiment of this application.

1: watch body; 101: air pump; ion: air supply opening; 102: air chamber; 1021: air path; 1022: air inlet/air outlet;

1023: air nozzle installation hole; 103: pressure sensor; 104: installation slot; 1041: bayonet; 1042: recess;

1043: second magnetic element; 105: first accommodating slot; 106: second accommodating slot; 107: first through hole;

108: second through hole; 109: third through hole; no: step surface; in: fourth through hole;

2: airbag; 201: air nozzle; 2011: seal ring; 2012: support protrusion; 2013: air hole;

202: limiting opening; 203*a*: first layer structure; 203*b*: second layer structure; 2031: first cavity; 2032: second cavity;

204: flexible inner object; 204*a*: first flexible inner object; 204*b*: second flexible inner object; 205: through hole;

206: connection area; 207*a*: first curved surface structure; 207*b*: second curved surface structure; 207*c*: third curved surface structure;

207*d*: fourth curved surface structure; 208*a*: first cover surface structure; 208*b*: second cover surface structure; 3: PPG module;

4: ECG detection module; 5: airbag cover; 501: cover body; 5011*a*: accommodating cavity; 5011*b*: accommodating cavity; 5011*c*: accommodating cavity;

50111: snap-fitting slot; 50112: limiting post; 50113: guiding structure; 5012*a*: installation hole; 5012*b*: installation hole; 5012*bc*: installation hole;

5013: limiting block; 5014: third bayonet; 5015: fourth bayonet; 502: first snap fit; 5021: limiting post;

5022: jack; 50221: limiting protrusion; 503: second snap fit; 5031: limiting post; 504*a*: elastic component; 504*b*: elastic component;

505: snap fit cover; 5051: avoidance opening; 506: snap fastener; 5061: plug; 50611: limiting groove; 507: fastening block;

5071: limiting hole; 508: first magnetic element; 509: magnetic element cover; 510: pressing plate; 5101: air nozzle hole;

5102: snap-fitting part; 5103: screw hole; 5104: protrusion cover hole; 511: elastic protrusion; 51101: protrusion cover;

511011: flange structure; 51102: elastic component; 512: third snap fit; 51201: elastic component; 51202: limiting post;

51203: opening; 513: fourth snap fit; 51301: elastic component; 51302: limiting post; 51303: recess;

514: snap fit button; 51401: inclined surface; 515: limiting component; 516: snap fit support; 5161: protrusion; 6: protective sleeve;

601: sleeve body; and 602: edge wrap.

DETAILED DESCRIPTION OF ILLUSTRATIVE EMBODIMENTS

To make the objectives, technical solutions, and advantages of this application clearer, the following further describes this application in detail with reference to the accompanying drawings.

For ease of understanding of a wearable device provided in embodiments of this application, the following first describes an application scenario of the wearable device. The wearable device may be, but is not limited to, a portable electronic device such as a smartwatch or a smart band. A smartwatch is used as an example. The smartwatch may be worn on a wrist of a user, to detect a body sign such as blood pressure of the user at any time, to predict a body status, thereby effectively avoiding dangerous secondary disease such as stroke caused by hypertension.

A conventional smartwatch with a blood pressure detection function may generally include a watch body and an airbag. In order to improve detection accuracy, a volume of the airbag is usually large, and the airbag almost covers an entire bottom surface of the watch body. Consequently, the watch body does not have sufficient space for disposing another function module, and the smart watch has a simple function. In embodiments of this application, the bottom surface of the watch body is a contact surface of the watch body, and the contact surface may be configured to be in direct contact with a wearing part of the user. In addition, the watch body may further include a display surface, and the display surface may be disposed opposite to the contact surface.

In addition, in a process in which the airbag is inflated by using an air pump, when air flows out of the air pump, specific impact force is generated on the airbag. To avoid separation between the airbag and the air pump, the airbag needs to be fastened to the watch body. However, in some conventional smartwatches, a fastening structure between an airbag and a watch body is complex, and cannot be disassembled or is inconvenient to disassemble. Consequently, great inconvenience is caused for maintenance and replacement of the smartwatch and replacement of components.

Based on this, an embodiment of this application provides a wearable device, to improve a function integration degree of the wearable device, and improve blood pressure measurement precision. The wearable device provided in this application may be a smartwatch, a smart band, or the like that is worn on a wrist, or may be an electronic device that may be worn on another part of a human body for blood pressure detection. Regardless of a specific form of the wearable device, the wearable device may be disposed with reference to the wearable device in this application. For ease of understanding, in the following embodiments of this application, a smartwatch is used as an example to describe a structure of the wearable device in detail.

FIG. 1 is a schematic diagram of a structure of a wearable device according to an embodiment of this application. The wearable device may include a watch body 1 and an airbag 2. The watch body 1 and the airbag 2 are detachably connected, so that the airbag 2 can be conveniently disassembled and replaced with another watchband. In this way, various wearing requirements of a user are met, and user experience is improved.

Figure 2:
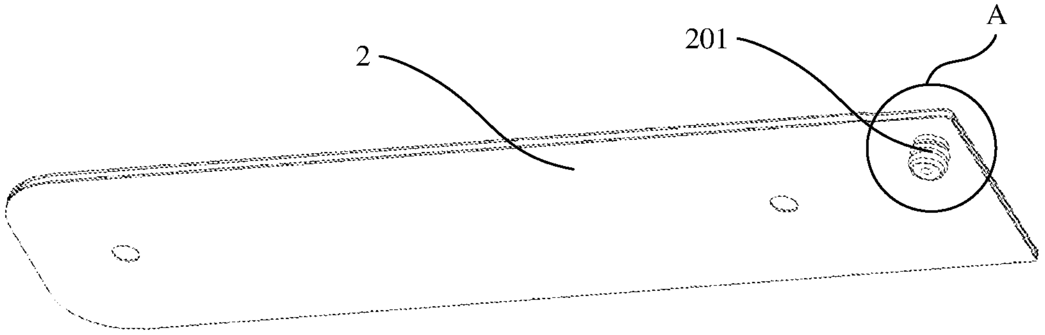
FIG. 2 is a schematic diagram of a structure an airbag according to an embodiment of this application.
Figure 3:
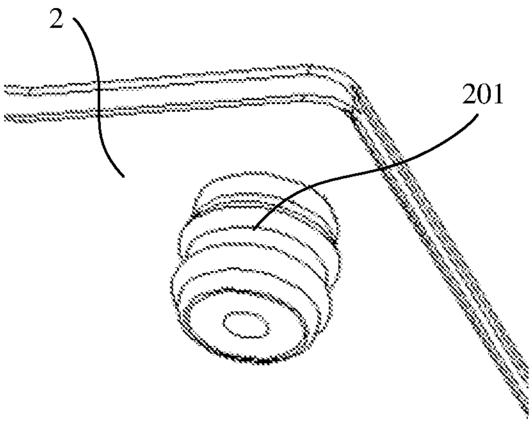
FIG. 3 is an enlarged view of a local structure at A in FIG. 2.
Figure 4:
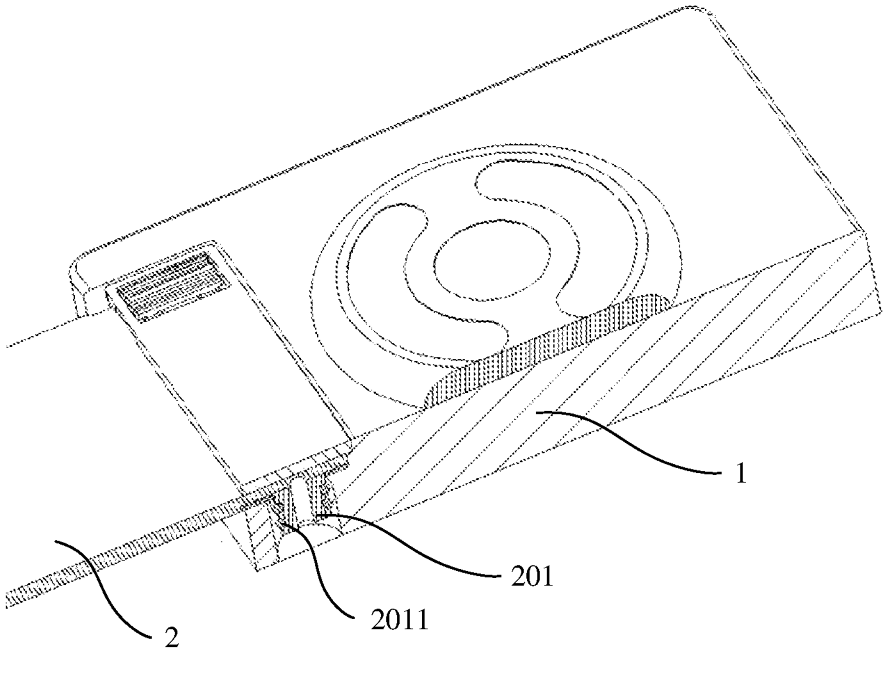
FIG. 4 is a sectional view of a wearable device according to an embodiment of this application.

Refer to FIG. 2. An air nozzle 201 is disposed at one end of the airbag 2, to implement a blood pressure detection function of the wearable device. The air nozzle 201 is connected to an air cavity of the airbag 2. Refer to FIG. 3. A ring groove structure may be disposed on a side wall of the air nozzle 201, and a seal ring 2011 (not shown in FIG. 3, and reference may be made to FIG. 4) may be further disposed in the ring groove structure, to seal the air nozzle 201. Refer to FIG. 4. In this way, when the air nozzle 201 is inserted into the watch body 1, air tightness of a joint between the airbag 2 and the watch body 1 can be improved, to help improve accuracy of blood pressure measurement.

Figure 5A:
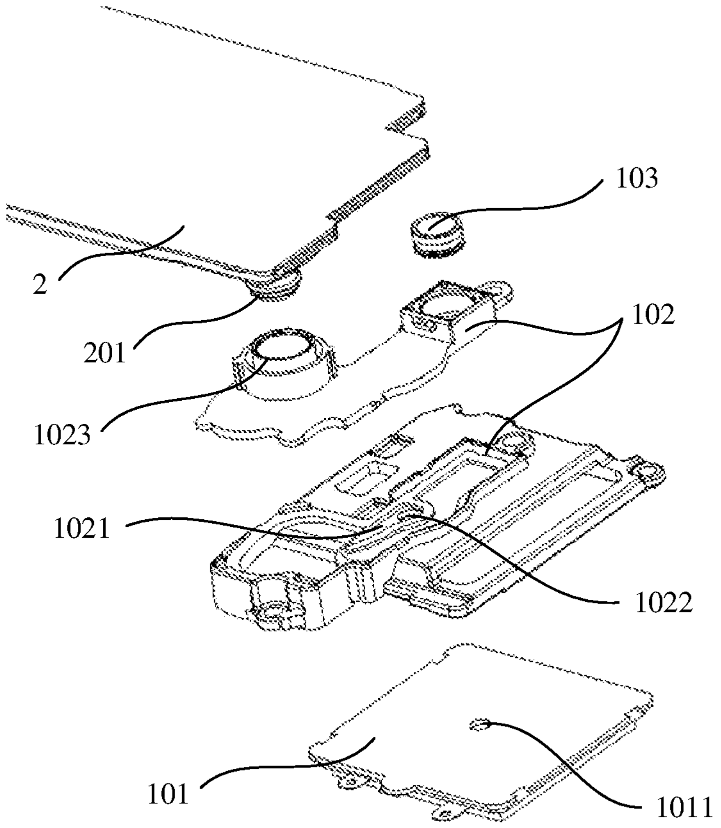
FIG. 5*a* to FIG. 5*c* are schematic diagrams of a blood pressure measurement principle of a wearable device according to an embodiment of this application.

Refer to FIG. 5*a*. FIG. 5*a* shows a specific structure that is configured to implement blood pressure detection and that is of the watch body 1. During specific implementation, the watch body 1 has an air pump 101, an air chamber 102, and a pressure sensor 103. The air pump 101 serves as an air source and is responsible for supplying air and exhaust air. The air chamber 102 includes a chamber of a cavity structure, and the air chamber 102 may be formed by two parts that are disposed in a snapped manner, or may be an integrally formed structure. The air chamber 102 has an air nozzle installation hole 1023 and an air inlet/air outlet 1022. The air nozzle 201 of the airbag 2 may be inserted into the air nozzle installation hole 1023, and an air supply opening 1011 of the air pump 101 communicates with the air inlet/air outlet 1022. The pressure sensor 103 is installed on a side wall of the air chamber 102. For example, the pressure sensor 103 may be disposed on a side that is of the air chamber 102 and that is close to the airbag 2, and the pressure sensor 103 may measure barometric pressure in the air chamber 102.

In addition, an air path 1021 is disposed in the air chamber 102 to guide air in the air chamber 102, thereby forming an air circulation loop. The air path 1021 is connected to the air pump 101 through the air inlet/air outlet 1022, and is connected to the airbag 2 through the air nozzle 201 that is inserted into the air nozzle installation hole 1023. In addition, the pressure sensor 103 may be connected to the air path 1021, and is configured to measure barometric pressure in the loop of the air path 1021.

Figure 5B:
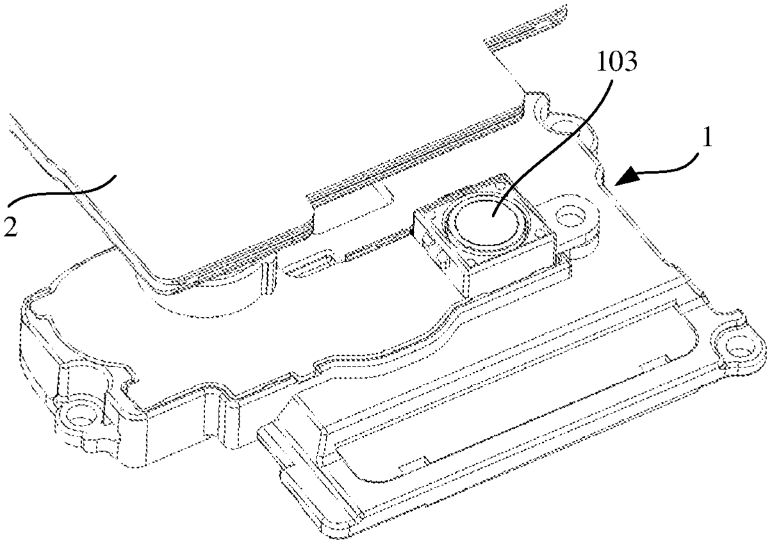
Figure 5C:
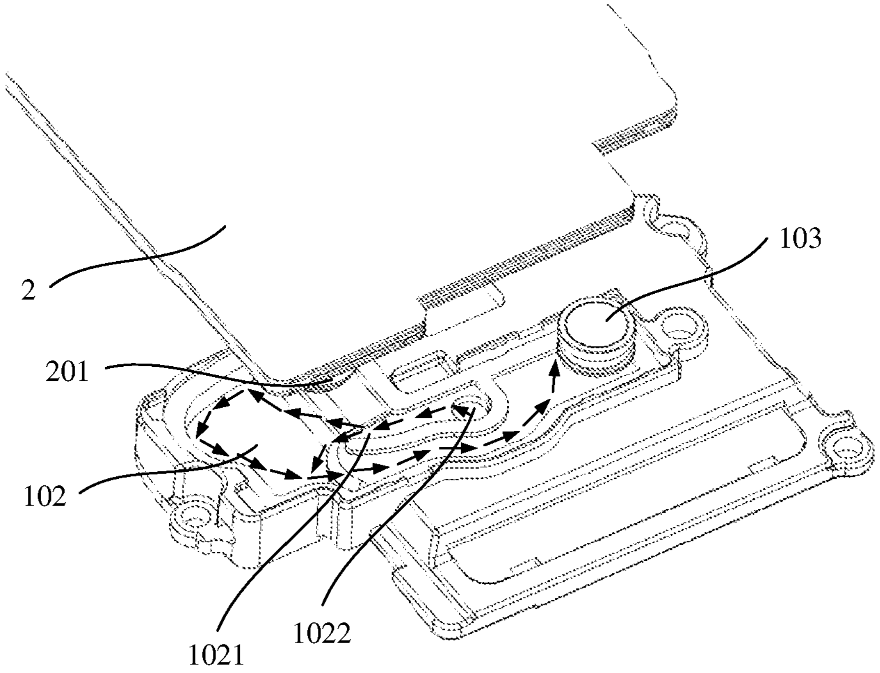

Refer to FIG. 5*b* and FIG. 5*c* together. FIG. 5*b* and FIG. 5*c* are schematic diagrams of a structure in which the airbag 2 is connected to the watch body 1. In FIG. 5*c*, a side wall that is of the air chamber 102 and that is close to the airbag 2 is omitted, to show flow of air in the air path 1021 when the air pump 101 inflates and deflates the airbag 2. First, an inflating process of the airbag 2 is described. An arrow in FIG. 5*c* indicates a flow direction of air in a process in which the air pump 101 inflates the airbag 2: When the air pump 101 (refer to FIG. 5*a*) works, air enters a pump body from an air inlet (not shown in the figure) of the air pump 101, then passes through an air supply opening of the air pump 101 and the air inlet/air outlet 1022 of the air chamber 102, and enters the air path 1021 of the air chamber 102. With an increase of air in the air chamber 102, the air enters the airbag 2 through the air nozzle 201 to inflate the airbag 2. After the air cavity of the airbag 2 is filled up with air, the barometric pressure in the air path 1021 gradually increases. In this case, a real-time barometric pressure value may be read by using the pressure sensor 103 located in the air chamber 102, and the air pump 101 stops working after the barometric pressure value reaches a specified value.

After blood pressure measurement ends, because the barometric pressure in the airbag 2 and the air chamber 102 is greater than external atmospheric pressure, the air flows out from the air inlet/air outlet 1022 of the air chamber 102, enters the air pump 101 through the air supply opening of the air pump 101, and is discharged through an air vent of the air pump 101. In this way, one blood pressure measurement is completed.

It may be understood from the foregoing description of a blood pressure detection process of the wearable device that, in this application, only one air nozzle 201 needs to be disposed on the airbag 2. In this way, a part that is of the airbag 2 and on which the air nozzle 201 is disposed may be connected to an end of the watch body 1, and a function of pressing a wrist artery by the airbag 2 during blood pressure measurement may be implemented by adjusting a length and a width of the airbag 2, and an internal structure of the airbag 2, to implement a blood pressure detection function of the wearable device. In this case, a coverage area of the airbag 2 for the watch body 1 is small, so that the watch body 1 reserves space for disposing another function module.

Figure 6:
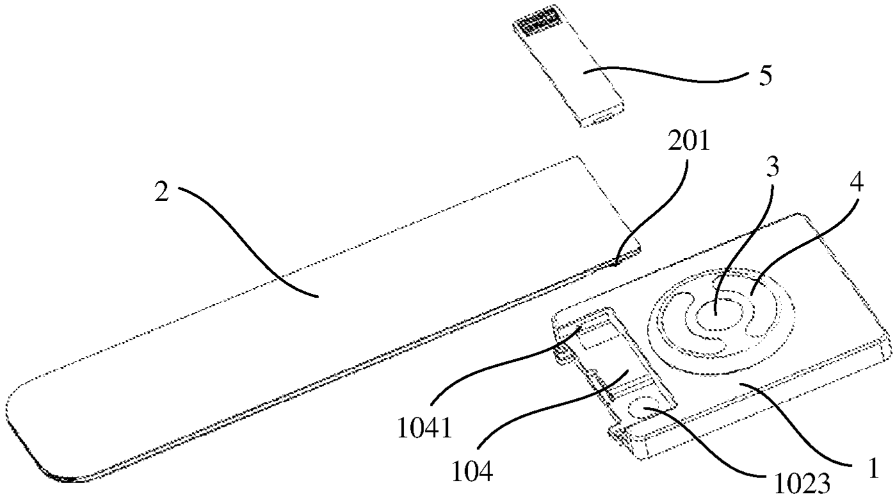
FIG. 6 is an exploded view of a structure of a wearable device according to an embodiment of this application.

Currently, a photoplethysmography (photoplethysmography, PPG) module is widely applied to a health detection device, and may receive, by using a photoelectric detector, light reflected by a human body, and obtain a heart rate value of a user through calculation and analysis. Therefore, refer to FIG. 6. FIG. 6 is a schematic diagram of a structure of a wearable device according to an embodiment of this application. A PPG module 3 may also be disposed on the wearable device provided in this application. Alternatively, the PPG module 3 may be disposed on a bottom surface of a watch body 1. In addition, the PPG module 3 may be disposed in a middle area of the watch body 1, to improve detection accuracy of the PPG module 3. Because the PPG module 3 may continuously measure a heart rate value of a human body, by disposing both an airbag 2 and the PPG module 3 on the wearable device, a function of performing a single blood pressure measurement by using the airbag 2 may be integrated with a continuous heart rate measurement function of the PPG module 3, and a problem of continuous blood pressure measurement is resolved by performing an accurate algorithm operation.

Still refer to FIG. 6. The wearable device in this embodiment of this application may be further provided with an electrocardiogram (electrocardiogram, ECG) detection module. An ECG detection module 4 may also be disposed on the bottom surface of the watch body 1. In addition, the ECG detection module 4 may be disposed in the middle area of the watch body 1, to implement an electrocardiogram detection function of the wearable device.

According to the wearable device in this application, function modules such as the airbag 2, the PPG module 3, and the ECG detection module 4 may be all disposed on the watch body 1, to improve a function integration degree of the wearable device. In addition, the function of performing a single blood pressure measurement by using the airbag 2 is integrated with the continuous heart rate measurement function of the PPG module 3, and the continuous blood pressure measurement is implemented by performing an algorithm operation. This helps improve blood pressure measurement precision.

There are a plurality of manners in which the airbag 2 may be detachably connected to the watch body 1. Still refer to FIG. 6. In a possible embodiment of this application, the wearable device may further include an airbag cover 5, and the airbag cover 5 is detachably connected to the watch body 1. In order to implement a fastening connection between the airbag cover 5 and the watch body 1, an end of the watch body 1 may be provided with an installation slot 104. The installation slot 104 may be disposed on a bottom surface of the watch body 1, and an air nozzle installation hole 1023 may be disposed on the installation slot 104. A part that is of the airbag 2 and on which the air nozzle 201 is disposed may be accommodated in the installation slot 104, and the air nozzle 201 may be inserted into the air nozzle installation hole 1023. In addition, a part or all of the airbag cover 5 is accommodated in the installation slot 104. In addition, each of two oppositely disposed side walls of the installation slot 104 is provided with one bayonet 1041. It may be understood that the installation slot 104 may be disposed on the bottom surface of the watch body 1, so that the airbag 2 can fit a wearing part, and appearance aesthetics of the wearable device can be improved.

Figure 7:
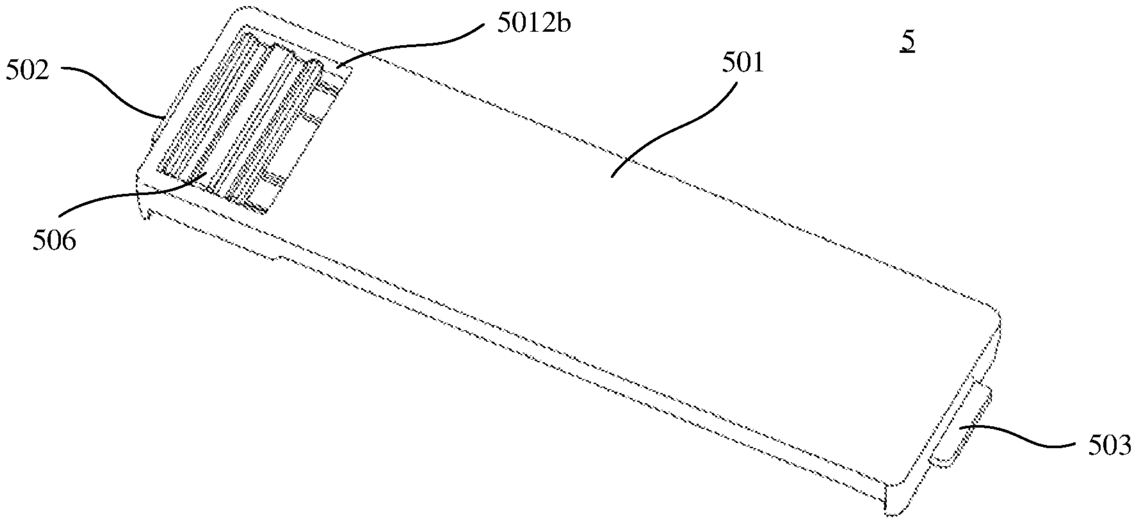
FIG. 7 is a schematic diagram of a structure of an airbag cover according to an embodiment of this application.

When the airbag cover 5 is specifically disposed, refer to FIG. 7. FIG. 7 is a schematic diagram of a structure of an airbag cover 5 according to an embodiment of this application. The airbag cover 5 may include a cover body 501, and a first snap fit 502 and a second snap fit 503 that are disposed on the cover body 501. The first snap fit 502 and the second snap fit 503 are respectively disposed at two opposite ends of the cover body 501. The first snap fit 502 is a mobile snap fit, and the second snap fit 503 is a fastening snap fit. The first snap fit 502 may move in a direction toward or away from the second snap fit 503. For example, the second snap fit 503 may be a protrusion structure disposed at an end of the cover body 501, and the second snap fit 503 is fastened to the end of the cover body 501.

Figure 8:
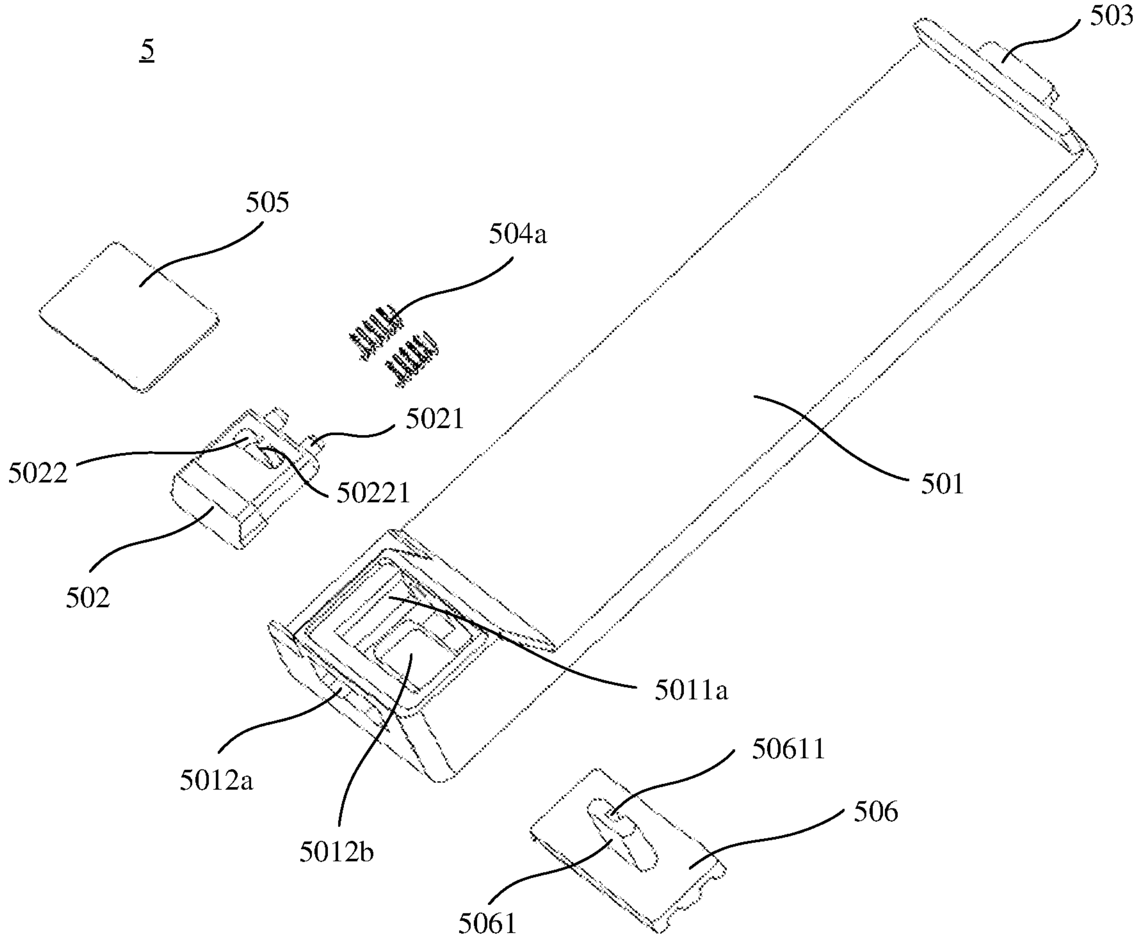
FIG. 8 is an exploded view of an airbag cover according to an embodiment of this application.

FIG. 8 shows a specific structure of a first snap fit 502 according to an embodiment of this application. In this embodiment of this application, a cover body 501 may be, but is not limited to, an integrally formed structure. In order to dispose the first snap fit 502 on the cover body 501, an accommodating cavity 5011*a* and an installation hole 5012*a* in communication with the accommodating cavity 5011*a* are disposed on the cover body 501. The installation hole 5012*a* is disposed on an end face that is of the cover body 501 and that is away from a second snap fit 503, the first snap fit 502 is accommodated in the accommodating cavity 5011*a*, and a part of the first snap fit 502 may extend from the installation hole 5012*a* to outside of the accommodating cavity 5011*a*. In a direction from the first snap fit 502 to the second snap fit 503, an elastic component 504*a* is disposed between the first snap fit 502 and a side wall of the accommodating cavity 5011*a*, and the elastic component 504*a* may elastically abut against the first snap fit 502 and the side wall of the accommodating cavity 5011*a* separately, so that the first snap fit 502 may move in a direction toward or away from the second snap fit 503 under elastic force of the elastic component 504*a*.

Still refer to FIG. 8. In an embodiment of this application, the elastic component 504*a* may be a spring, there may be one spring, and the spring may abut against a middle area of the first snap fit 502, so that the first snap fit 502 moves stably. In addition, there may be at least two springs, to further improve movement stability of the first snap fit 502. In addition, a limiting post 5021 may further be disposed on the first snap fit 502. In this way, the spring may be sleeved on the limiting post 5021, to prevent the spring from falling off, and the spring is reliably connected to the first snap fit 502.

In addition, an opening is disposed on a side that is of the accommodating cavity 5011*a* and that faces the watch body 1, to facilitate installation of the first snap fit 502 and the elastic component sod. An airbag cover 5 may further include a snap fit cover 505, where the snap fit cover 505 covers the opening, and may be, but is not limited to, fastened to the cover body 501 through bonding, snapping, snap-fitting, threaded connection, welding, or the like. In this way, structural stability of the airbag cover 5 can be improved, and appearance integrity of the airbag cover 5 can be improved.

In a possible embodiment, the snap fit cover 505 may further abut against the first snap fit 502, so that the snap fit cover 505 supports the first snap fit 502, thereby reducing shaking of the first snap fit 502 in a moving process. It may be understood that, an abutting force between the snap fit cover 505 and the first snap fit 502 is small, to avoid causing large resistance to movement of the first snap fit 502.

Refer to FIG. 7 and FIG. 8 together. The airbag cover 5 further includes a snap fastener 506, an installation hole 5012*b* is further disposed on a side that is of the cover body 501 and that is away from the watch body 1, and the installation hole 5012*b* communicates with the accommodating cavity 5011*a*. In addition, the first snap fit 502 is provided with a jack 5022, and a plug 5061 is disposed on the snap fastener 506. There may be one or at least two jacks 5022, and a quantity of plugs 5061 may be the same as a quantity of jacks 5022. The plug 5061 may be disposed on a surface that is of the snap fastener 506 and that faces the watch body 1. In this way, the snap fastener 506 may be installed on the airbag cover 5 through the installation hole 5012*b*, and the plug 5061 on the snap fastener 506 is inserted into the jack 5022 of the first snap fit 502. Refer to FIG. 7. In a direction from the first snap fit 502 to the second snap fit 503, the snap fastener 506 and a hole wall of the installation hole 5012*b* are in clearance fit, so that the snap fastener 506 can move in the installation hole 5012*b* in a direction toward to or away from the second snap fit 503. It may be understood that a size of a clearance between the snap fastener 506 and the hole wall of the installation hole 5012*b* may be specifically set based on a length of a part that is of the first snap fit 502 and that extends out of the accommodating cavity 5011. Still refer to FIG. 7. A surface that is of the snap fastener 506 and that is away from the watch body 1 is used as an operation surface of a finger of a user, and the surface may be disposed as an uneven surface, to increase friction between the finger and the snap fastener 506, thereby improving convenience of a user operation.

Refer to FIG. 8. A limiting protrusion 50221 may be further disposed on a side wall of the jack 5022, a limiting groove 50611 is disposed on the plug 5061 of the snap fastener 506, and the limiting protrusion 50221 and the limiting groove 50611 fit and are snap-fitted with each other, to implement limiting between the snap fastener 506 and the first snap fit 502. In some embodiments of this application, a limiting groove 50611 may be disposed in the jack 5022, and a limiting protrusion 50221 may be disposed on the plug 5061 of the snap fastener 506. In addition, the snap fastener 506 and the first snap fit 502 may be, but is not limited to, fastened through bonding, thread connection, or the like, to improve movement consistency between the snap fastener 506 and the first snap fit 502.

After the structure of the airbag cover 5 in the foregoing embodiment is understood, the following may describe fastening and disassembling processes of the airbag 2 and the watch body 1 with reference to FIG. 6 to FIG. 8.

First, a process in which the airbag 2 is fastened to the watch body 1 is described.

Step 1: Place a part that is of the airbag 2 and on which the air nozzle 201 is disposed in the installation slot 104 at an end of the watch body 1, and connect the air nozzle 201 to the air nozzle installation hole of the watch body 1.

Step 2: Snap fit the airbag cover 5 on the watch body 1 from a side that is of the airbag 2 and that is away from the watch body 1. During specific implementation, the second snap fit 503 of the airbag cover 5 may be first snap-fitted to one bayonet 1041 of the installation slot 104, and the snap fastener 506 is pushed in a direction from the first snap fit 502 to the second snap fit 503, so that the snap fastener 506 drives the first snap fit 502 to move toward the accommodating cavity 5011*a* of the airbag cover 5. In this case, the elastic component 504*a* is squeezed by the first snap fit 502 to shrink and store elastic force. Then, the airbag cover 5 is pressed to be accommodated in the installation slot 104 of the watch body 1. In this case, the snap fastener 506 may be released, the elastic component 504*a* releases the elastic force, and the first snap fastener 506 extends out of the installation hole 5012*a* of the accommodating cavity 5011*a* under an elastic action of the elastic component 504*a*, and is snap-fitted to the other bayonet 1041 of the installation slot 104, to implement the fastening connection between the airbag cover 5 and the watch body 1. In this case, the airbag 2 is located between the airbag cover 5 and the watch body 1. In this way, the airbag 2 may be crimped on the watch body 1 through the fastening connection between the airbag cover 5 and the watch body 1, to implement a reliable connection between the airbag 2 and the watch body 1.

It may be understood that steps of fastening the airbag 2 to the watch body 1 are only an example description provided in this application. In another possible embodiment of this application, a process of pushing the snap fastener 506 may be omitted, and instead, a large press force is applied to the airbag cover 5, to implement snap-fitting between the first snap fit 502 and the bayonet 1041 of the installation slot 104.

In this application, a process of disassembling the airbag 2 from the watch body 1 is simple. During specific implementation, the snap fastener 506 may be pushed in a direction from the first snap fit 502 to the second snap fit 503, so that the snap fastener 506 drives the first snap fit 502 to move toward the accommodating cavity 5011*a* of the airbag cover 5. In this case, the elastic component 504*a* is squeezed by the first snap fit 502 to shrink and store elastic force. Then, a first snap fit 502 side of the airbag cover 5 is lifted, and the first snap fit 502 is pulled out from the corresponding bayonet 1041. In this way, the airbag cover 5 can be disassembled. In this case, the airbag 2 may be easily disassembled from the air nozzle installation hole of the watch body 1.

In the foregoing embodiment of this application, a manner in which the airbag cover 5 is detachably connected to the watch body 1 is used, to implement a fastening connection and disassembly between the airbag 2 and the watch body 1, so that a structure is simple, and an operation is convenient. In this way, replacement and maintenance of the airbag 2 may be convenient. In addition, the user may replace the airbag 2 with another possible accessory based on a specific requirement of the user, to meet a wearing requirement of the user and improve user experience.

Figure 9:
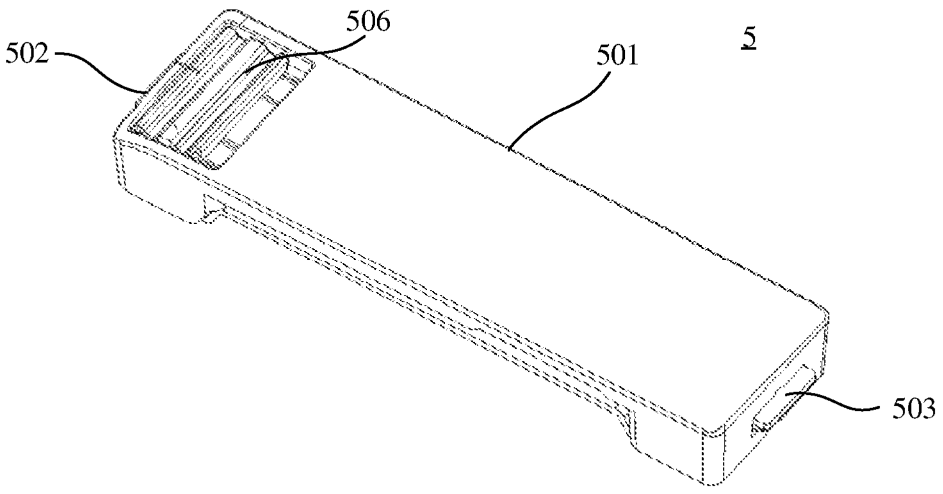
FIG. 9 is a schematic diagram of a structure of an airbag cover according to another embodiment of this application.

In the foregoing embodiment of this application, the airbag cover 5 is connected to the watch body 1 in a manner of snap-fitting the snap fit and the bayonet 1041. In a scenario in which a connection is performed through snap-fitting, in addition to the structure in the foregoing embodiment, the airbag cover 5 may be disposed in another possible manner. For example, refer to FIG. 9. FIG. 9 is a schematic diagram of a structure of an airbag cover 5 according to another possible embodiment of this application. It can be seen from FIG. 9 that an overall structure of the airbag cover 5 in this embodiment is similar to the structure of the airbag cover 5 in the foregoing embodiment, but a specific structure of the airbag cover 5 is different from that of the airbag cover 5 in the foregoing embodiment.

Figure 10:
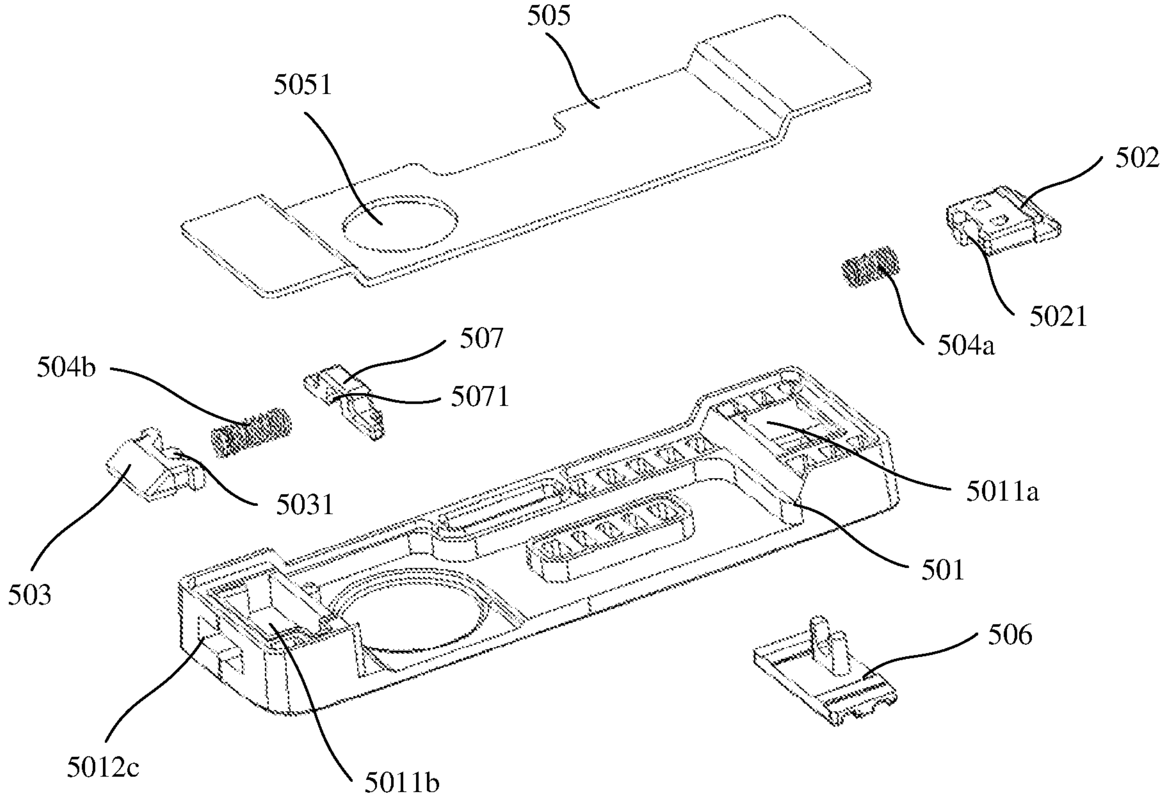
FIG. 10 is an exploded view of an airbag cover according to another embodiment of this application.

FIG. 10 is an exploded view of the airbag cover 5 shown in FIG. 9. In this embodiment, the airbag cover 5 includes a cover body 501, and a first snap fit 502 and a second snap fit 503 that are disposed on the cover body 501. The first snap fit 502 and the second snap fit 503 are disposed at two opposite ends of the cover body 501, and both the first snap fit 502 and the second snap fit 503 are mobile snap fits. Therefore, both the first snap fit 502 and the second snap fit 503 may move in a direction toward to or away from each other.

Still refer to FIG. 10. In order to dispose the first snap fit 502 and the second snap fit 503 on the cover body 501, an accommodating cavity 5011*a*, an accommodating cavity 5011*b*, an installation hole 5012*a* (not shown in FIG. 10, and reference may be made to FIG. 11) in communication with the accommodating cavity 5011*a*, and an installation hole 5012*c* in communication with the accommodating cavity 5011*b* are disposed on the cover body 501. The first snap fit 502 is accommodated in the accommodating cavity 5011*a*, and a part of the first snap fit 502 may extend from the installation hole 5012*a* to outside of the accommodating cavity 5011*a*. In a direction from the second snap fit 503 to the first snap fit 502, an elastic component 504*a* is disposed between the first snap fit 502 and a side wall of the accommodating cavity 5011*a*, and the elastic component 504*a* elastically abuts against the first snap fit 502 and the side wall of the accommodating cavity 5011*a* separately.

In some embodiments of this application, the elastic component 504*a* may be a spring, there may be one spring, and the spring may abut against a middle area of the first snap fit 502, so that the first snap fit 502 moves stably. In addition, there may be at least two springs, to further improve movement stability of the first snap fit 502. In addition, a limiting post 5021 may further be disposed on the first snap fit 502. In this way, the spring may be sleeved on the limiting post 5021, to prevent the spring from falling off, and the spring is reliably connected to the first snap fit 502.

Figure 11:
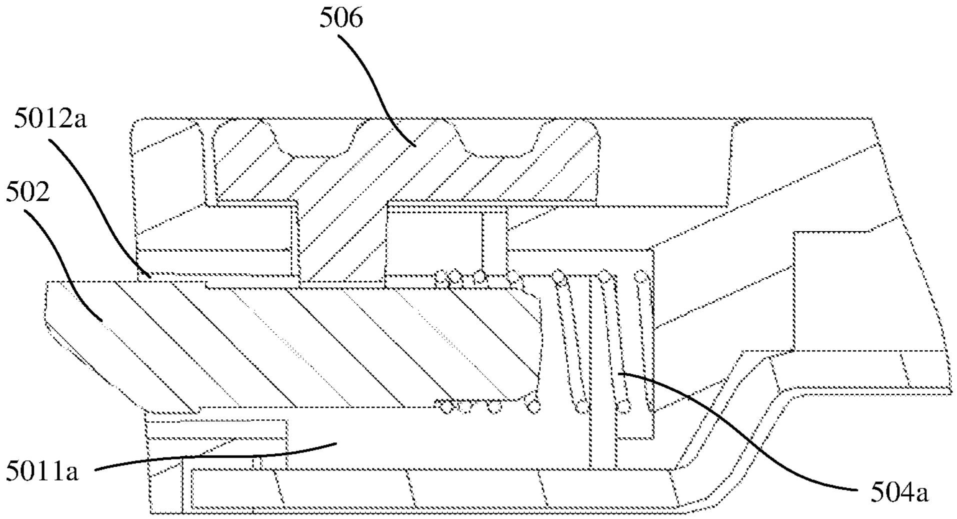
FIG. 11 is a schematic diagram of a local structure of an airbag cover according to an embodiment of this application.

Refer to FIG. 10 and FIG. 11 together. In this embodiment of this application, the airbag cover 5 may further include a snap fastener 506. A specific structure of the snap fastener 506, and a connection manner of the snap fastener 506, the first snap fit 502, and the cover body 501 are similar to those in the foregoing embodiment, and may be disposed with reference to the foregoing embodiment. Details are not described herein again.

Figure 12:
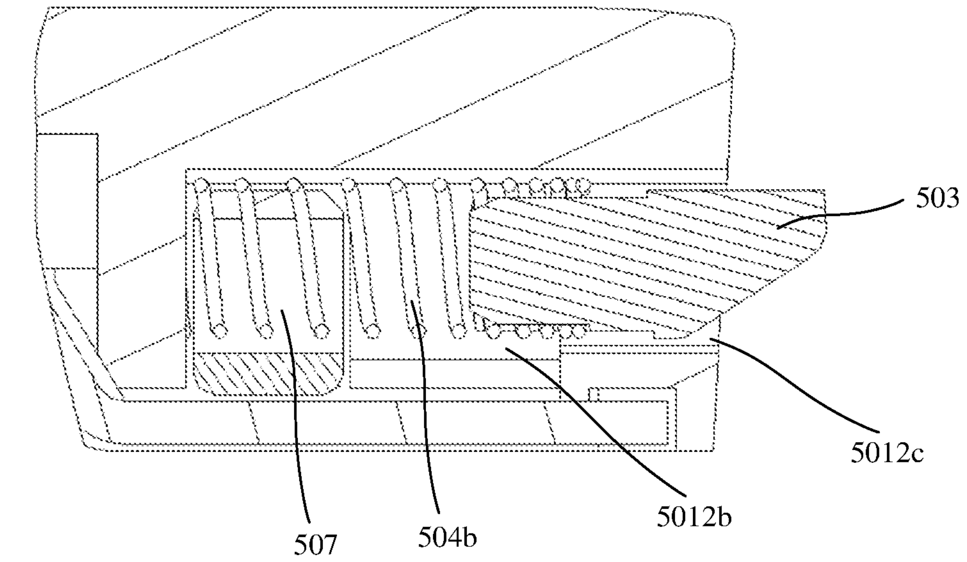
FIG. 12 is a schematic diagram of a local structure of an airbag cover according to another embodiment of this application.

Refer to FIG. 10 and FIG. 12. The second snap fit 503 is accommodated in the accommodating cavity 5011*b*, and a part of the second snap fit 503 may extend from the installation hole 5012*c* to outside of the accommodating cavity 5011*b*. In a direction from the first snap fit 502 to the second snap fit 503, an elastic component 504*b* is disposed between the second snap fit 503 and a side wall of the accommodating cavity 5011*b*, and the elastic component 504*b* elastically abuts against the second snap fit 503 and the side wall of the accommodating cavity 5011*b* separately. The elastic component 5041, may be a spring, and there may be one spring. The spring may abut against a middle area of the second snap fit 503, so that the second snap fit 503 moves stably. In addition, there may be at least two springs, to further improve movement stability of the second snap fit 503. In addition, a limiting post 5031 may further be disposed on the second snap fit 503. In this way, the spring may be sleeved on the limiting post 5031, to prevent the spring from falling off, and the spring is reliably connected to the second snap fit 503.

Still refer to FIG. 10 and FIG. 12. In a possible embodiment of this application, the elastic component 504*b* may be further fastened to the accommodating cavity 5011 by using a fastening block 507. Refer to FIG. 10. The fastening block 507 has a limiting hole 5071, the elastic component 504 may penetrate the limiting hole 5071, and the fastening block 507 is fastened to the accommodating cavity 5011*b*, so that the elastic component 504*b* is limited to the accommodating cavity 5011*b*, to improve movement stability of the elastic component 504*b*.

Figure 13:
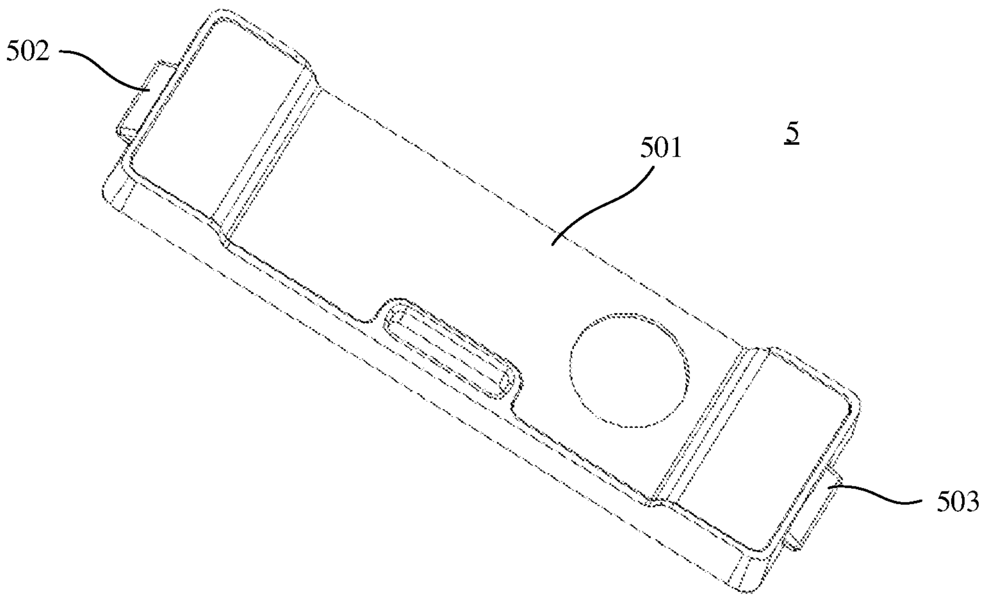
FIG. 13 is a schematic diagram of a structure of an airbag cover according to another embodiment of this application.

Still refer to FIG. 10. In this embodiment of this application, each of the accommodating cavity 5011*a* and the accommodating cavity 5011*b* may have an opening on a side that faces the watch body 1. This facilitates installation of the first snap fit 502 and the second snap fit 503. In addition, the airbag cover 5 may further include a snap fit cover 505. There may be two snap fit covers 505, and the two snap fit covers 505 are disposed independently, and cover openings of the accommodating cavity 5011*a* and the accommodating cavity 5011*b* respectively. In some other embodiments of this application, refer to FIG. 10 and FIG. 13 together. The snap fit cover 505 may alternatively be an integrally formed structure, and the snap fit cover 505 covers the two openings at the same time, thereby helping simplify the structure of the airbag cover 5. No matter how the snap fit cover 505 is disposed, the snap fit cover 505 may be, but is not limited to, fastened to the cover body 501 through bonding, thread connection, welding, or the like. By disposing the snap fit cover 505, structural stability of the airbag cover 5 can be improved, and appearance integrity of the airbag cover 5 can be improved.

In a possible embodiment, the snap fit cover 505 may further abut against the first snap fit 502 and the second snap fit 503, so that the snap fit cover 505 supports the first snap fit 502 and the second snap fit 503, thereby reducing shaking of the first snap fit 502 and the second snap fit 503 in a moving process. It may be understood that, abutting forces between the snap fit cover 505 and the first snap fit 502 and the second snap fit 503 are small, to avoid causing large resistance to movement of the first snap fit 502 and the second snap fit 503.

After the structure of the airbag cover 5 is understood, the following describes fastening and disassembling processes of the airbag 2 and the watch body 1.

Figure 14:
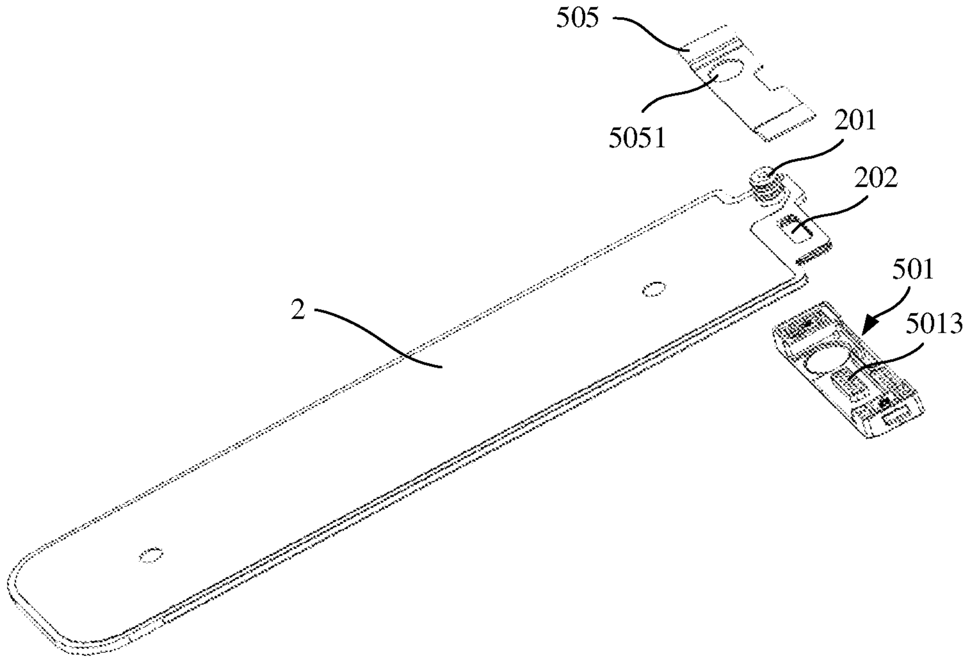
FIG. 14 is a schematic diagram of an assembly process of an airbag cover and an airbag according to an embodiment of this application.

FIG. 14 shows a process in which an airbag cover 5 is fastened to an airbag 2 according to a possible embodiment of this application. The airbag cover 5 includes a cover body 501 and a snap fit cover 505 of an integrally formed structure, and an avoidance opening 5051 for an air nozzle 201 of the airbag 2 to extend out is disposed on the snap fit cover 505. When the airbag cover 5 of this structure is used to connect the airbag 2 to a watch body 1, the airbag 2 may be first fastened to the airbag cover 5. During specific implementation, a part (which may be understood as a part that is of the airbag 2 and that connects to the watch body 1) that is of the airbag 2 and on which the air nozzle 201 is disposed may be placed between the cover body 501 and the snap fit cover 505, and the air nozzle 201 extends out of the avoidance opening 5051 of the snap fit cover 505. Then, the snap fit cover 505 and the cover body 501 are fastened to obtain a structure shown in FIG. 15. In addition, still refer to FIG. 14. In this embodiment of this application, a limiting block 5013 may be further disposed on the cover body 501, and the part that is of the airbag 2 and that connects to the watch body 1 is provided with a limiting opening 202, so that the limiting block 5013 is inserted into the limiting opening 202 to limit the airbag 2 on the cover body 501, and reliability of a connection between the airbag 2 and the airbag cover 5 can be improved.

Figure 15:
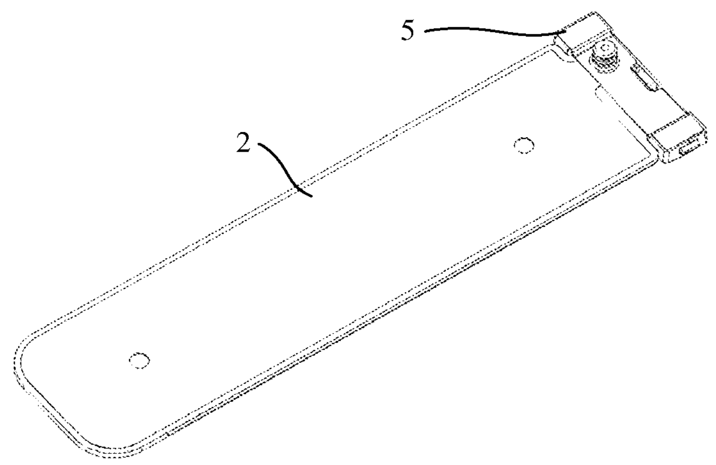
FIG. 15 is a schematic diagram of an assembly structure of an airbag cover and an airbag according to an embodiment of this application.

Then, the structure that is obtained after the airbag 2 is connected to the airbag cover 5 and that is shown in FIG. 15 is fastened to the watch body 1. During specific implementation, a structure of the watch body 1 may be disposed with reference to the embodiment shown in FIG. 6. The airbag cover 5 may be snap fitted in the installation slot 104 of the watch body 1, and may apply a press force to the airbag cover 5 with reference to FIG. 11 and FIG. 12 together, so that the first snap fit 502 moves toward the accommodating cavity 5011*a* of the airbag cover 5, the second snap fit 503 moves toward the accommodating cavity 5011*b* of the airbag cover 5, the elastic component 504*a* is squeezed by the first snap fit 502 to shrink and store elastic force, and the elastic component 504*b* is squeezed by the second snap fit 503 to shrink and store elastic force. When the airbag cover 5 is pressed until the first snap fit 502 and the second snap fit 503 are opposite to bayonets 1041 on corresponding sides of the installation slots 104 of the watch body 1, the first snap fit 502 extends from the installation hole 5012*a* of the accommodating cavity 5011*a* under an elastic action of the elastic component 504*a*, and is snap-fitted to the bayonet 1041 of the installation slot 104. The second snap fit 503 extends from the installation hole 5012*c* of the accommodating cavity 5011*b* under an elastic action of the elastic component 504*b*, and is snap-fitted to the bayonet 1041 of the installation slot 104, thereby implementing the fastening connection between the airbag cover 5 and the watch body 1. In addition, it may be understood that, in the foregoing process, before the press force is applied to the airbag cover 5, the air nozzle 201 of the airbag 2 may be inserted into the air nozzle installation hole of the watch body 1.

It may be understood that steps of fastening the airbag 2 to the watch body 1 are only an example description provided in this application. In another possible embodiment of this application, the second snap fit 503 may be first snap-fitted to one of the bayonets 1041 in the installation slot 104, and then the snap fastener 506 is pushed to snap-fit the first snap fit 503 to the bayonet 1041 in the installation slot 104, to reduce wear of the snap fit and the bayonet.

In this application, a process of disassembling the airbag 2 from the watch body 1 is simple. During specific implementation, refer to FIG. 10 and FIG. 1*i*. The snap fastener 506 may be pushed in a direction from the first snap fit 502 to the second snap fit 503, so that the snap fastener 506 drives the first snap fit 502 to move toward the accommodating cavity 5011*a* of the airbag cover 5. In this case, the elastic component 504*a* is squeezed by the first snap fit 502 to shrink and store elastic force. Then, a second snap fit 503 side of the airbag cover 5 is lifted, and the second snap fit 503 is pulled out from the corresponding bayonet 1041. In this way, the airbag cover 5 can be disassembled. In this case, the airbag 2 may be easily disassembled from the air nozzle installation hole of the watch body 1.

This manner of disposing the airbag cover 5 in this embodiment of this application can maintain appearance integrity and aesthetics of the airbag cover 5, and can further effectively avoid damage caused by partial pulling of the airbag 2 and the air nozzle 201 in installation and disassembly processes, thereby prolonging a service life of the airbag 2 and the air nozzle 201. In this embodiment of this application, a manner in which the airbag cover 5 is detachably connected to the watch body 1 is used, to implement a fastening connection and disassembly between the airbag 2 and the watch body 1, so that a structure is simple, and an operation is convenient. In this way, replacement and maintenance of the airbag 2 may be convenient. In addition, the user may replace the airbag 2 with another possible accessory based on a specific requirement of the user, to meet a wearing requirement of the user and improve user experience.

In addition, in a possible embodiment of this application, when snap fit covers 505 are two independent structures that respectively cover the openings of the accommodating cavity 5011*a* and the accommodating cavity 5011*b*, the airbag 2 may be crimped on the watch body 1 through the connection between the airbag cover 5 and the watch body 1. For a specific disposition manner, refer to the foregoing embodiment. Details are not described herein again.

Figure 16:
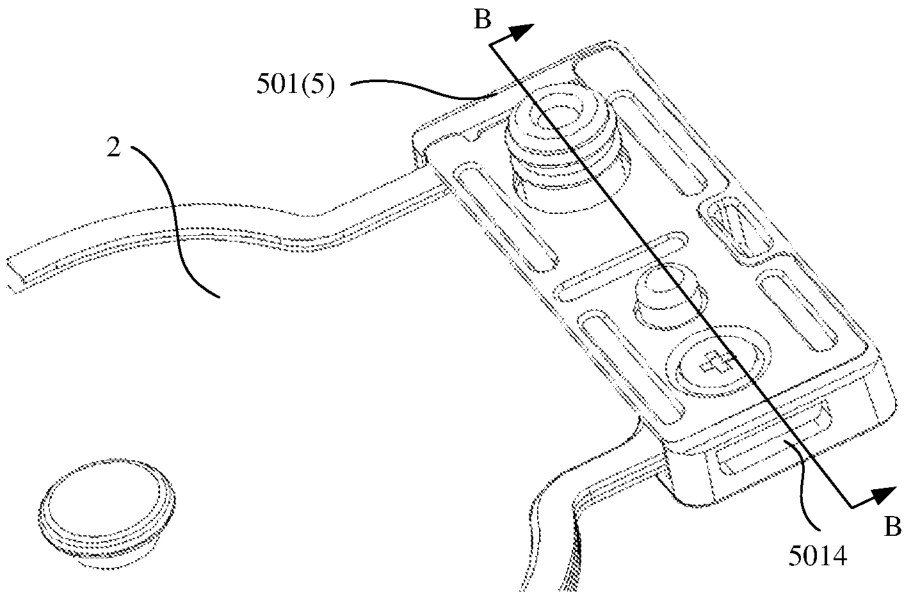
FIG. 16 is a schematic diagram of an assembly structure of an airbag cover and an airbag according to another embodiment of this application.

In the foregoing embodiments of this application, a snap fit is disposed on the airbag cover 5, and bayonets are disposed on the watch body 1, so that a detachable connection between the airbag cover 5 and the watch body 1 is implemented through snap-fitting of the snap fit and the bayonet. However, in some possible embodiments of this application, a detachable connection between the watch body 1 and the airbag cover 5 may be implemented by disposing the snap fit on the watch body 1 and disposing the bayonet on the airbag cover 5. During specific implementation, first refer to FIG. 16. FIG. 16 is a schematic diagram of an assembly structure of an airbag cover 5 and an airbag 2 according to another possible embodiment of this application. In this embodiment, the airbag cover 5 may include a cover body 501. The cover body 501 has a third bayonet 5014 and a fourth bayonet (not shown in FIG. 16). The third bayonet 5014 and the fourth bayonet are respectively disposed at two oppositely disposed ends of the cover body 501.

Figure 17:
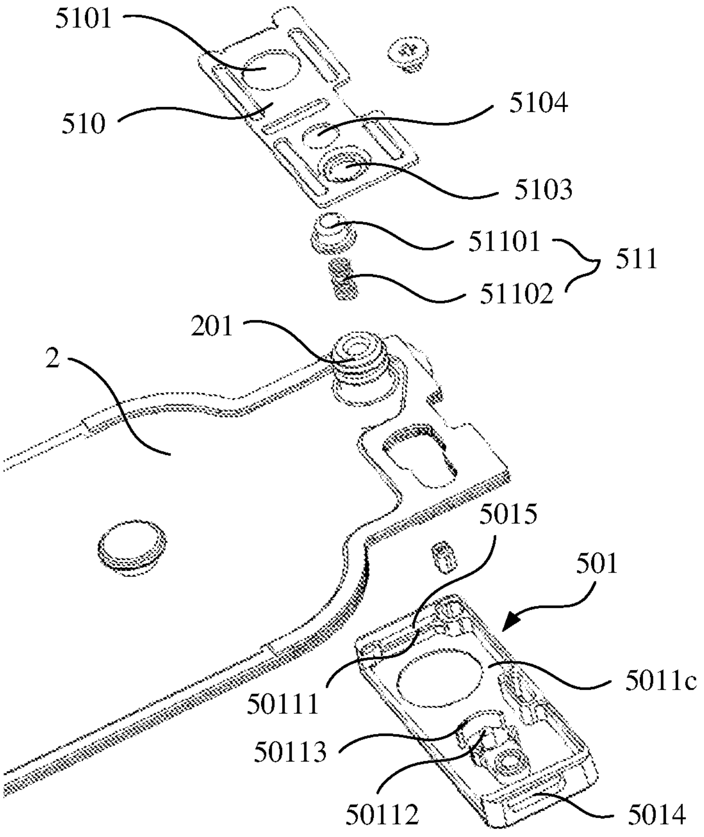
FIG. 17 is an exploded view of an assembly structure of an airbag cover and an airbag according to another embodiment of this application.

FIG. 17 shows an exploded view of the airbag cover 5. An accommodating cavity 5011*c* is disposed on the cover body 501. The accommodating cavity 5011*c* is located between the third bayonet 5014 and the fourth bayonet 5015, and an end that is of an airbag 2 and on which an air nozzle 201 is disposed may be accommodated in the accommodating cavity 5011*c*. In addition, in order to fasten the airbag 2 to the airbag cover 5, the airbag cover 5 may further include a pressing plate 510, and the pressing plate 510 may be fastened to the cover body 501. In this way, the end that is of the airbag 2 and on which the air nozzle 201 is disposed may be located between the cover body 501 and the pressing plate 510, and the airbag 2 is fastened to the airbag cover 5 through a fastening connection between the pressing plate 510 and the cover body 501. It should be noted that in this application, a tensile fabric layer may further be disposed on a part that is of the airbag 2 and that connects to the airbag cover 5. The tensile fabric layer may be formed through, but is not limited to, hot melting, and therefore can effectively reduce pulling effect on the airbag 2 in an installation or disassembly process of the airbag cover 5 and the watch body 1, to protect the airbag 2.

Figure 18:
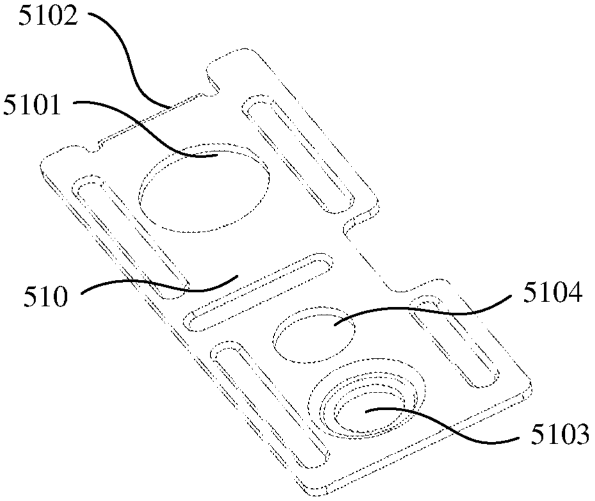
FIG. 18 is a schematic diagram of a structure of a pressing plate according to an embodiment of this application.
Figure 19A:
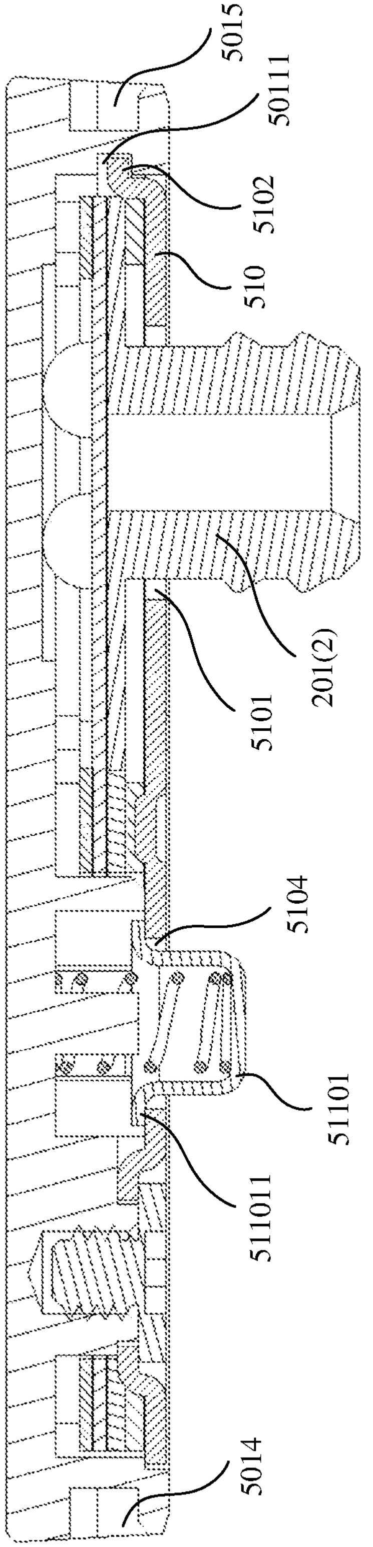
FIG. 19*a* and FIG. 19*b* are B-B sectional views of the structure shown in FIG. 16.

When the pressing plate 510 is specifically disposed, refer to FIG. 18. FIG. 18 is a schematic diagram of a structure of the pressing plate 510 according to a possible embodiment of this application. It can be understood that, after the airbag 2 shown in FIG. 17 is installed on the airbag cover 5, the air nozzle 201 of the airbag 2 also needs to be exposed from the airbag cover 5. Based on this, refer to FIG. 19*a*. FIG. 19*a* is a B-B sectional view of the structure shown in FIG. 16. Refer to FIG. 18 and FIG. 19*a* together. In this application, an air nozzle hole 5101 may be disposed on the pressing plate 510, so that the air nozzle 201 of the airbag 2 may extend out from the air nozzle hole 5101, thereby facilitating a connection between the air nozzle 201 and the watch body 1. It should be noted that, in this embodiment of this application, the air nozzle 201 of the airbag 2 may be an integrally formed structure shown in FIG. 19*a*, and a protrusion structure may be disposed on a surface of the air nozzle 201. In this way, when the air nozzle 201 is installed on the watch body 1, the protrusion structure may have a sealing function between the air nozzle 201 and the watch body 1, and can improve air tightness of a joint between the airbag 2 and the watch body 1, thereby helping improve accuracy of blood pressure measurement. In addition, the air nozzle 201 of the airbag 2 may alternatively be designed with reference to a structure shown in FIG. 19*b*. A ring groove structure may alternatively be disposed on a surface of the air nozzle 201, and a seal ring 2011 may be further disposed in the ring groove structure, to seal the air nozzle 201. In this way, when the air nozzle 201 is inserted into the watch body 1, air tightness of a joint between the airbag 2 and the watch body 1 can be improved, thereby helping improve accuracy of blood pressure measurement.

In addition, to implement a fastening connection between the pressing plate 510 and the cover body 501, a snap-fitting part 5102 may be disposed at a first end of the pressing plate 510, and the first end may be an end that is of the pressing plate 510 and that faces the fourth bayonet 5015. Refer to FIG. 17 and FIG. 18 together. A side wall at a corresponding location of the accommodating cavity 5011*c* of the cover body 501 may be provided with a snap-fitting slot 50111, and the snap-fitting part 5102 of the pressing plate 510 may be inserted into the snap-fitting slot 50111 of the cover body 501, to limit implement limiting of the pressing plate 510 on the cover body 501.

In this application, a manner of fastening the pressing plate 510 and the cover body 501 is not limited. For example, the pressing plate 510 and the cover body 501 may be connected in a manner in which a screw is tightly screwed. During specific implementation, still refer to FIG. 17 and FIG. 18. A screw hole 5103 may further be disposed on the pressing plate 510, and the screw hole 5103 may be disposed at a location close to a second end of the pressing plate 510. The first end and the second end of the pressing plate 510 are disposed opposite to each other. In this way, when the pressing plate 510 is installed on the cover body 501, the snap-fitting part 5102 at the first end may be first inserted into the snap-fitting slot 50111 of the accommodating cavity 5011*c* of the cover body 501, and then a fastening connection between the pressing plate 510 and the cover body 501 is implemented by screwing a screw installed into the screw hole 5103 of the pressing plate 510 tightly.

In addition to the foregoing structure, the airbag cover 5 may further include an elastic protrusion 511. The elastic protrusion 511 may be disposed at the accommodating cavity 5011*c* of the cover body 501, and may move in a direction toward or away from the accommodating cavity 5011*c*. Still refer to FIG. 17. When the elastic protrusion 511 is specifically disposed, the elastic protrusion 511 may include a protrusion cover 51101 and an elastic component 51102, the elastic component 51102 may be located between the protrusion cover 51101 and a bottom wall of the accommodating cavity 5011*c*, and the elastic component 51102 may elastically abut against the bottom wall of the accommodating cavity 5011*c* and the protrusion cover 51101 separately. In this application, the elastic component 51102 may be a spring. In order to improve reliability of movement of the elastic component 51102, a limiting post 50112 may be disposed on the bottom wall of the accommodating cavity 5011*c* of the cover body 501. In this way, the elastic component 51102 may be sleeved on the limiting post 50112, thereby avoiding falling off of the elastic component 51102 and improving movement stability of the protrusion cover 51101.

In addition, a guiding structure 50113 may be further disposed on the bottom wall of the accommodating cavity 5011*c* of the cover body 501, and the protrusion cover 51101 may be in contact with the guiding structure 50113, so that the guiding structure 50113 guides movement of the protrusion cover 51101. Still refer to FIG. 17. When the guiding structure 50113 is specifically disposed, the guiding structure 50113 may be disposed on a peripheral side of the limiting post 50112. In a possible embodiment of this application, the guiding structure 50113 may be an annular or semi-annular structure disposed around the limiting post 50112. In this way, the protrusion cover 51101 may be accommodated in an area formed around the limiting post 50112 by the guiding structure 50113, and an outer edge of the protrusion cover 51101 may be in contact with a side wall that is of the guiding structure 50113 and that faces the limiting post 50112, so that the guiding structure 50113 plays an effective and reliable guiding role for the movement of the protrusion cover 51101.

Refer to FIG. 17 and FIG. 18. The pressing plate 510 may be further provided with a protrusion cover hole 5104, and the protrusion cover 51101 may extend from the protrusion cover hole 5104 to a side that is of the pressing plate 510 and that is away from the cover body 501. In addition, it should be noted that, because an end that is of the airbag 2 and on which the air nozzle 201 is disposed is located between the pressing plate 510 and the cover body 501, in order to facilitate the protrusion cover 51101 in extending out from the protrusion cover hole 5104, a through hole may be disposed at a location corresponding to the protrusion cover hole 5104 of the airbag 2, to avoid interference caused by the airbag to the movement of the protrusion cover 51101, so that the protrusion cover 51101 may extend from the protrusion cover hole 5104 of the pressing plate 510 through the through hole of the airbag 2.

Figure 19B:
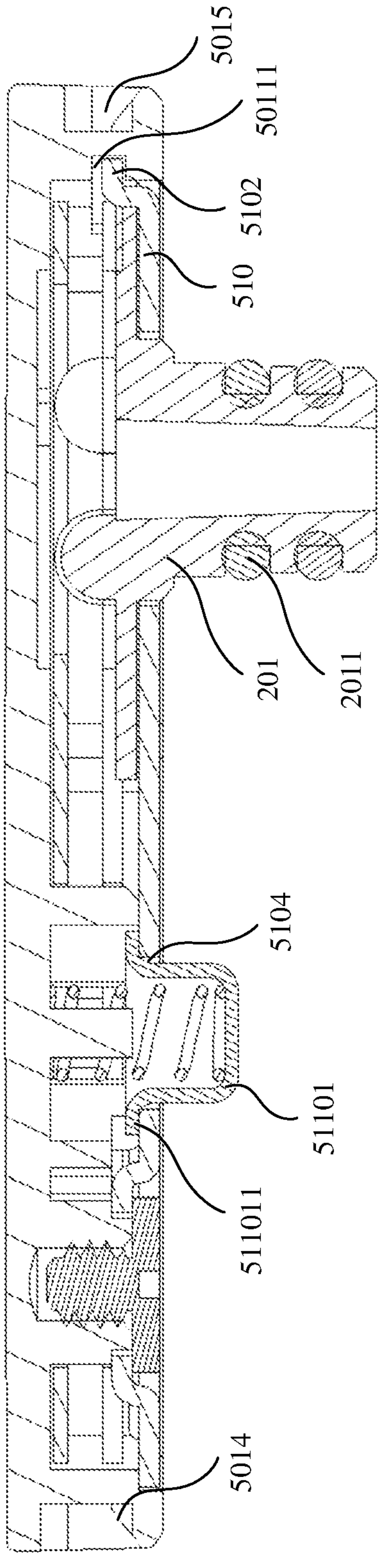

Refer to FIG. 19*a* and FIG. 19*b*. In this application, to prevent the protrusion cover 51101 from falling off from the pressing plate 510, a flange structure 511011 may be formed at a cover edge of the protrusion cover 51101, and a diameter of the flange structure 511011 is greater than a diameter of the protrusion cover hole 5104, so that the pressing plate 510 limits the protrusion cover 51101.

Figure 20A:
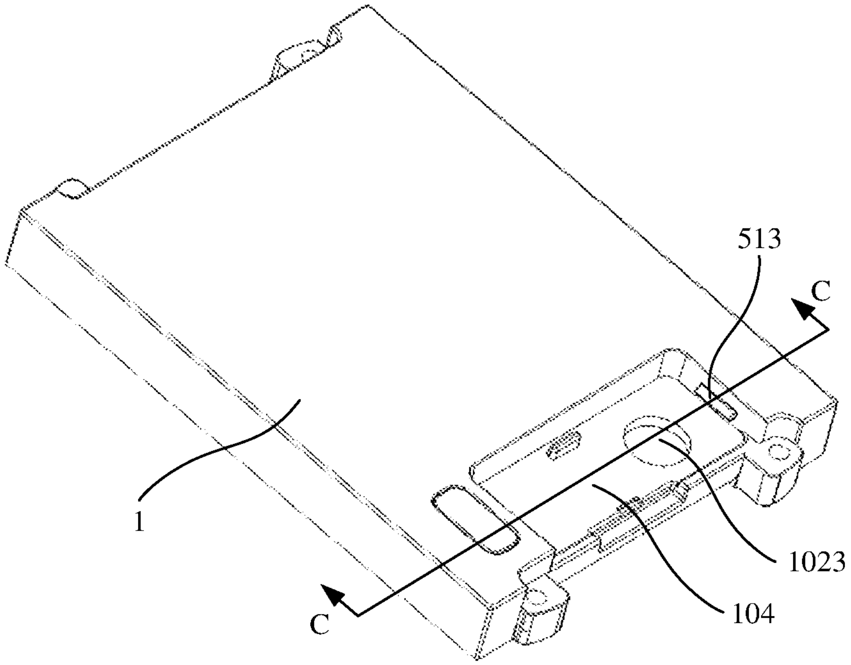

In this embodiment of this application, to implement a detachable connection between the airbag cover 5 and the watch body 1, when the watch body 1 is specifically disposed, refer to FIG. 20*a* and FIG. 10*b*. FIG. 20*a* and FIG. 10*b* are schematic diagrams of a structure of a watch body 1 at two different angles. An end of the watch body 1 may be provided with an installation slot 104, and the installation slot 104 is disposed on a bottom surface of the watch body 1. In addition, an air nozzle installation hole 1023 is disposed in the installation slot 104, the airbag cover 5 may be installed in the installation slot 104, and an air nozzle 201 of an airbag 2 may be inserted into the air nozzle installation hole 1023.

In addition, one snap fit may be disposed on each of two oppositely disposed side walls of the installation slot 104, and the snap fits are respectively denoted as a third snap fit 512 and a fourth snap fit 513. The third snap fit 512 and the fourth snap fit 513 may separately move toward or away from each other.

Figure 20B:
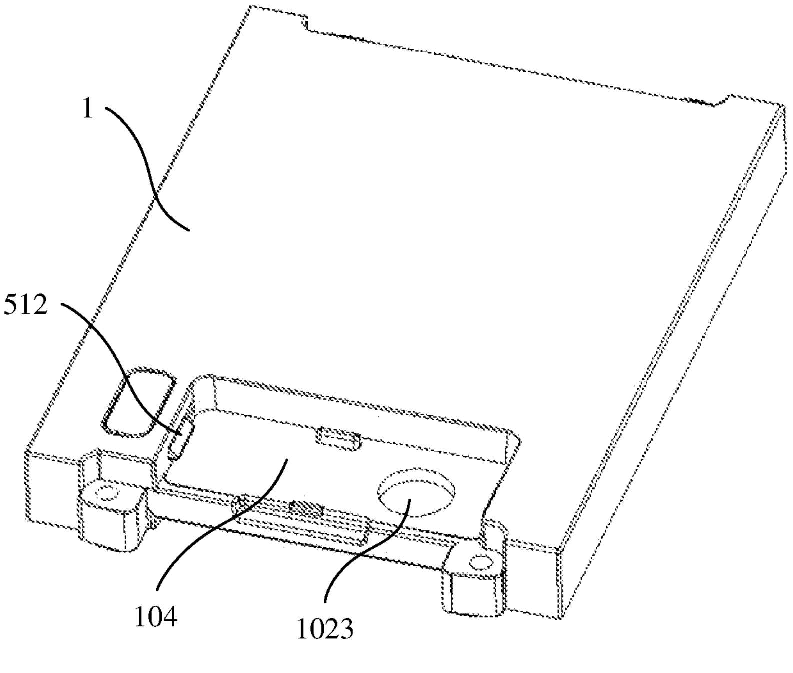
Figure 21:
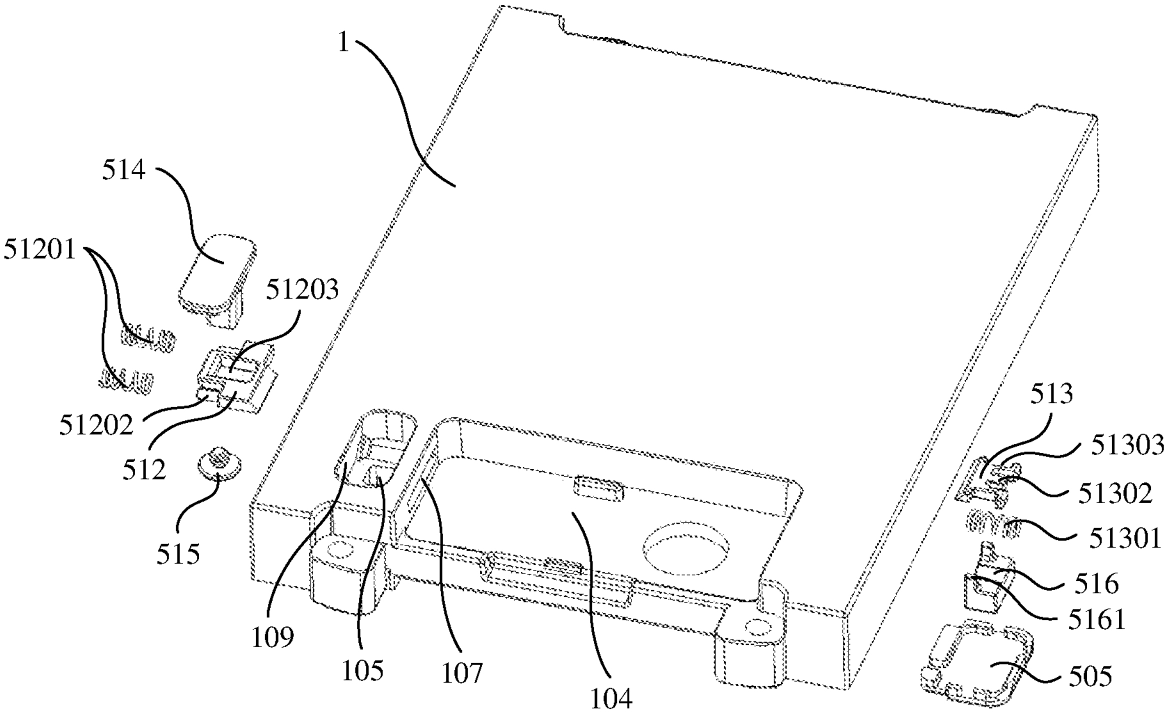
FIG. 21 is an exploded view of a watch body according to an embodiment of this application.

FIG. 21 is an exploded view of the watch body 1 shown in FIG. 20*a* and FIG. 20*b*. FIG. 21 shows a specific manner of disposing the third snap fit 512 and the fourth snap fit 513 on the watch body 1 in a possible embodiment of this application. A first accommodating slot 105 and a second accommodating slot (not shown in FIG. 21) are disposed on the watch body 1. The first accommodating slot 105 communicates with the installation slot 104 through a first through hole 107, and the second accommodating slot 106 communicates with the installation slot 104 through a second through hole (not shown in FIG. 21).

Figure 22:
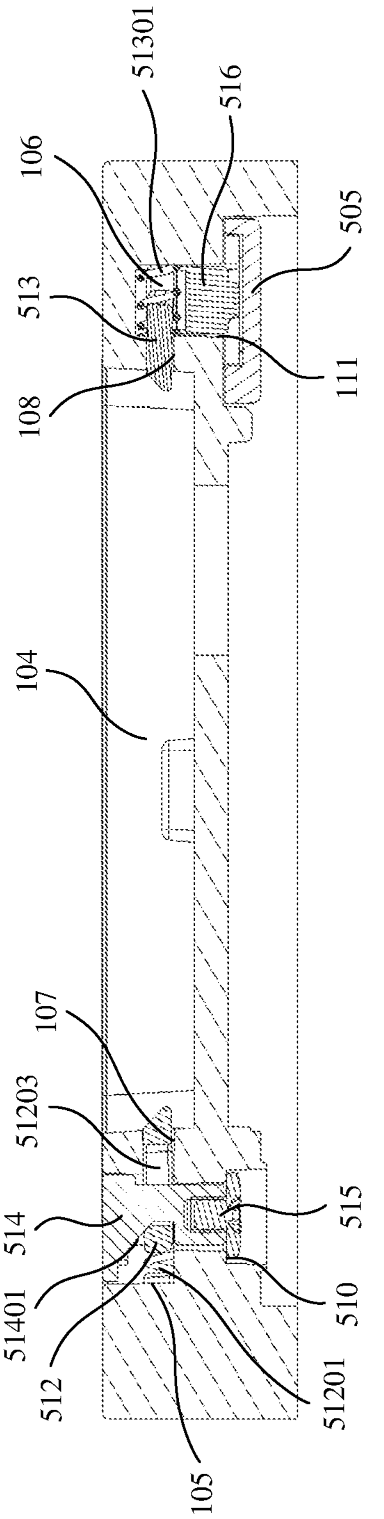
FIG. 22 is a C-C sectional view of the watch body shown in FIG. 20*a;*

FIG. 22 is a C-C sectional view of the watch body 1 shown in FIG. 20*a*. The third snap fit 512 may be accommodated in the first accommodating slot 105, and a part of the third snap fit 512 may extend from the first through hole 107 to the installation slot 104. An elastic component 51201 is disposed between the third snap fit 512 and a side wall of the first accommodating slot 105. The elastic component 51201 may be disposed on a side that is of the third snap fit 512 and that is away from the fourth snap fit 513, and the elastic component 51201 elastically abuts against the third snap fit 512 and the side wall of the first accommodating slot 105 separately.

In some embodiments of this application, the elastic component 51201 may be a spring, there may be one spring, and the spring may abut against a middle area of the third snap fit 512, so that the third snap fit 512 moves stably. In addition, there may be at least two springs, to further improve movement stability of the third snap fit 512. In addition, refer to FIG. 21. A limiting post 51202 may further be disposed on the third snap fit 512. In this way, the spring may be sleeved on the limiting post 51202, to prevent the spring from falling off, and the spring is reliably connected to the third snap fit 512.

Refer to FIG. 21 and FIG. 22 together. In this embodiment of this application, a snap fit button 514 may further be disposed on the watch body 1. In addition, the bottom surface of the watch body 1 is further provided with a third through hole 109, and the third through hole 109 communicates with the first accommodating slot 105. The snap fit button 514 may be installed in the third through hole 109, and the snap fit button 514 may move in an axis direction of the third through hole 109. The third snap fit 512 has an opening 51203, and the opening 51203 may be a through hole. In this case, the snap fit button 514 may pass through the opening 51203 of the third snap fit 512.

In a possible embodiment of this application, the snap fit button 514 may be limited to the watch body 1 by using a limiting component 515, so that the snap fit button 514 can move in an axis direction of the third watch body 1, and the snap fit button 514 can be prevented from falling off from the watch body 1. Refer to FIG. 21 and FIG. 22 together. The limiting component 515 may be a screw, the third snap fit 512 may be located between the third through hole 109 and the screw, and the screw and the snap fit button 514 are in a screwing connection. In addition, refer to FIG. 22. A step surface 510 may be disposed on the watch body 1. In a movement process of the snap fit button 514, an edge of a screw cap of a screw may be snap-fitted with the step surface 510, so that the step surface 510 can limit movement of the snap fit button 514. It should be noted that, because the snap fit button 514 penetrates through the opening 51203 of the third snap fit 512, when the movement of the snap fit button 514 is limited, movement of the third snap fit 512 may also be limited.

In addition, in a movement process of the snap fit button 514, the third snap fit 512 may be driven to move in a direction toward or away from the first accommodating slot 105. During specific implementation, still refer to FIG. 22. The snap fit button 514 further has an inclined surface 51401. The inclined surface 51401 may abut against a part that is of the third snap fit 512 and that is away from the installation slot 104, so that when the snap fit button 514 moves along the third through hole 109, the inclined surface 51401 can push the third snap fit 512 to move toward the first accommodating slot 105. It may be understood that an inclination direction of the inclined surface 51401 may be designed based on a relationship between a movement direction of the snap fit button 514 and a movement direction of the third snap fit 512. For example, when the snap fit button 514 is pressed, the inclined surface 51401 may be enabled to push the third snap fit 512 to move toward the first accommodating slot 105; and when the snap fit button 514 is released, the third snap fit 512 may move in a direction away from the first accommodating slot 105 under elastic force of the elastic component 51201. In addition, an inclination angle of the inclined surface 51401 may be designed based on a proportional relationship between a movement distance of the snap fit button 514 and a movement distance of the third snap fit 512.

Still refer to FIG. 21 and FIG. 22. The fourth snap fit 513 may be accommodated in a second accommodating slot 106, and a part of the fourth snap fit 513 may extend from the second through hole 108 to the installation slot 104. An elastic component 51301 is disposed between the fourth snap fit 513 and a side wall of the second accommodating slot 106. The elastic component 51301 may be disposed on a side that is of the fourth snap fit 513 and that is away from the third snap fit 512, and the elastic component 51301 elastically abuts against the fourth snap fit 513 and the side wall of the second accommodating slot 106 separately.

In some embodiments of this application, the elastic component 51301 may be a spring, there may be one spring, and the spring may abut against a middle area of the fourth snap fit 513, so that the fourth snap fit 513 moves stably. In addition, there may be at least two springs, to further improve movement stability of the fourth snap fit 513. In addition, refer to FIG. 21. A limiting post 51302 may further be disposed on the fourth snap fit 513. In this way, the spring may be sleeved on the limiting post 51302, to prevent the spring from falling off, so that the spring is reliably connected to the fourth snap fit 513.

Figure 23:
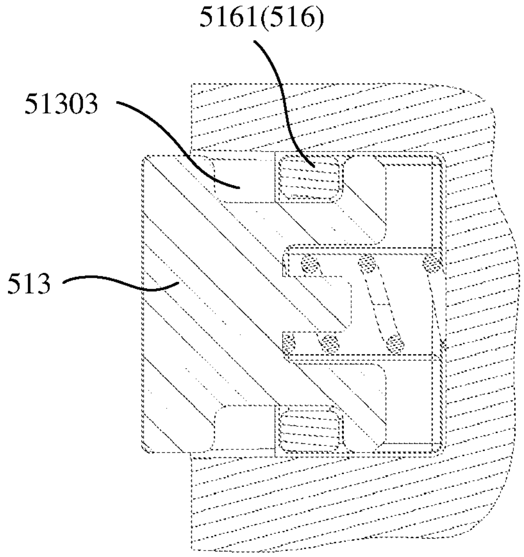
FIG. 23 is a top view of an assembly structure of a snap fit support and a fourth snap fit according to an embodiment of this application.

In this application, to limit movement of the fourth snap fit 513, a snap fit support 516 may be disposed on the watch body 1 for the fourth snap fit 513. Still refer to FIG. 21 and FIG. 22. A fourth through hole 111 is further disposed on the watch body 1, the fourth through hole in communicates with the second accommodating slot 106, and an opening direction of the fourth through hole in may be opposite to an opening direction of the installation slot 104. The snap fit support 516 may be installed in the fourth through hole in, and supports the fourth snap fit 513. In addition, the snap fit support 516 may be provided with a protrusion 5161, and the fourth snap fit 513 may be provided with a recess 51303. FIG. 23 is a top view of an assembly structure of the snap fit support 516 and the fourth snap fit 513. After the snap fit support 516 and the fourth snap fit 513 are assembled, the protrusion 5161 of the snap fit support 516 may be inserted into the recess 51303 of the fourth snap fit 513, and in a movement direction of the fourth snap fit 513, the protrusion 5161 and a side wall of the recess 51303 are in clearance fit. It may be understood that a clearance between the protrusion 5161 and the side wall of the recess 51303 may be disposed based on a movement distance of the fourth snap fit 513 in the second accommodating slot 106, and a length of the fourth snap fit 513 that can extend into the installation slot 104. In addition, in some possible embodiments of this application, the protrusion 5161 may alternatively be disposed on the fourth snap fit 513, and the recess 51303 may be disposed on the snap fit support 516.

In addition, to prevent the snap fit support 516 from falling off from the watch body 1, still refer to FIG. 21 and FIG. 22. The watch body 1 may further be provided with a snap fit cover 505, the snap fit support 516 is located between the fourth snap fit 513 and the snap fit cover 505, and the snap fit cover 505 abuts against the snap fit support 516, so that the snap fit cover 505 can support the snap fit support 516. In addition, the snap fit cover 505 and the watch body 1 may be, but is not limited to, fastened through bonding, thread connection, or the like, so that the snap fit cover 505 supports the snap fit support 516 more reliably.

After the structures of the airbag cover 5 and the watch body 1 in this embodiment of this application are understood, the following describes installation and disassembling processes of the watch body 1 and the airbag cover 5 assembled with the airbag 2.

Figure 24:
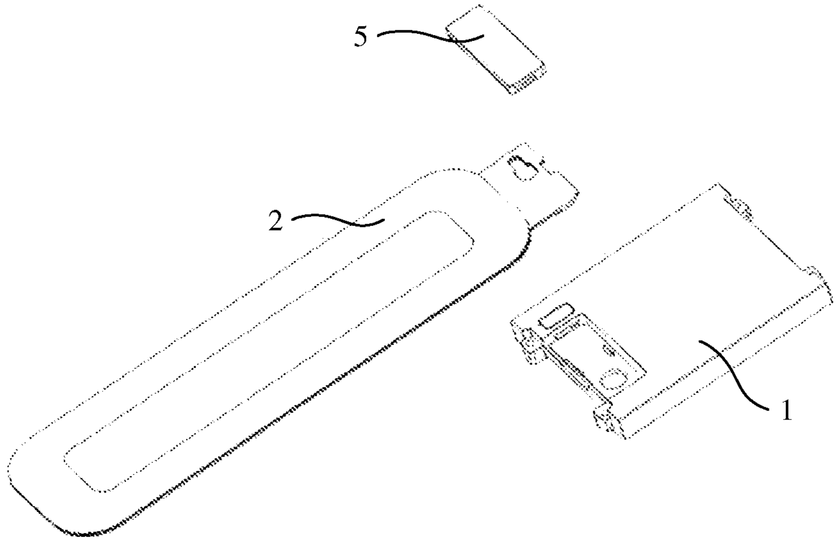
FIG. 24 is a schematic diagram of a structure before installation of an airbag, an airbag cover, and a watch body according to an embodiment of this application.

First, refer to FIG. 24. FIG. 24 shows a schematic diagram of a structure before installation of an airbag 2, an airbag cover 5, and a watch body 1. In this embodiment of this application, before the airbag 2 and the watch body 1 are installed, the airbag 2 and the airbag cover 5 may be first assembled, so that the airbag 2 may be installed on the watch body 1 by installing the airbag cover 5 and the watch body 1, to improve convenience of installing the airbag 2 and the watch body 1.

Figure 25:
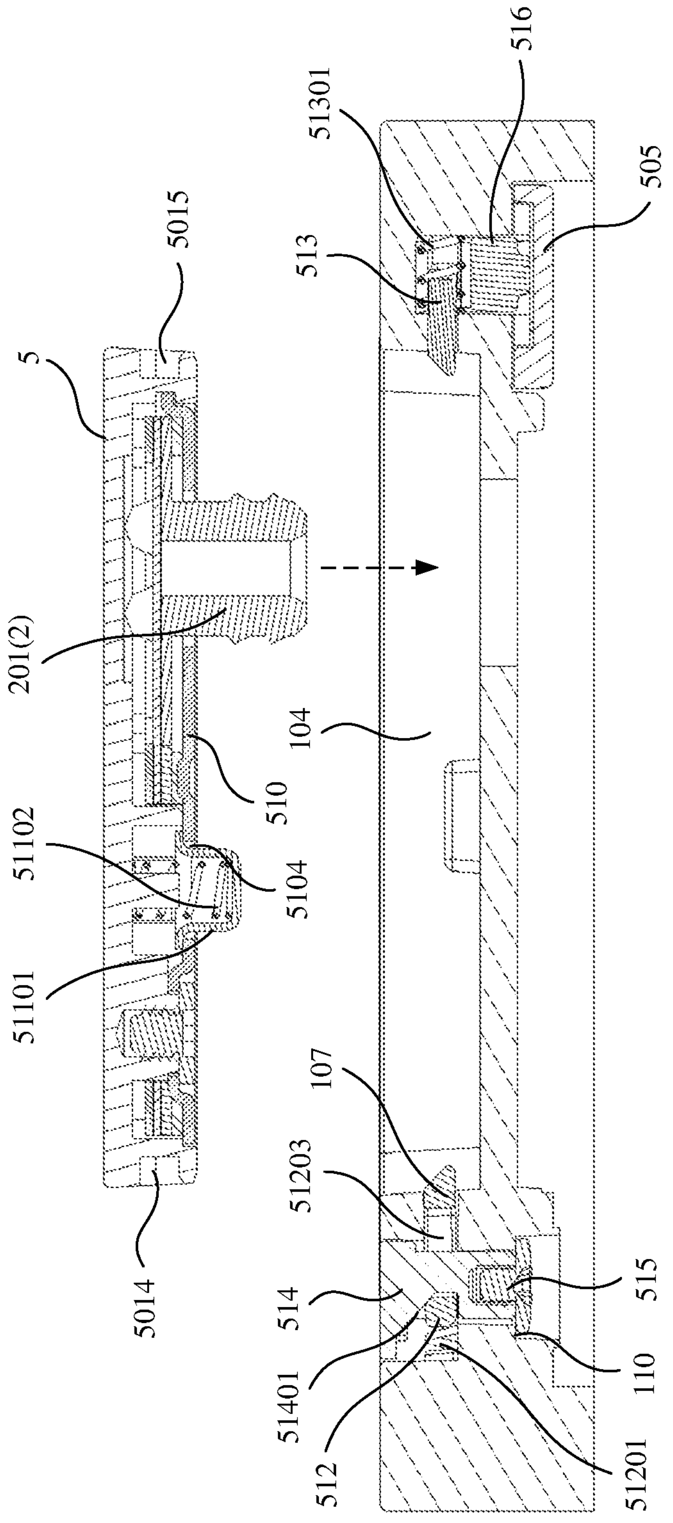
FIG. 25 is a schematic diagram of structures of a watch body and an airbag cover assembled with an airbag before installation according to an embodiment of this application.

Then, refer to FIG. 25. FIG. 25 is a schematic diagram of structures of the watch body 1 and the airbag cover 5 assembled with the airbag 2 before installation. In this case, a part of the third snap fit 512 extends to the installation slot 104, and a part that is of the snap fit button 514 and that penetrates through the opening 51203 of the third snap fit 512 abuts against the third snap fit 512, to limit the third snap fit 512. A part of the fourth snap fit 513 extends to the installation slot 104, and the snap fit support 516 limits movement of the fourth snap fit 513.

Figure 26:
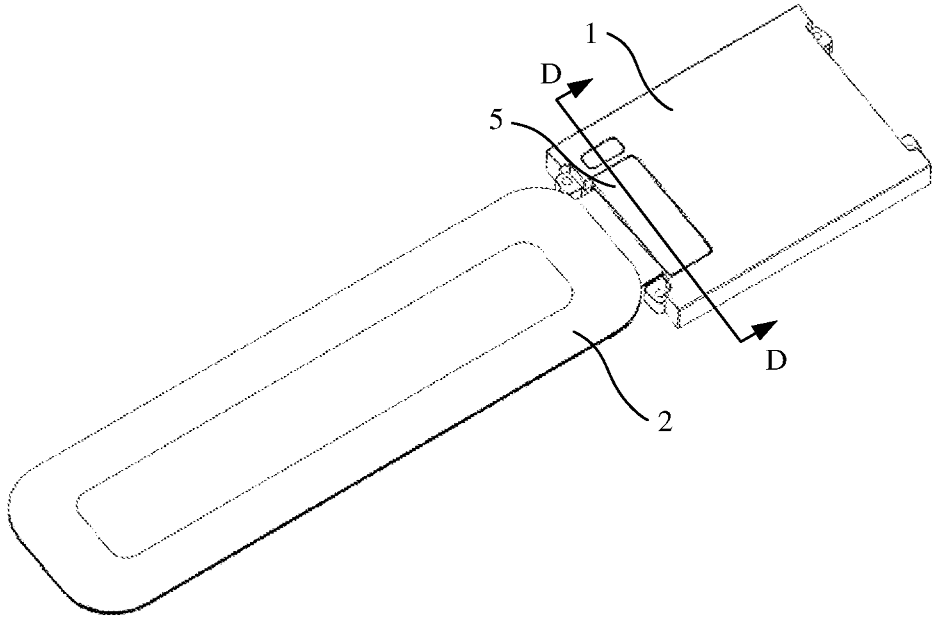
FIG. 26 is a schematic diagram of a structure obtained after installation of an airbag cover and a watch body is completed according to an embodiment of this application.

When the airbag cover 5 is installed into the watch body 1, the airbag cover 5 may be opposite to the accommodating slot 104 of the watch body 1, and a press force toward the accommodating slot 104 may be applied to the airbag cover 5. As the airbag cover 5 is pressed down, the third snap fit 512 and the fourth snap fit 513 move in a direction away from each other. In this process, the elastic component 51201 that elastically abuts against the third snap fit 512 and the elastic component 51301 that elastically abuts against the fourth snap fit 513 are compressed, to accumulate elastic force. When the third snap fit 512 is opposite to the third bayonet 5014, and the fourth snap fit 513 is opposite to the fourth bayonet 5015, the third snap fit 512 and the fourth snap fit 513 may move toward each other under elastic force of corresponding elastic components, and enter respective corresponding bayonets. In this way, installation of the airbag cover 5 and the watch body 1 is completed. FIG. 26 is a schematic diagram of a structure after assembly of the airbag cover 5 and the watch body 1 is completed. It should be noted that, still refer to FIG. 25. In this application, a guide surface may be disposed on parts that are of the third snap fit 512 and the fourth snap fit 513 and that extend into the installation slot 104, and the guide surface may achieve guide effect in a process in which the airbag cover 5 is installed on the watch body 1.

Figure 27:
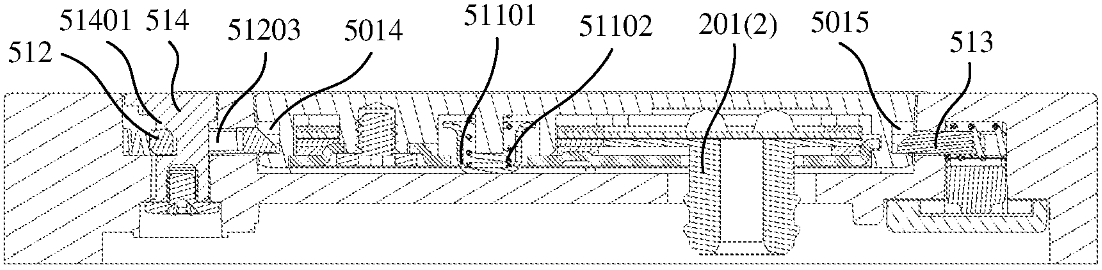
FIG. 27 is a D-D sectional view of the structure shown in FIG. 26.

Refer to FIG. 25 and FIG. 27 together. FIG. 27 is a sectional view at D-D in FIG. 26. In a process of installing the airbag cover 5 on the watch body 1, a part that is of the protrusion cover 51101 and that extends from the protrusion cover hole 5104 of the pressing plate 510 may be in contact with a bottom wall of the installation slot 104 of the watch body 1. In addition, as the airbag cover 5 is pressed to the watch body 1, a height of the part that is of the protrusion cover 51101 and that extends to the protrusion cover hole 5104 gradually decreases, and the elastic component 51102 is gradually compressed to accumulate elastic force. When the airbag cover 5 and the watch body 1 are installed, the elastic component 51102 reaches a maximum compression amount.

In addition, when the airbag cover 5 is disassembled from the watch body 1, refer to FIG. 27. In this case, the snap fit button 514 may be pressed to push the third snap fit 512 in a direction away from the fourth snap fit 513 by moving the snap fit button 514. When the third snap fit 512 is detached from the third bayonet 5014, the protrusion cover 51101 moves in a direction toward the watch body 1 under the elastic force released by the elastic component 51102 of the protrusion cover 51101, to push up the airbag cover 5. In this case, the third bayonet 5014 may be used as a snap fastener, so that the third bayonet 5014 may be manually snap fitted and lifted in a direction away from the watch body 1. That is, the airbag cover 5 may be removed from the watch body 1. It may be understood that, in the foregoing disassembling process, the airbag 2 is not torn, and a service life of the airbag 2 can be effectively prolonged.

In this embodiment of this application, a manner of disposing the airbag cover 5 and the watch body 1 can effectively avoid damage caused by partial pulling of the airbag 2 and the air nozzle 201 in installation and disassembly processes, thereby prolonging a service life of the airbag 2 and the air nozzle 201. In this embodiment of this application, a manner in which the airbag cover 5 is detachably connected to the watch body 1 is used, to implement a connection and disassembly between the airbag 2 and the watch body 1, so that a structure is simple, and an operation is convenient. In this way, replacement and maintenance of the airbag 2 may be convenient. In this way, the user may replace the airbag 2 with another possible accessory based on a specific requirement of the user, to meet a wearing requirement of the user and improve user experience.

In this embodiment of this application, the air nozzle 201 may be directly inserted into the watch body 1 through the air nozzle installation hole of the watch body 1, to prevent foreign matter from entering the watch body 1 after the airbag cover 5 is disassembled. A magnet may be disposed in the airbag cover 5, and a Hall element may be disposed in the watch body 1, and the magnet fits the Hall element. In this way, whether the airbag cover 5 is installed may be detected by using a connection relationship between the magnet and the Hall element. If it is detected that the airbag cover 5 is normally installed on the watch body 1, the wearable device can be used normally. When it is detected that the airbag cover 5 is not installed, the wearable device may send an alarm to remind a user that an internal structure of the watch body 1 is in an exposed state at the air nozzle installation hole, so that the user can take a corresponding measure in time, to avoid a risk of water intrusion or a foreign matter caused by long-term exposure of the internal structure of the watch body 1.

Figure 28:
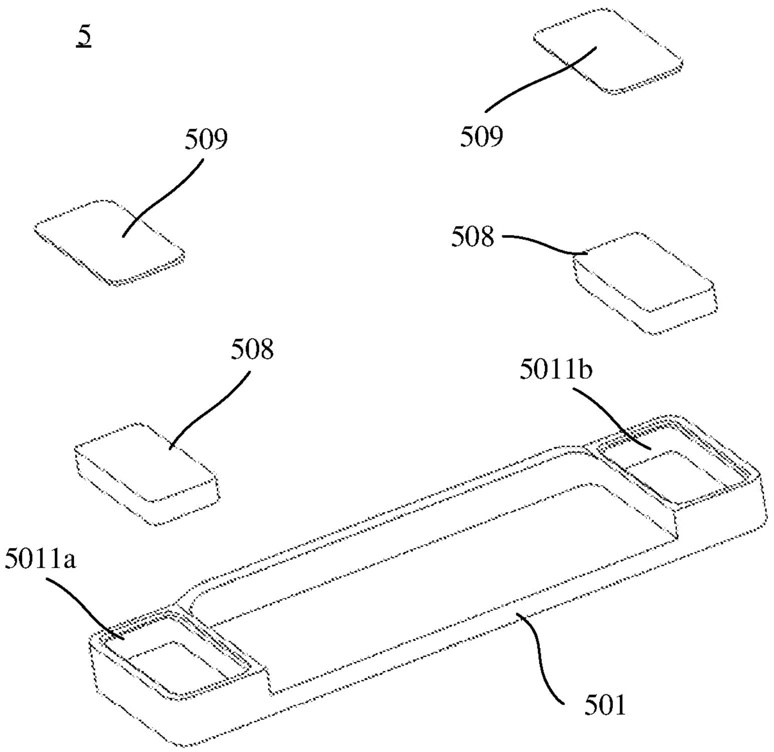
FIG. 28 is an exploded view of an airbag cover according to another embodiment of this application.

In addition to the foregoing manner in which the airbag cover 5 is detachably connected to the watch body 1 through snap-fitting, a magnetic attraction manner may alternatively be used. During specific implementation, refer to FIG. 28. FIG. 28 is an exploded view of an airbag cover 5 according to a possible embodiment of this application. The airbag cover 5 includes a cover body 501 and a first magnetic element 508. For example, there may be two first magnetic elements 508, and the two first magnetic elements 508 are respectively disposed at two opposite ends of the cover body 501. In embodiments of this application, the magnetic element may be an element (for example, a magnet) with magnetism, or may be an element that has magnetism but can be attracted by an element with magnetism.

Figure 29:
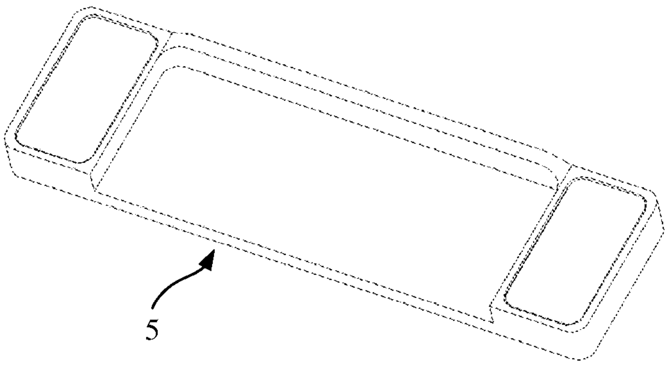
FIG. 29 is a schematic diagram of a structure of an airbag cover according to another embodiment of this application.

Still refer to FIG. 28. The cover body 501 includes an accommodating cavity 5011*a* and an accommodating cavity 5011*b*, and the two first magnetic elements 508 are respectively accommodated in the accommodating cavity 5011*a* and the accommodating cavity 5011*b*. Each of the accommodating cavity 5011*a* and the accommodating cavity 5011*b* has an opening on a side that faces the watch body 1, which may facilitate installation of the magnetic element. In addition, magnetic element covers 509 corresponding to the accommodating cavity 5011*a* and the accommodating cavity 5011*b* may further be disposed on the airbag cover 5 respectively. The magnetic element covers 509 cover openings of the accommodating cavity 5011*a* and the accommodating cavity 5011*b*, and are fastened to the cover body 501 to form an airbag cover 5 of a structure shown in FIG. 29, to prevent the magnetic element from falling off from the corresponding accommodating cavity.

In some other embodiments of this application, only one magnetic element cover 509 may be disposed on the airbag cover 5, and the magnetic element cover 509 is an integrally formed structure. In this way, the magnetic element cover 509 may cover openings of two accommodating cavities at the same time.

Figure 30:
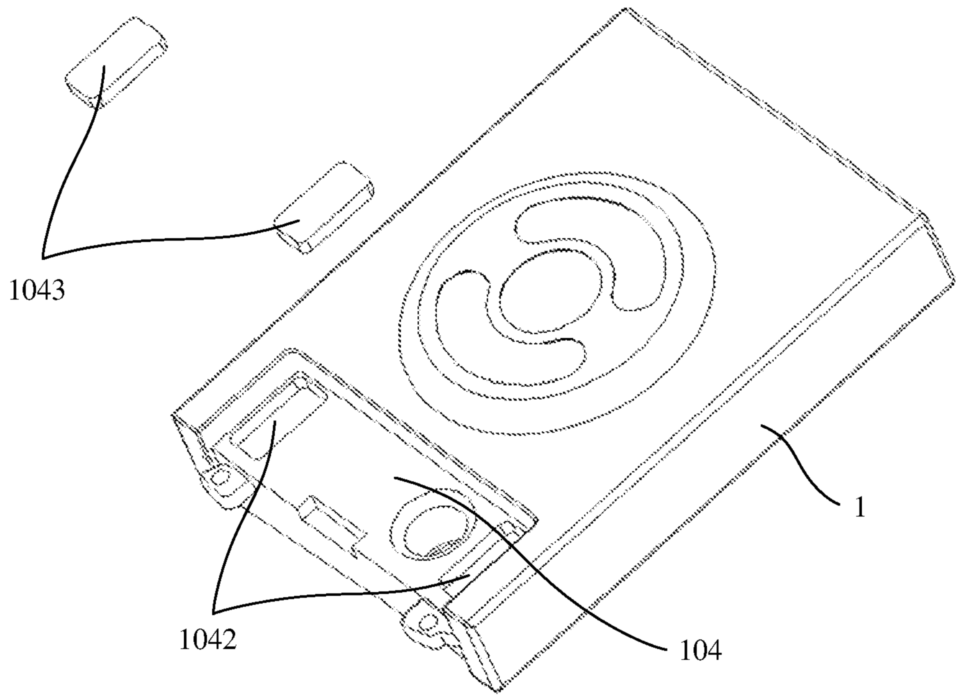
FIG. 30 is an exploded view of a watch body according to another embodiment of this application.
Figure 31:
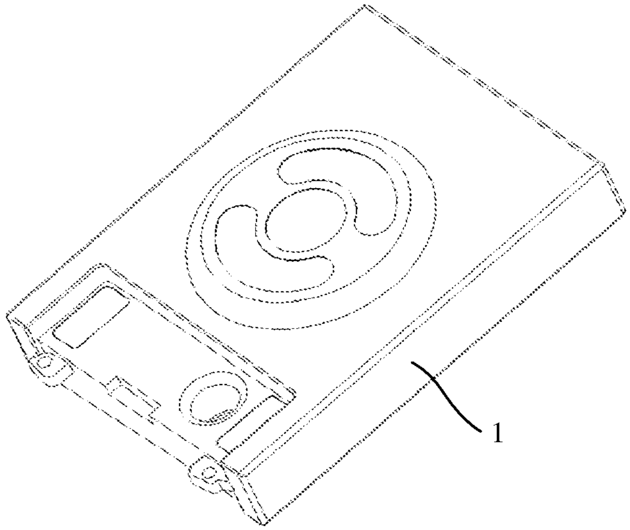
FIG. 31 is a schematic diagram of a structure of a watch body according to an embodiment of this application.
Figure 32:
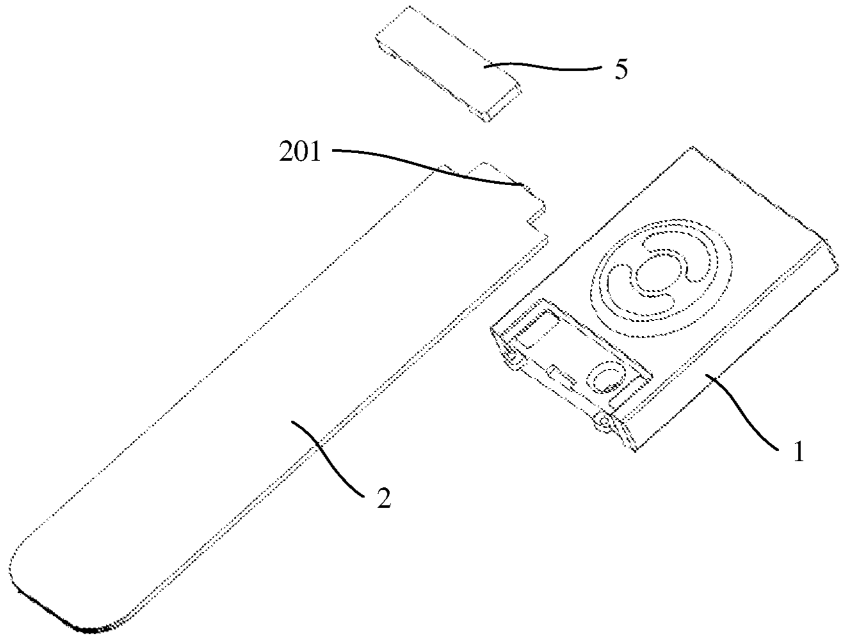
FIG. 32 is an exploded view of a structure of a wearable device according to an embodiment of this application.

To enable the airbag cover 5 to be connected to the watch body 1, refer to FIG. 30. FIG. 30 is a schematic diagram of a structure of a watch body 1 according to a possible embodiment of this application. An end of the watch body 1 is provided with an installation slot 104, two recesses 1042 are disposed on a bottom wall of the installation slot 104, and one second magnetic element 1043 is installed in each of the two recesses 1042. Refer to FIG. 31 and FIG. 32 together. The two recesses 1042 may be disposed on two sides of an area that is of the installation slot 104 and that is used to install an airbag. In this way, a part that is of an airbag 2 and on which an air nozzle 201 is disposed may be accommodated in the installation slot 104.

In some embodiments of this application, a magnetic attraction capability of a magnetic element may be selected, so that only one first magnetic element 508 is disposed in a cover body 501, only one second magnetic element 1043 is disposed in the installation slot 104 of the watch body 1, and the first magnetic element 508 and the second magnetic element 1043 attract each other to implement a detachable connection between an airbag cover 5 and the watch body 1. In addition, when the cover body 501 and the installation slot 104 have large space for disposing a magnetic element, more than two magnetic elements may be separately disposed in the cover body 501 and the installation slot 104, to improve reliability of a connection between the airbag cover 5 and the watch body 1.

The manner of disposing the airbag cover 5 and the watch body 1 in this embodiment may make a fastening and disassembling process of the airbag 2 and the watch body 1 simpler. When the airbag 2 is fastened to the watch body 1, the air nozzle 201 of the airbag 2 may be first inserted into the watch body 1, and then the airbag cover 5 covers the watch body 1 from a side that is of the airbag 2 and that is away from the watch body 1. Two first magnetic elements 508 of the airbag cover 5 are attracted to two second magnetic elements 1043 on the watch body 1 in a one-to-one correspondence, so that the airbag cover 5 is fastened to the watch body 1. In this case, the airbag 2 is crimped on the watch body 1 by the airbag cover 5. In addition, when the airbag 2 is disassembled from the watch body 1, the airbag cover 5 only needs to be pulled out of the watch body 1, and then the airbag 2 is removed from the watch body 1. It may be understood that, in this embodiment of this application, at least one of the first magnetic element 508 and the second magnetic element 1043 is magnetic. In addition, reliability of the connection between the airbag cover 5 and the watch body 1 may alternatively be improved by selecting a quantity and magnetism of first magnetic elements 508 and a quantity and magnetism of second magnetic elements 1043.

In this embodiment of this application, a manner in which the airbag cover 5 is detachably connected to the watch body 1 is used, to implement a fastening connection and disassembly between the airbag 2 and the watch body 1, so that a structure is simple, and an operation is convenient. In this way, replacement and maintenance of the airbag 2 may be convenient. In addition, the user may replace the airbag 2 with another possible accessory based on a specific requirement of the user, to meet a wearing requirement of the user and improve user experience.

It may be understood that, in addition to the manner that is described in the foregoing embodiment and in which the airbag may be detachably connected to the watch body, another possible manner may be used. For example, a first snap fit, a second snap fit, and two first magnetic elements may be simultaneously disposed on the airbag cover, and two bayonets and two second magnetic elements may be simultaneously disposed on the watch body, so that the airbag cover and the watch body are simultaneously connected in a snap-fitting and magnetic attraction manner. This can effectively improve reliability of the connection between the airbag cover and the watch body. In addition, one end of the airbag cover may be further snap-fitted to the watch body by using the first snap fit or the second snap fit, and the other end is connected through magnetic attraction between the first magnetic element and the second magnetic element, so that the airbag cover is reliably connected to the watch body, and a structure of a wearable device is simplified.

Figure 33:
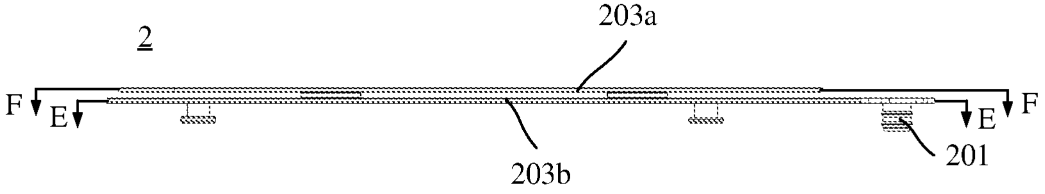
FIG. 33 is a schematic diagram of a structure an airbag according to another embodiment of this application.

When the wearable device provided in this application is used to perform blood pressure detection, the airbag 2 usually needs to be bent from a flat state shown in FIG. 33. For example, the airbag 2 is bent into a form shown in FIG. 34 or FIG. 35, so that the airbag 2 can fit a wearing part such as a wrist, thereby helping improve detection precision.

Figure 36:
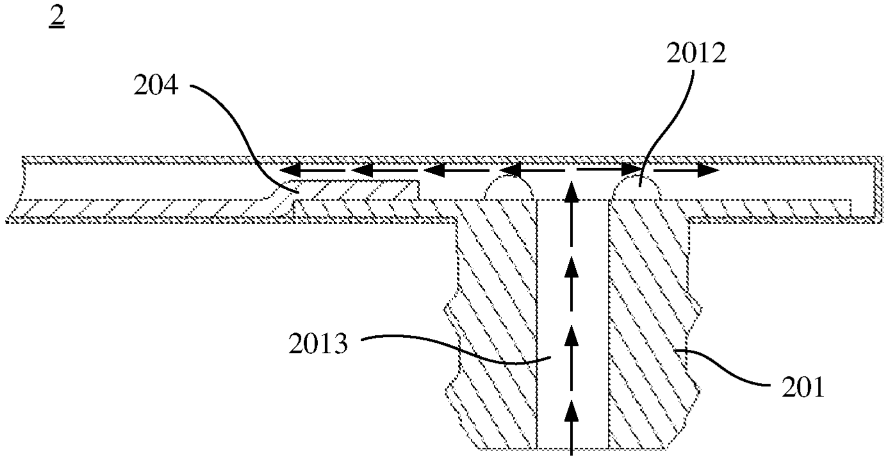
FIG. 36 is a schematic diagram of an internal structure of an airbag according to another embodiment of this application.

However, when the airbag 2 is bent, a clearance between inner walls of the airbag 2 changes, which may affect flow of air in an air cavity of the airbag 2. Refer to FIG. 36. FIG. 36 shows an internal structure of an airbag 2 according to another embodiment of this application. In order to ensure that an air cavity in the airbag 2 is unblocked, in an embodiment of this application, a support protrusion 2012 may be disposed on an end face that is of an air nozzle 201 and that is inside the airbag.

Figure 37:
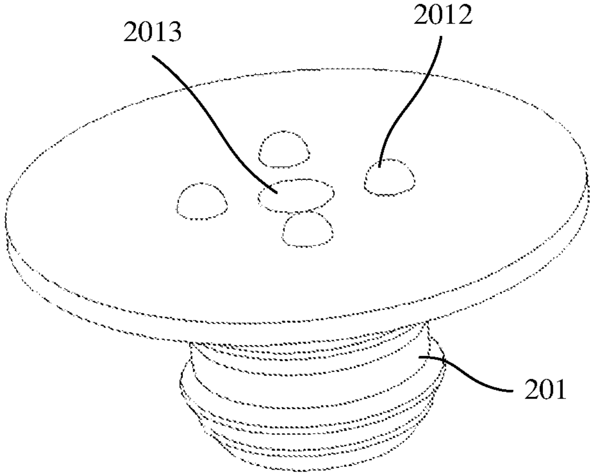
FIG. 37 is a schematic diagram of a structure of an air nozzle according to an embodiment of this application.

Refer to FIG. 36 and FIG. 37 together. FIG. 37 is a schematic diagram of a structure of an air nozzle 201 according to an embodiment of this application. An arrow in FIG. 36 represents a flow direction of air that enters the airbag 2 through the air nozzle 201. In this embodiment, the support protrusion 2012 protrudes from an end surface of the air nozzle 201 along a direction in which the air enters the airbag 2 from the air nozzle 201. In addition, refer to FIG. 37. Support protrusions 2012 may be disposed in a dot shape, there may be one support protrusion 2012 or at least two support protrusions 2012, and the support protrusions 2012 may be disposed on a peripheral side of an air hole 2013 of an air nozzle 201.

In this way, refer to FIG. 36 and FIG. 37 together. Even when the airbag 2 is bent, a side wall that is of the airbag 2 and that is located near the air nozzle 201 is prevented from blocking the air hole 2013 of the air nozzle 201 under support of the support protrusion 2012, so that external air can smoothly enter the airbag 2 through the air nozzle 201, thereby ensuring an air filling amount of the airbag 2, reducing impact on measurement precision, and ensuring implementation of a product function.

Figure 38A:
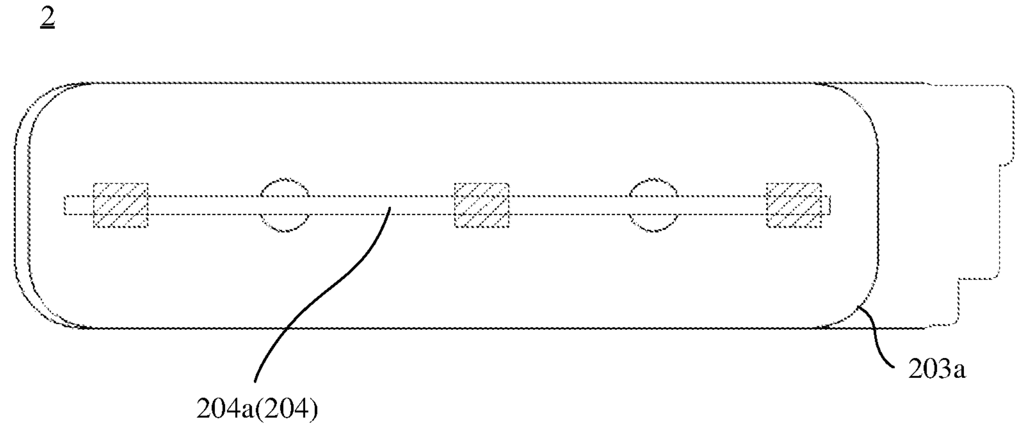
FIG. 38*a* is an E-E sectional view of the airbag shown in FIG. 33.
Figure 38B:
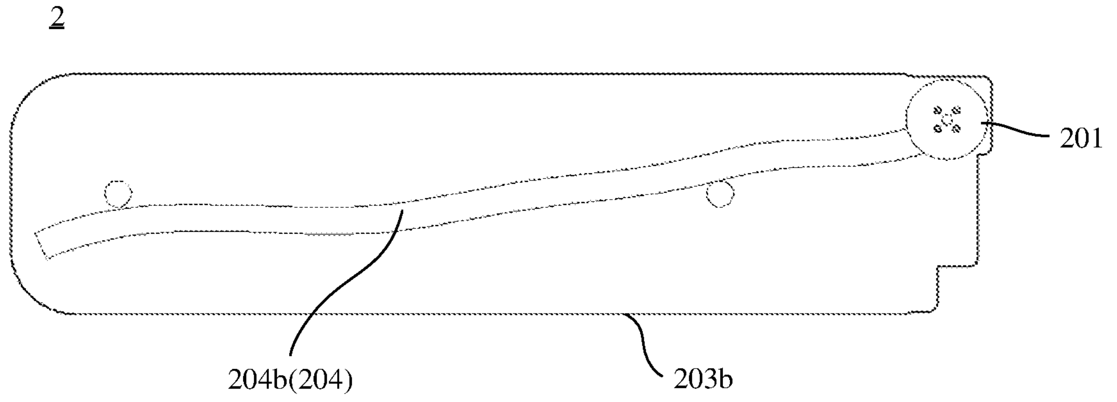
FIG. 38*b* and FIG. 38*c* are F-F sectional views of the airbag shown in FIG. 33.
Figure 38C:
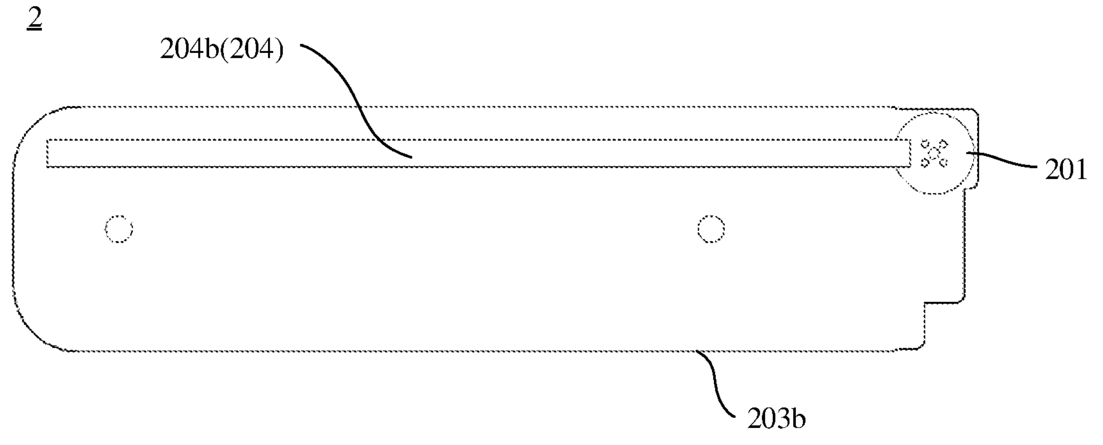

In addition, when the airbag 2 is bent, there may be a wrinkle in a local area, which causes the air cavity in the airbag 2 to be blocked, thereby affecting normal working of the wearable device. In order to ensure that the air cavity in the airbag 2 is always unblocked in different application scenarios and working conditions, refer to FIG. 38*a* to FIG. 38*c*. FIG. 26*a* to FIG. 38*c* show an internal structure of an airbag according to an embodiment of this application. A flexible inner object 204 is disposed inside an airbag 2, and there may be one or more flexible inner objects 204. In addition, there may be a clearance between the flexible inner object 204 and an inner wall of the airbag 2, and the flexible inner object 204 may be at least partially fastened to the side wall of the airbag 2 as shown in FIG. 38*a* partially. Alternatively, as shown in FIG. 38*b* and FIG. 38*c*, one end of the flexible inner object 204 is in a free state (that is, can move freely), and the other end is fastened to an air nozzle 201. In addition, an extension direction of the flexible inner object 204 and an extension direction of the airbag 2 may be same, or the extension direction of the flexible inner object 204 may be an angle (for example, as shown in FIG. 38*b*) with the extension direction of the airbag 2.

In this solution, in a bending process of the airbag 2, side walls of the airbag 2 are separated by using the flexible inner object 204, the flexible inner object 204 has a certain thickness, and a size of the flexible inner object 204 is less than an internal size of the airbag 2. In this way, a certain clearance is still reserved in the airbag 2, and this can still ensure that the air cavity in the airbag 2 is unblocked, thereby reducing impact on measurement precision and ensuring implementation of a product function.

Figure 34:
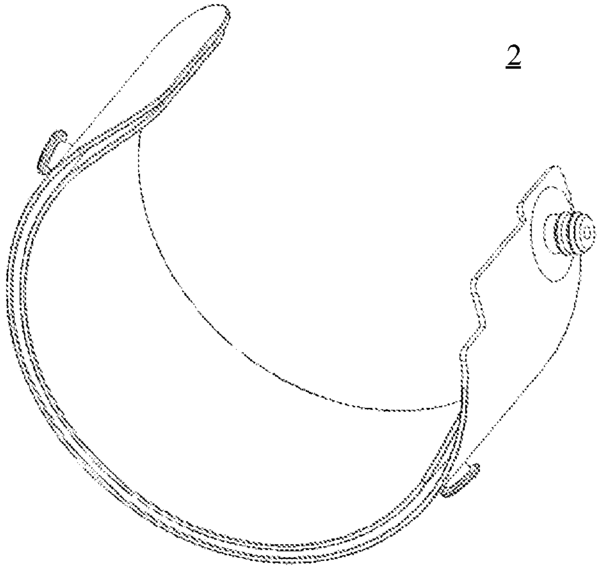
FIG. 34 is a schematic diagram of an airbag in a bent state according to an embodiment of this application.
Figure 35:
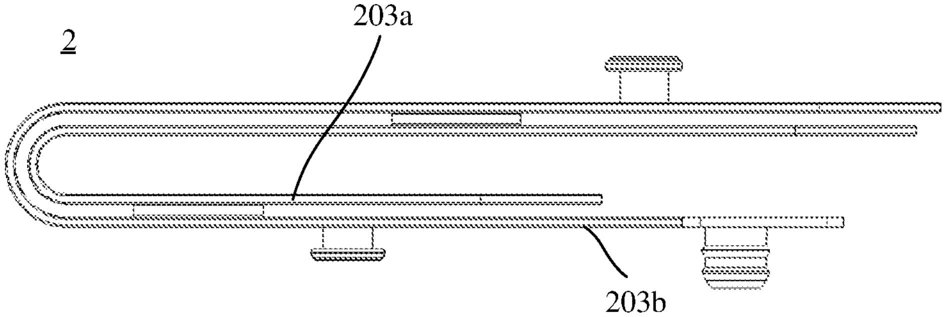
FIG. 35 is a schematic diagram of an airbag in a bent state according to another embodiment of this application.

In addition, a size of inflatable space of the airbag 2 plays a key role in accuracy of blood pressure detection. Refer to FIG. 33 to FIG. 35. In some embodiments of this application, for example, the airbag 2 may include two superposed layer structures, each layer structure has one cavity, and cavities of the two layer structures are connected to each other, to form the air cavity of the airbag 2. In this way, the inflatable space of the airbag 2 may be large in a limited size, thereby improving measurement precision, helping reduce a width of the airbag 2, and improving user experience. In this application, for ease of description, a layer structure that is of the airbag 2 and that is in direct contact with the wearing part of the user may be referred to as a first layer structure 203*a*, and a layer structure that is far away from the wearing part of the user is referred to as a second layer structure 203*b*. The first layer structure 203*a* has a first cavity, and the second layer structure 203*b* has a second cavity.

It may be understood that, when the airbag 2 includes the first layer structure 203*a* and the second layer structure 203*b* that are superposed, refer to FIG. 38*a* to FIG. 38*c*. The flexible inner object 204 inside the airbag 2 in the foregoing embodiment may be disposed in the first layer structure 203*a*, or may be disposed in the second layer structure 203*b*. Alternatively, flexible inner objects 204 may be disposed in both the first layer structure 203*a* and the second layer structure 203*b* separately. In addition, there may be one or more flexible inner objects 204 in both the first layer structure 203*a* and the second layer structure 203*b*, and types of the flexible inner objects 204 in the first layer structure 203*a* and the second layer structure 203*b* may be same or may be different.

In some embodiments of this application, for ease of differentiation, the flexible inner object 204 disposed in the first layer structure 203*a* may be referred to as a first flexible inner object 204*a*, and the flexible inner object 204 disposed in the second layer structure 203*b* may be referred to as a second flexible inner object 204*b*. Refer to FIG. 38*a*. The first flexible inner object 204*a* may be at least partially fastened to an inner wall of the first layer structure 203*a*, and an extension direction of the first flexible inner object 204*a* and an extension direction of the first layer structure 203*a* may be approximately same. In addition, there may be a clearance between the first flexible inner object 204*a* and the inner wall of the first layer structure 203*a*. Refer to FIG. 38*b* and FIG. 38*c*. One end of the second flexible inner object 204 may be connected to the air nozzle 201, the other end is in a free state, and there may be a clearance between the second flexible inner object 204*b* and an inner wall of the second layer structure 203*b*. In this way, when the airbag 2 is bent, a specific clearance is still reserved in the first layer structure 203*a* and the second layer structure 203*b*, and this can still ensure that the air cavity in the airbag 2 is unblocked, thereby reducing impact on measurement precision and ensuring implementation of a product function.

In order to understand a specific structure of the airbag 2 in this application, the following describes a method for preparing the airbag 2.

In a possible embodiment, an airbag 2 is made by using a hot melt edge inverting preparation process. For specific implementation, refer to FIG. 39*a* to FIG. 39*f*.

Figure 39A:
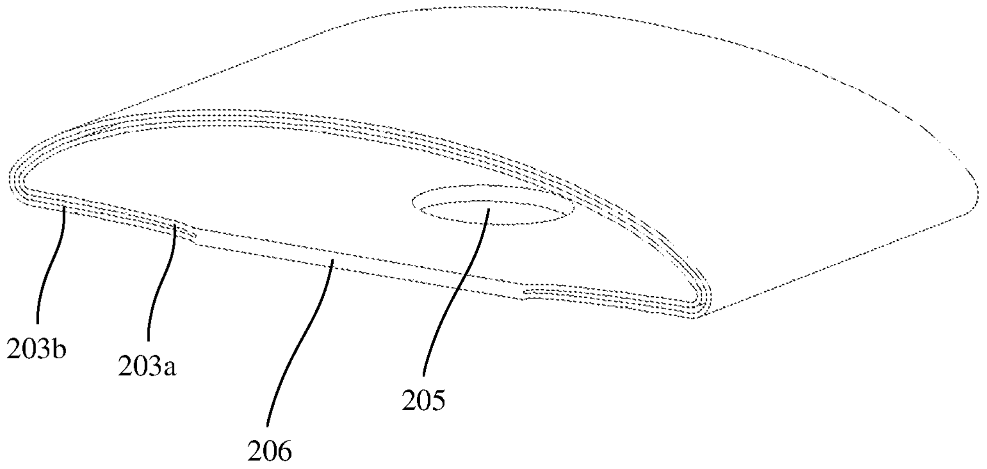
FIG. 39*a* to FIG. 39*f* are schematic diagrams of an airbag preparation process according to an embodiment of this application.
Figure 39B:
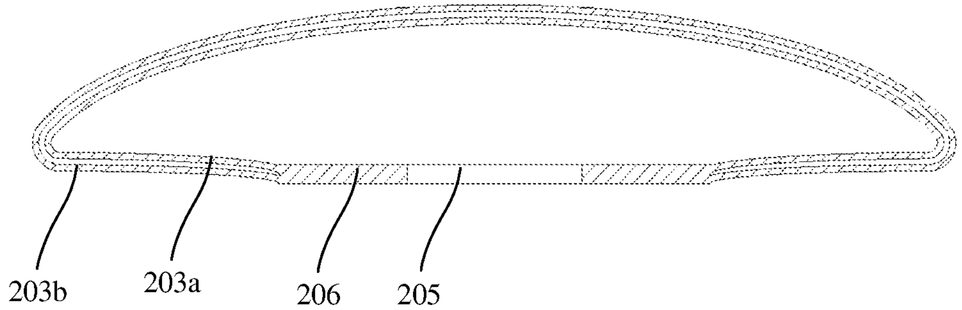
Figure 39C:
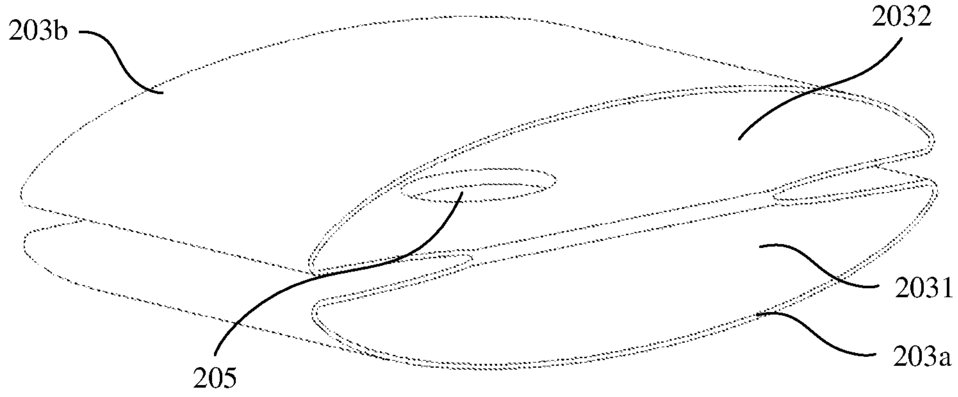

Step 1: Sleeve a first layer structure 203*a* and a second layer structure 203*b* that have openings at two ends, where the first layer structure 203*a* has a first cavity, the second layer structure 203*b* has a second cavity, and the first layer structure 203*a* is located in the second cavity of the second layer structure 203*b*, to form an inner-layer and outer-layer sleeved structure; and then connect partial areas of the two layer structures together. The two layer structures are connected by jointing through a hot melt process. A connection area 206 of the layer structures may be disposed along an extension direction of the layer structures, and the connection area 206 may be distributed in a strip shape or in a dot shape. Then, a through hole 205 is disposed in the connection area 206, so that the first cavity and the second cavity are connected. In this case, a structure shown in FIG. 39*a* is obtained. FIG. 39*b* is a sectional view of the structure shown in FIG. 39*a*.

Figure 39D:
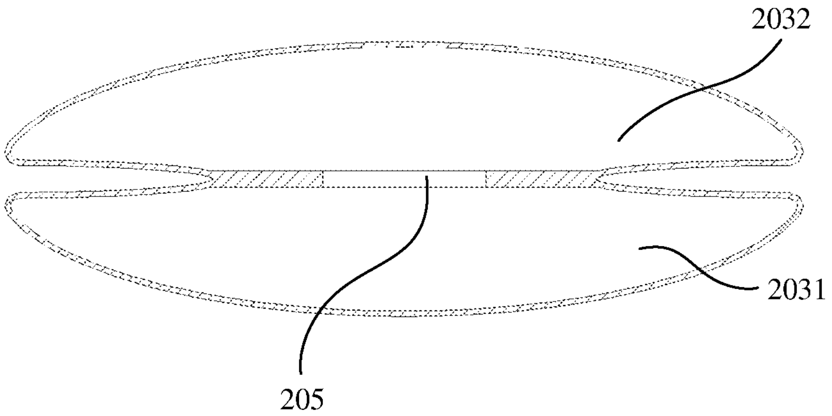

Step 2: Turn over the second layer structure 203*b* from end to end, and turn over the two layers of the inner-layer and outer-layer sleeved structure into the superposed first layer structure 203*a* and second layer structure 203*b*, to obtain a structure shown in FIG. 39*c*. FIG. 39*d* is a sectional view of the structure shown in FIG. 39*c*. In this case, a first cavity 2031 of the first layer structure 203*a* is connected to a second cavity 2032 of the second layer structure 203*b* through a through hole 205.

Figure 39E:
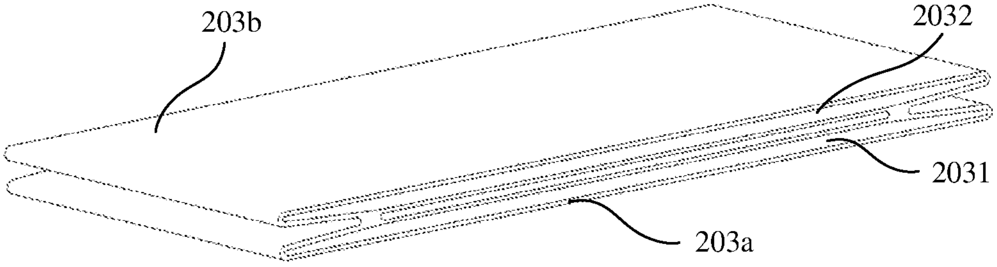
Figure 39F:
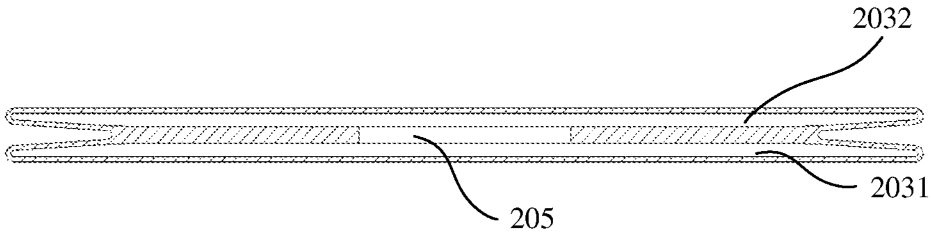

In addition to the foregoing steps, the first layer structure 203*a* and the second layer structure 203*b* that are obtained in the second step may be further leveled by ironing along a fold line, so that the first layer structure 203*a* and the second layer structure 203*b* are flattened and regular, to form a structure shown in FIG. 39*e*. FIG. 39*f* is a sectional view of the structure shown in FIG. 39*e*. In addition, after the structure shown in FIG. 39*e* is obtained, an air nozzle 201 may be installed. For example, the air nozzle 201 may be installed on a side that is of the second layer structure 203*b* and that is away from the first layer structure 203*a*, to facilitate a connection between an airbag and a watch body 1. It may be understood that an air hole of the air nozzle may be connected to the second cavity 2032 of the second layer structure 203*b*. Finally, openings at two ends of the first layer structure 203*a* and the second layer structure 203*b* in the structure obtained in FIG. 39*e* are sealed. A sealing manner may be, but is not limited to, jointing through a hot melt process, to form the closed airbag 2 shown in FIG. 33 to FIG. 35. In addition, the foregoing steps are an example of a preparation process of the airbag 2 in this embodiment of this application. Based on this embodiment, a person skilled in the art may properly adjust the foregoing steps to prepare the airbag 2 in this application, which should be understood as falling within the protection scope of this application.

For the airbag 2 prepared by using the foregoing hot melt edge inverting process, a hot melt edge of the airbag 2 does not occupy inflatable space of the airbag 2. In this way, inflatable space of cavities of the two layer structures can be maximized in a limited size, and this helps improve measurement precision.

Figure 40A:
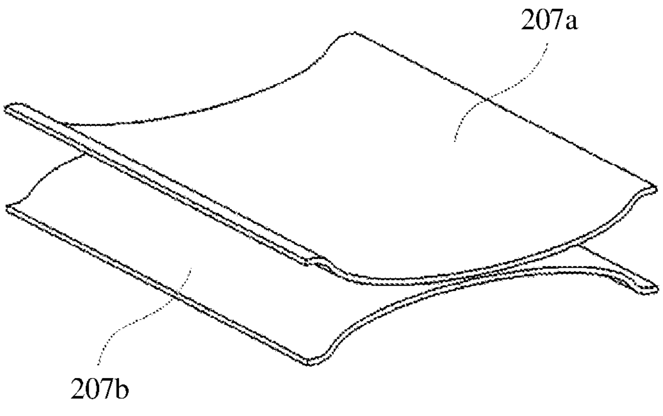
FIG. 40*a* to FIG. Ooh are schematic diagrams of an airbag preparation process according to another embodiment of this application.
Figure 40B:
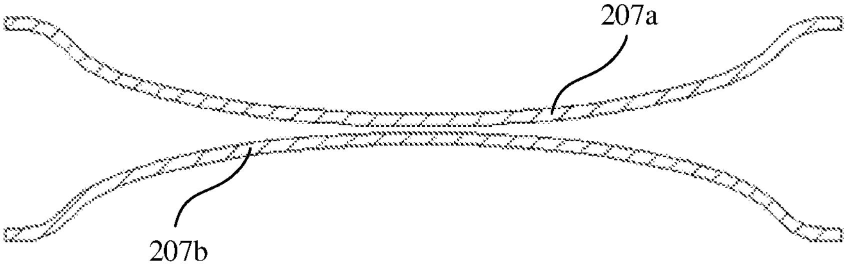
Figure 40C:
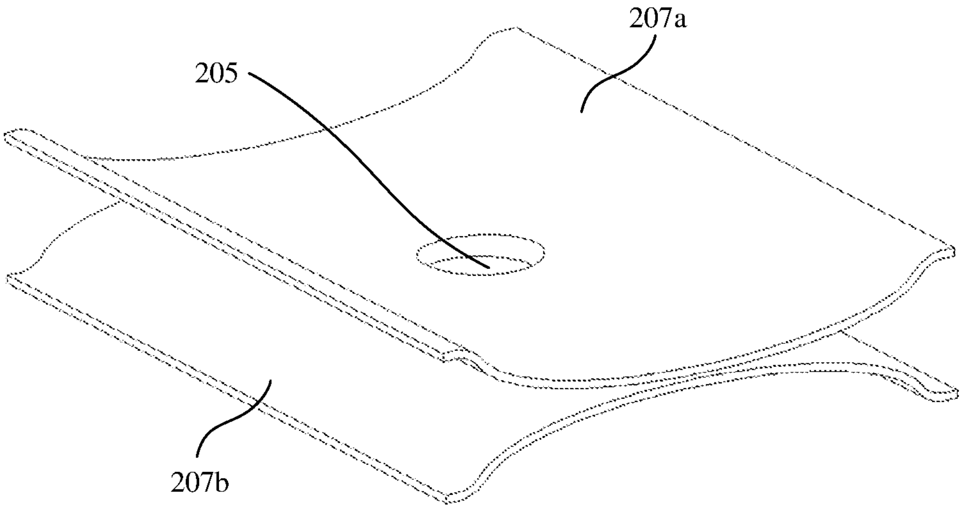

In another possible embodiment of this application, the airbag 2 may be further obtained through processing by using the preparation method shown in FIG. 40*a* to FIG. 40*h*. During specific implementation:

Step 1: Superpose a first curved surface structure 207*a* and a second curved surface structure 207*b*, where the two curved surface structures are bent in a direction opposite to each other, and connect the two curved surface structures, to obtain a structure shown in FIG. 40*a*, where FIG. 40*b* is a sectional view of the structure shown in FIG. 40*a*. In this step, the two curved surface structures may be, but is not limited to, connected by jointing through a hot melt process.

Figure 40D:
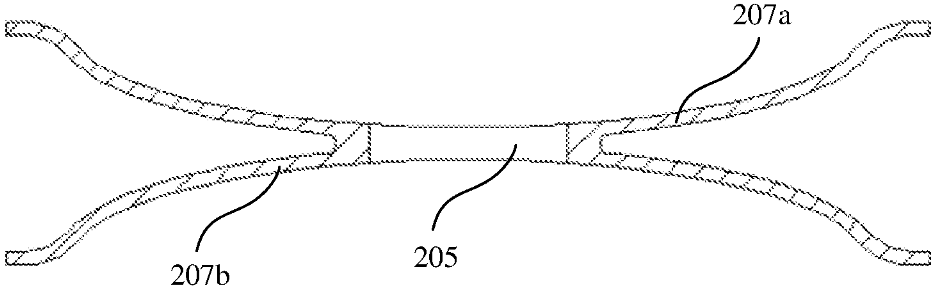

Step 2: Dispose a through hole 205 in a connection area of the first curved surface structure 207*a* and the second curved surface structure 207*b*, where the connection area may be in a strip shape or a dot shape, and the through hole 205 simultaneously penetrates the two curved surface structures, to obtain a structure shown in FIG. 40*c*. FIG. 40*d* is a sectional view of the structure shown in FIG. 40*c*.

Figure 40E:
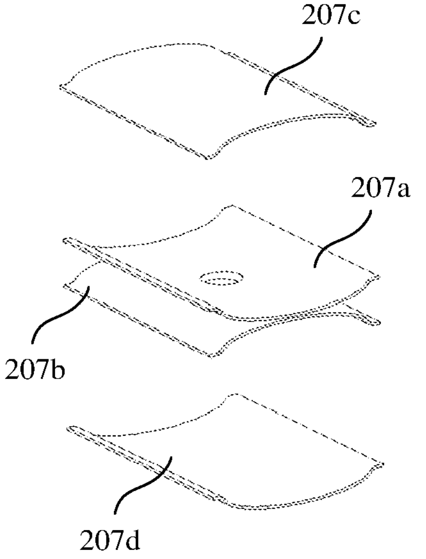

Step 3: Refer to FIG. 40*e*. Snap fit a third curved surface structure 207*c* on the first curved surface structure 207*a*, and connect the first curved surface structure 207*a* to a periphery of the third curved surface structure 207*c*; and snap fit a fourth curved surface structure 207*d* on the second curved surface structure 207*b*, and connect the second curved surface structure 207*b* to a periphery of the fourth curved surface structure 207*d*. In this step, both the first curved surface structure 207*a* and the third curved surface structure 207*c*, and the second curved surface structure 207*b* and the fourth curved surface structure 207*d* may be, but is not limited to, connected by jointing through a hot melt process.

Figure 40F:
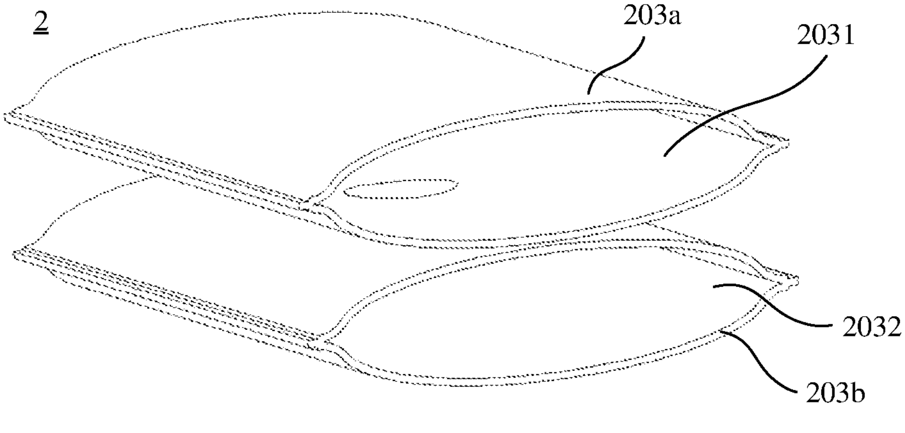
Figure 40G:
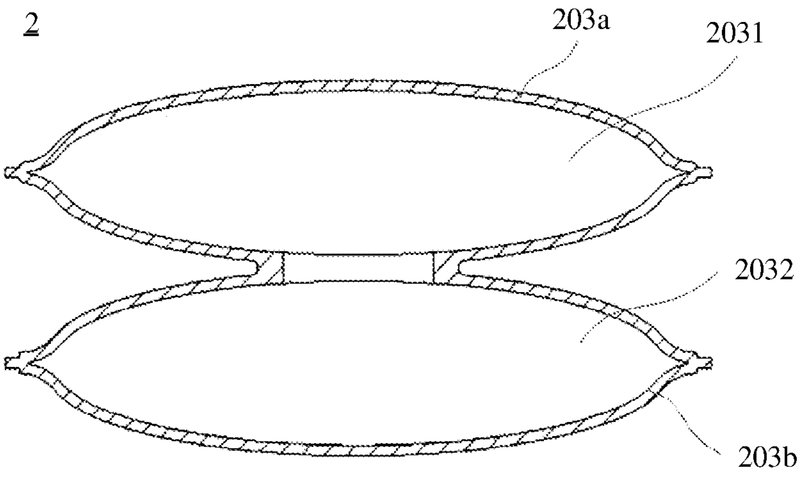

It may be understood that, a bending aspect of the third curved surface structure 207*c* is opposite to a bending aspect of the first curved surface structure 207*a*, and a bending aspect of the fourth curved surface structure 207*d* is opposite to a bending aspect of the second curved surface structure 207*b*, so that the third curved surface structure 207*c* is connected to the first curved surface structure 207*a* to form a layer structure having a cavity, and the fourth curved surface structure 207*d* is connected to the second curved surface structure 207*b* to form a layer structure having a cavity, to obtain structures shown in FIG. 40*f* and FIG. 40*g*. In order to show an internal structure of the airbag 2, FIG. 40*f* is a schematic diagram of a structure of the airbag 2 without two ends, and FIG. 40*g* is a sectional view of the airbag 2.

It should be noted that, in this embodiment, structural surfaces configured to form the two layer structures of the airbag 2 may not be curved surfaces, provided that both the two layer structures of the prepared airbag 2 can have a cavity. In addition, the foregoing steps are also an example of a preparation process of the airbag 2 in this embodiment of this application. In some possible embodiments, after the first curved surface structure 207*a* and the second curved surface structure 207*b* are superposed, the through hole 205 may be disposed, and then a peripheral side of the through hole 205 is connected in a manner such as jointing through a hot melt process.

Figure 40H:
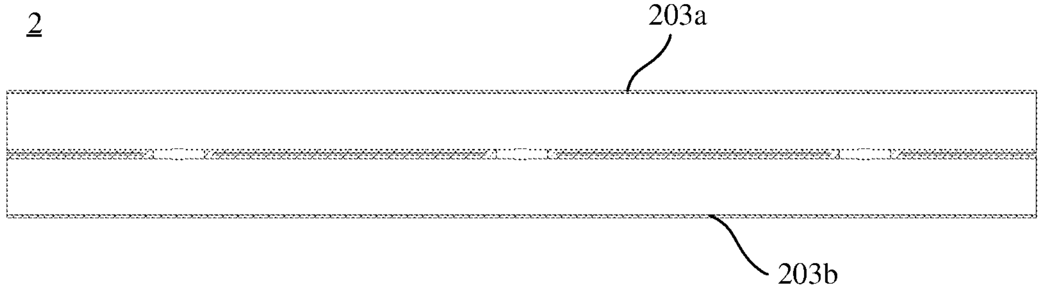

In addition to the foregoing steps, the airbag 2 obtained in FIG. 40*f* may be further leveled by ironing a fold line, so that the airbag 2 is flattened and regular, to form a structure shown in FIG. 40*h*. After the airbag 2 is flattened, an air nozzle 201 may be installed. For example, the air nozzle 201 may be installed on a side that is of the second layer structure 203*b* of the airbag 2 and that is away from the first layer structure 203*a*, to facilitate the connection between the airbag 2 and the watch body 1. It may be understood that an air hole of the air nozzle 201 may be connected to a second cavity 2032 of the second layer structure 203*b*. In addition, the foregoing steps are an example of a preparation process of the airbag 2 in this embodiment of this application. Based on this embodiment, a person skilled in the art may properly adjust the foregoing steps to prepare the airbag 2 in this application, which should be understood as falling within the protection scope of this application.

Figure 41A:
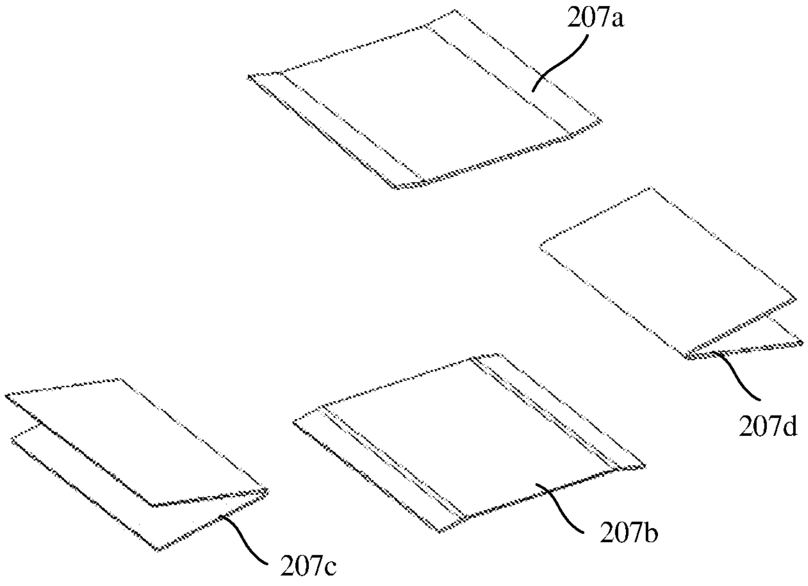
FIG. 41*a* to FIG. 41*h* are schematic diagrams of an airbag preparation process according to another embodiment of this application.
Figure 41B:
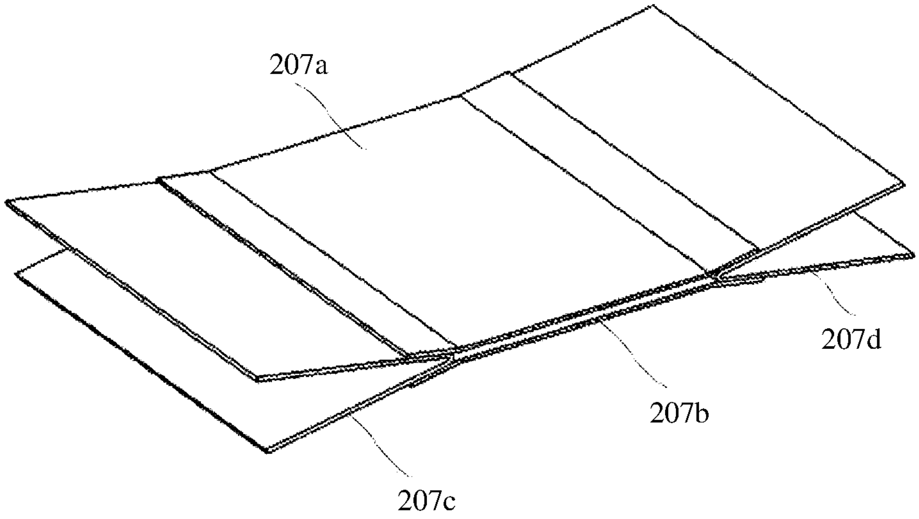

Refer to FIG. 41*a* to FIG. 41*h*. Another embodiment of this application further provides a method for preparing an airbag 2. Preparation steps of the method are as follows:

Step 1: Refer to FIG. 41*a*. Superpose a first curved surface structure 207*a* and a second curved surface structure 207*b*, and place a third curved surface structure 207*c* and a fourth curved surface structure 207*d* on two sides of the first curved surface structure 207*a* and the second curved surface structure 207*b* in a direction perpendicular to a superposing direction of the first curved surface structure 207*a* and the second curved surface structure 207*b*, where the third curved surface structure 207*c* and the fourth curved surface structure 207*d* are bent in directions against each other, and in addition, the third curved surface structure 207*c* and the fourth curved surface structure 207*d* may be, but not limited to, bent in a V-shaped or U-shaped shape.

Figure 41C:
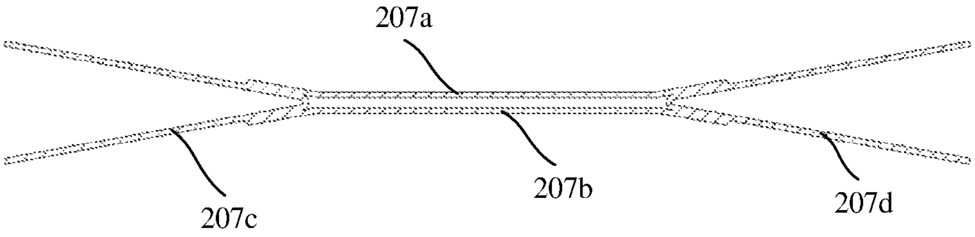

Step 2: Place two oppositely disposed edges of the first curved surface structure 207*a* respectively on the third curved surface structure 207*c* and the fourth curved surface structure 207*d*, and fasten the two oppositely disposed edges of the first curved surface structure 207*a* to the third curved surface structure 207*c* and the fourth curved surface structure 207*d*; and place two oppositely disposed edges of the second curved surface structure 207*b* respectively on the third curved surface structure 207*c* and the fourth curved surface structure 207*d*-surface structure 207*d*, and fasten the two oppositely disposed edges of the second curved surface structure 207*b* to the third curved surface structure 207*c* and the fourth curved surface structure 207*d*-surface structure 207*d*. The first curved surface structure 207*a* and the second curved surface structure 207*b*, and the third curved surface structure 207*c* and the fourth curved surface structure 207*d* may be, but not limited to, connected by jointing through a hot melt process. In this step, the first curved surface structure 207*a* and the second curved surface structure 207*b* are respectively connected to the third curved surface structure 207*c* and the fourth curved surface structure 207*d* from two opposite directions, so that the third curved surface structure 207*c* and the fourth curved surface structure 207*d* support the first curved surface structure 207*a* and the second curved surface structure 207*b*, that is, there may be a specific clearance between the first curved surface structure 207*a* and the second curved surface structure 207*b*, to obtain a structure shown in FIG. 41*b*. FIG. 41*c* shows a sectional view of the structure in FIG. 41*b*.

Figure 41D:
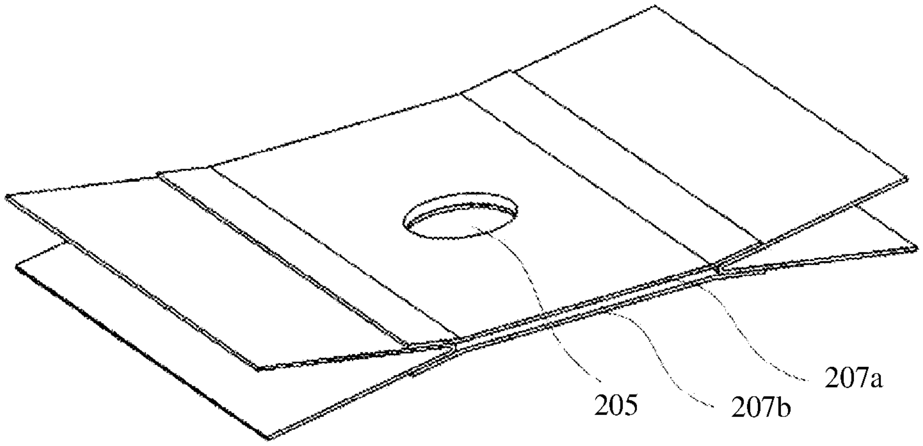
Figure 41E:
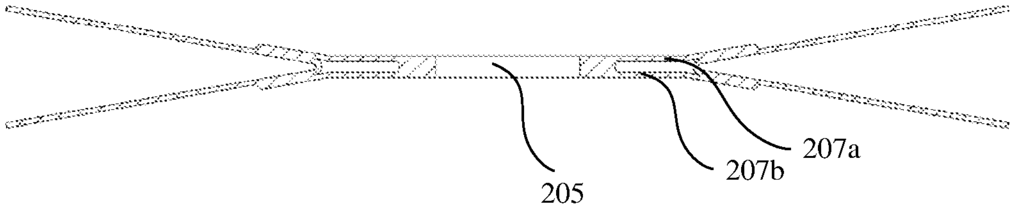

Step 3: Dispose a through hole 205 on the first curved surface structure 207*a* and the second curved surface structure 207*b*, where the through hole 205 penetrates the two curved surface structures; and connect parts that are of the first curved surface structure 207*a* and the second curved surface structure 207*b* and that are located on a periphery side of the through hole 205, where a connection manner may be, but is not limited to, jointing by performing a hot melt process, to obtain a structure shown in FIGS. 41*d*, and 41*e* is a sectional view of the structure shown in FIG. 41*d*.

In addition, in step 3, the first curved surface structure 207*a* and the second curved surface structure 207*b* may be first connected, and a connection area of the first curved surface structure 207*a* and the second curved surface structure 207*b* may be a strip shape or a dot shape, and then the through hole 205 is disposed in the connection area.

Figure 41F:
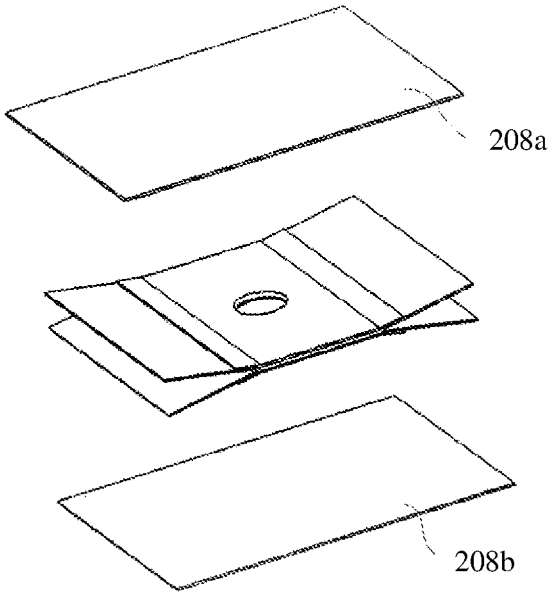
Figure 41G:
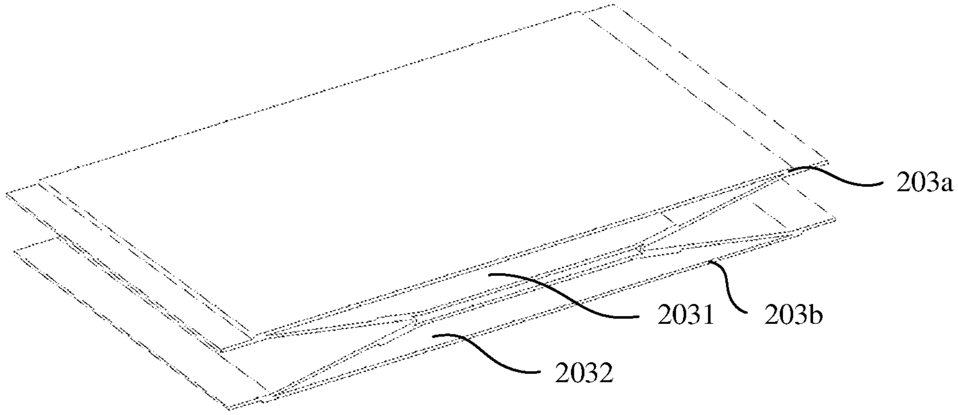
Figure 41H:
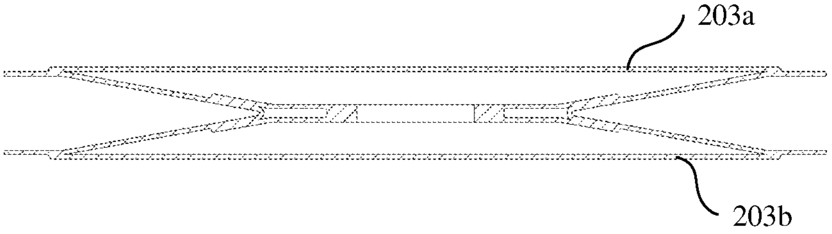

Step 4: Refer to FIG. 41*f*. Dispose a structure obtained in step 3 between a first cover surface structure 208*a* and a cover surface structure 208*b*. In addition, two opposite edges of the first cover surface structure 208*a* are respectively connected to the third curved surface structure 207*c* and the fourth curved surface structure 207*d*, and two opposite edges of a second cover surface structure 208*b* are respectively connected to the third curved surface structure 207*c* and the fourth curved surface structure 207*d*, to obtain a structure shown in FIG. 41*g*. FIG. 41*h* is a sectional view of the structure shown in FIG. 41*g*. In this case, the first curved surface structure 207*a*, the first cover surface structure 208*a*, the third curved surface structure 207*c*, and the fourth curved surface structure 207*d* form a first layer structure 203*a*, the first layer structure 203*a* has a first cavity 2031, the second curved surface structure 207*b*, the second cover surface structure 208*b*, the third curved surface structure 207*c*, and the fourth curved surface structure 207*d* form a second layer structure 203*b*, and the second layer structure 203*b* has a second cavity 2032.

After the foregoing step 4 is completed, an air nozzle 201 may be further installed. For example, the air nozzle 201 may be installed on a side that is of the second layer structure 203*b* and that is away from the first layer structure 203*a*, to facilitate a connection formed between the airbag 2 and a watch body 1. It may be understood that an air hole of the air nozzle 201 may be connected to the second cavity 2032 of the second layer structure 203*b*. Finally, openings at two ends of a structure obtained in FIG. 41*g* are jointed by performing a hot melt process, to form the closed airbag 2.

The airbag 2 obtained by using the method for preparing an airbag 2 provided in this embodiment of this application does not flip outward during inflating. It should be noted that in this embodiment, the first curved surface structure 207*a* and the second curved surface structure 207*b* may not be curved surfaces, provided that both the two layer structures of the prepared airbag 2 can have a cavity. In addition, the foregoing steps are an example of a preparation process of the airbag 2 in this embodiment of this application. Based on this embodiment, a person skilled in the art may properly adjust the foregoing steps to prepare the airbag 2 in this application, which should be understood as falling within the protection scope of this application.

Figure 42A:
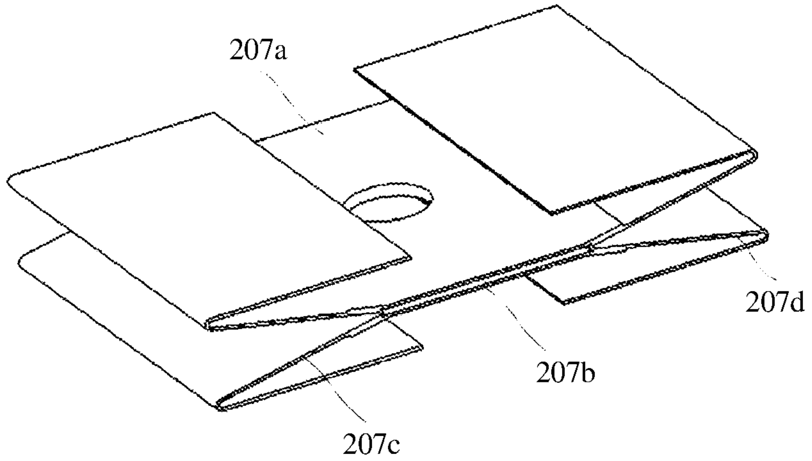
FIG. 42*a* to FIG. 42*e* are schematic diagrams of an airbag preparation process according to another embodiment of this application.
Figure 42B:
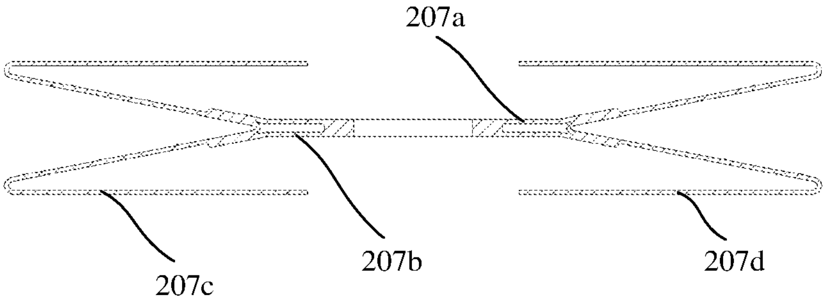

In another possible embodiment of this application, a method for preparing an airbag 2 is further provided. The method is similar to the method for preparing an airbag 2 in the foregoing embodiment, and a difference lies in that: After the structure shown in FIG. 41*d* is obtained, two edges at an opening of the third curved surface structure 207*c* are respectively bent in a direction away from each other, and two edges at an opening of the fourth curved surface structure 207*d* are respectively bent in a direction away from each other, to obtain a structure shown in FIG. 42*a*. FIG. 42*b* is a cross-sectional view of the structure shown in FIG. 42*a*.

In this case, cross-sectional shapes of the third curved surface structure 207*c* and the fourth curved surface structure 207*d* are M-shaped.

Figure 42C:
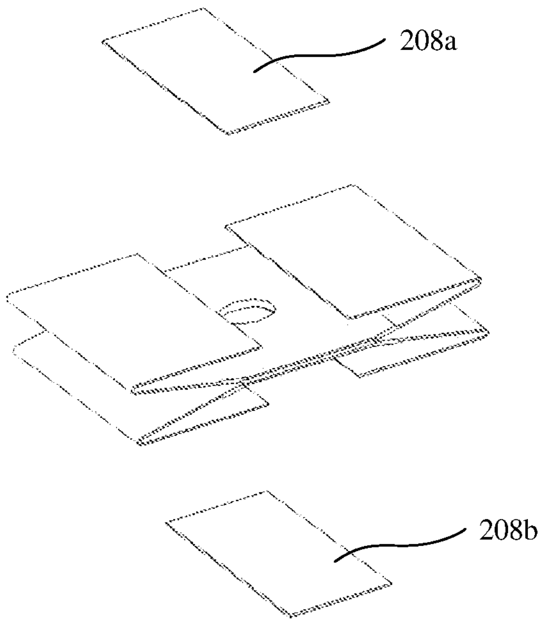
Figure 42D:
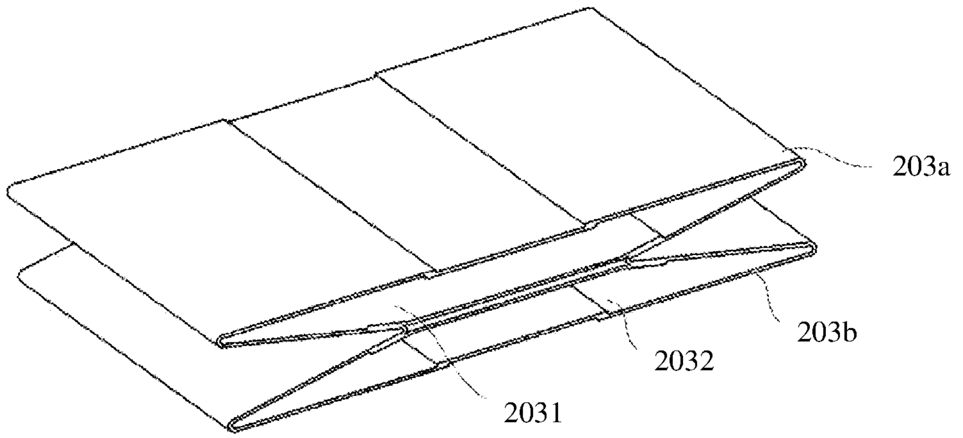
Figure 42E:
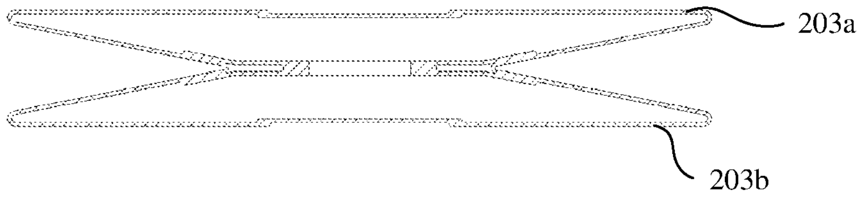

In addition, refer to FIG. 42*c*. In this embodiment, a first cover surface structure 208*a* and a second cover surface area structure 208*b* have smaller sizes than those in the foregoing embodiment. Two opposite edges of the first cover surface structure 208*a* are respectively connected to bent parts of a third curved surface structure 207*c* and a fourth curved surface structure 207*d*, and two opposite edges of a second cover surface structure 208*b* are respectively connected to bent parts of the third curved surface structure 207*c* and the fourth curved surface structure 207*d*, to obtain a structure shown in FIG. 42*d*. FIG. 42*e* is a sectional view of the structure shown in FIG. 42*d*. In this case, a first cavity 2031 is formed between the first curved surface structure 207*a*, the first cover surface structure 208*a*, the third curved surface structure 207*c*, and the fourth curved surface structure 207*d*, and a second cavity 2032 is formed between the second curved surface structure 207*b*, the second cover surface structure 208*b*, the third curved surface structure 207*c*, and the fourth curved surface structure 207*d*.

For other steps for preparing the airbag 2 in this embodiment, refer to the foregoing embodiment. Details are not described herein again. In addition, the foregoing steps are an example of a preparation process of the airbag 2 in this embodiment of this application. Based on this embodiment, a person skilled in the art may properly adjust the foregoing steps to prepare the airbag 2 in this application, which should be understood as falling within the protection scope of this application.

Figure 43:
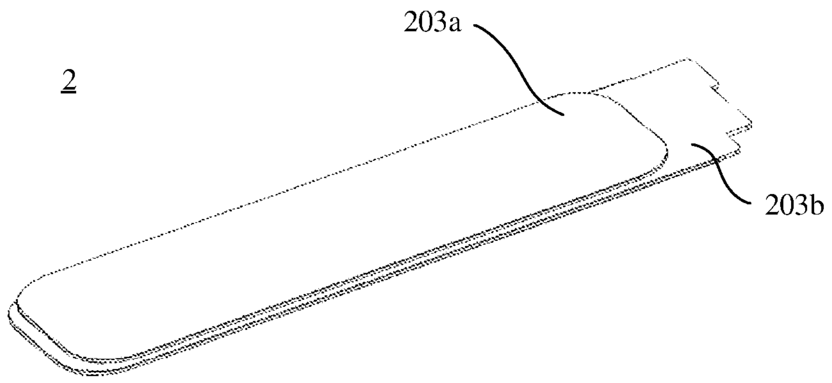
FIG. 43 is a schematic diagram of a structure of an airbag according to another embodiment of this application.

Refer to FIG. 43. FIG. 43 is a schematic diagram of a structure an airbag 2 according to an embodiment of this application. The airbag 2 obtained by using the preparation method in the foregoing embodiments of this application may include two layer structures that are superposed. When the airbag 2 is used, a first layer structure 203*a* of the airbag 2 is often in contact with a wearing part. Long-term use causes dirt to be attached to a surface of the first layer structure 203*a*, and the airbag 2 is inconvenient for cleaning. Based on this, this application further provides a protective sleeve 6. The protective sleeve 6 may be sleeved on the first layer structure 203*a* of the airbag 2, and is detachably connected to the first layer structure 203*a* of the airbag 2.

Figure 44A:
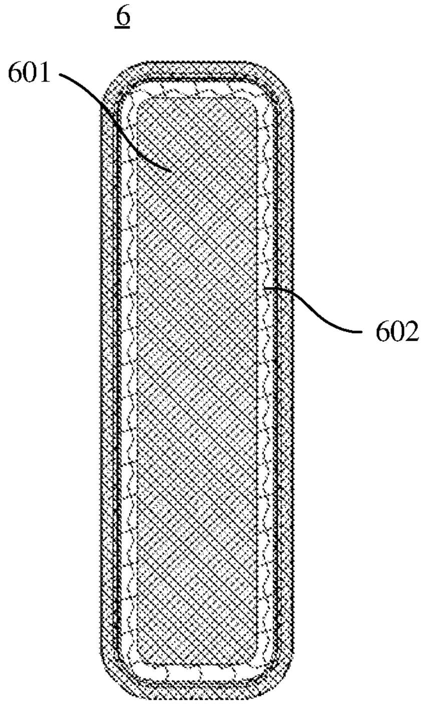
FIG. 44*a* is a front view of a protective sleeve according to an embodiment of this application.
Figure 44B:
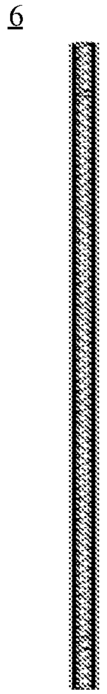
FIG. 44*b* is a side view of a protective sleeve according to an embodiment of this application.
Figure 44C:
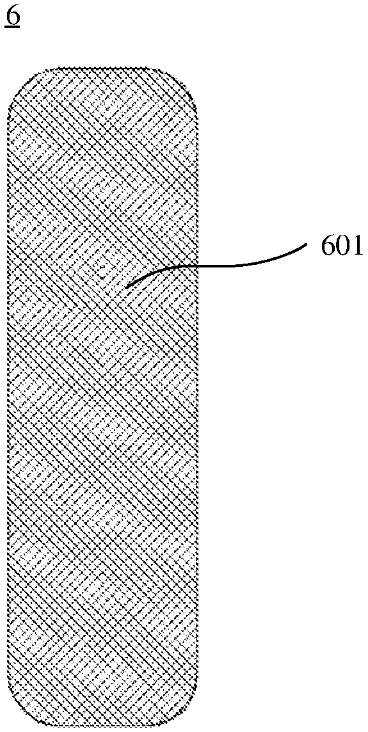
FIG. 44*c* is a rear view of a protective sleeve according to an embodiment of this application.

When the protective sleeve 6 is specifically disposed, refer to FIG. 44*a* to FIG. 44*c*. The protective sleeve 6 includes a sleeve body 601, and the sleeve body 601 is sleeved on the first layer structure 203*a* of the airbag. The sleeve body 601 may cover at least a surface that is of the first layer structure 203*a* and that is away from the second layer structure 203*b*. A size of the sleeve body 601 may be specifically disposed based on the first layer structure 203*a* of the airbag 2. In addition, the sleeve body 601 may be, but is not limited to, a mesh sleeve structure made of a textile fabric. In order to prevent the protective sleeve 6 from detaching from the first layer structure 203*a* of the airbag 2 shown in FIG. 43, the protective sleeve 6 may further include an edge wrap 602. The edge wrap 602 is disposed around an edge of the sleeve body 601 and is connected to the sleeve body 601. A material of the edge wrap 602 may be, for example, leather or another elastic material.

Figure 45:
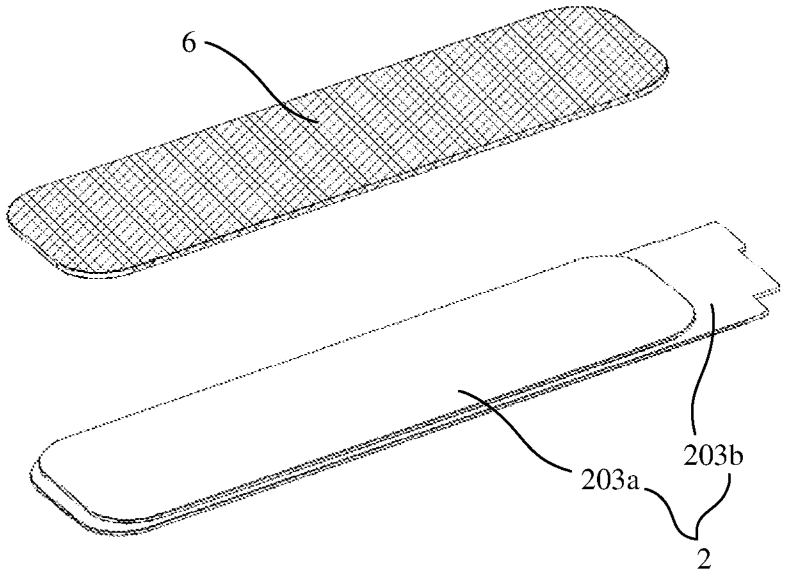
FIG. 45 is a schematic diagram of an assembly process of a protective sleeve and an airbag according to an embodiment of this application.

Refer to FIG. 45. FIG. 45 shows a process in which a protective sleeve 6 is sleeved on an airbag 2 according to an embodiment of this application. Generally, both the airbag 2 and the protective sleeve 6 have certain elasticity. Therefore, the protective sleeve 6 may be sleeved on the first layer structure 203*a* of the airbag 2 based on elastic deformation of the airbag 2 and the protective sleeve 6, so that the protective sleeve 6 is attached to the first layer structure 203*a*, and the protective sleeve 6 is prevented from falling off from the first layer structure 203*a* in a process of wearing and using the airbag 2.

Figure 46:
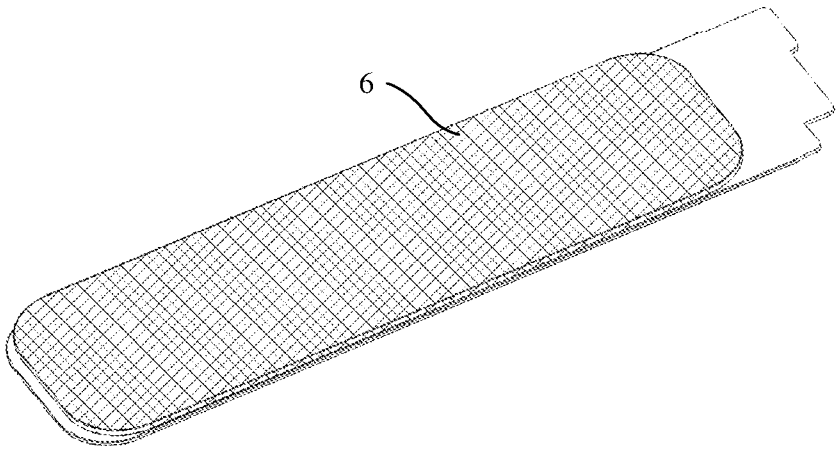
FIG. 46 is a schematic diagram of an assembly structure of a protective sleeve and an airbag according to an embodiment of this application.

Refer to FIG. 45 and FIG. 46 together. FIG. 46 shows an airbag sleeved with a protective sleeve 6. In addition to a contact surface between a first layer structure 203*a* and a second layer structure 203*b* of the airbag, the protective sleeve 6 completely wraps a remaining surface of the first layer structure 203*a*. This can effectively improve wearing comfort of a user. In addition, because the protective sleeve 6 is detachably connected to the first layer structure 203*a*, the airbag 2 may be kept clean by cleaning or replacing the protective sleeve 6.

The foregoing descriptions are merely specific implementations of this application, but are not intended to limit the protection scope of this application. Any variation or replacement readily figured out by a person skilled in the art within the technical scope disclosed in this application shall fall within the protection scope of this application. Therefore, the protection scope of this application shall be subject to the protection scope of the claims.

What is claimed is:

1. A wearable device, comprising:

a watch body;

an airbag, wherein the airbag is detachably connected to an end of the watch body, the airbag comprises a first layer structure and a second layer structure that are superposed, the first layer structure has a first cavity, the second layer structure has a second cavity, and the first cavity communicates with the second cavity; and an airbag cover, wherein the airbag cover is detachably connected to the watch body, and the airbag is operable to be fastened to the watch body using the airbag cover;

an air nozzle having a first portion disposed within the second cavity of the second layer structure and a second portion extending out of the second layer structure, the air nozzle comprising an air hole connected to the second cavity; and a support protrusion disposed on a first surface of the first portion of the air nozzle facing an interior of the second cavity and extending toward the interior of the second cavity, wherein the support protrusion is disposed on a peripheral side of the air hole, wherein:

the airbag cover further comprises a pressing plate, and the pressing plate is fastened to a cover body of the airbag cover, the pressing plate is provided with an air nozzle hole, a part of the airbag on which the air nozzle is disposed is located between the pressing plate and the cover body, and the air nozzle extends out of the air nozzle hole, the airbag cover further comprises an elastic protrusion, the cover body has an accommodating cavity, the elastic protrusion is disposed at the accommodating cavity, and the elastic protrusion is operable to move in a direction toward or away from the accommodating cavity.

2. The wearable device according to claim 1, wherein the end of the watch body that is detachably connected to the airbag is disposed on a bottom surface of the watch body, wherein the end is provided with an installation slot, wherein both the airbag and the airbag cover are operable to be installed in the installation slot, and wherein the airbag and the airbag cover are detachably connected to the watch body.

3. The wearable device according to claim 2, wherein the wearable device further comprises a photoplethysmography (PPG) module and an electrocardiogram (ECG) detection module, and the PPG module and the ECG detection module are disposed on the bottom surface of the watch body.

4. The wearable device according to claim 2, wherein the watch body comprises an air chamber, an air pump, and a pressure sensor, wherein the air chamber has an air nozzle installation hole and an air inlet/air outlet, wherein an air supply opening of the air pump communicates with the air inlet/air outlet, and wherein the pressure sensor is configured to detect barometric pressure in the air chamber; and wherein the air nozzle is inserted into the air nozzle installation hole.

5. The wearable device according to claim 4, wherein there is only one air nozzle installation hole comprised in the air chamber, and there is only one air nozzle comprised in the wearable device.

6. The wearable device according to claim 4, further comprising a first flexible inner object disposed in the first layer structure, and at least a part of the first flexible inner object is fastened to an inner wall of the first layer structure.

7. The wearable device according to claim 4, further comprising a second flexible inner object disposed in the second layer structure, and an end of the second flexible inner object is connected to the air nozzle.

8. The wearable device according to claim 1, wherein:

the elastic protrusion comprises a protrusion cover and an elastic component, and both the elastic component and the protrusion cover elastically abut against a bottom wall of the accommodating cavity of the cover body; and the pressing plate is further provided with a protrusion cover hole, and the protrusion cover extends from the protrusion cover hole to a side of the pressing plate away from the cover body.

9. An airbag assembly, detachably connected to a watch body, wherein the airbag assembly comprises:

an airbag comprising:

a first layer structure and a second layer structure that are superposed, wherein the first layer structure has a first cavity, the second layer structure has a second cavity, and the first cavity communicates with the second cavity, an air nozzle having a first portion disposed within the second cavity of the second layer structure and a second portion extending out of the second layer structure, the air nozzle comprising an air hole connected to the second cavity, and a support protrusion disposed on a first surface of the first portion of the air nozzle facing an interior of the second cavity and extending toward the interior of the second cavity, wherein the support protrusion is disposed on a peripheral side of the air hole; and an airbag cover, wherein the airbag is operable to be fastened to the watch body using the airbag cover, wherein:

the airbag cover further comprises a pressing plate, and the pressing plate is fastened to a cover body of the airbag cover, the pressing plate is provided with an air nozzle hole, a part of the airbag on which the air nozzle is disposed is located between the pressing plate and the cover body, and the air nozzle extends out of the air nozzle hole, and the airbag cover further comprises an elastic protrusion, the cover body has an accommodating cavity, the elastic protrusion is disposed at the accommodating cavity, and the elastic protrusion is operable to move in a direction toward or away from the accommodating cavity.

10. The airbag assembly according to claim 9, further comprising a first flexible inner object disposed in the first layer structure, wherein at least a part of the first flexible inner object is fastened to an inner wall of the first layer structure.

11. The airbag assembly according to claim 10, further comprising a second flexible inner object disposed in the second layer structure.

12. The airbag assembly according to claim 9, wherein:

the elastic protrusion comprises a protrusion cover and an elastic component, and both the elastic component and the protrusion cover elastically abut against a bottom wall of the accommodating cavity of the cover body; and the pressing plate is further provided with a protrusion cover hole, and the protrusion cover extends from the protrusion cover hole to a side of the pressing plate away from the cover body.

* * * * *